US010246731B2

(12) United States Patent
O'Keefe

(10) Patent No.: US 10,246,731 B2
(45) Date of Patent: Apr. 2, 2019

(54) METHOD FOR RAPIDLY DETERMINING EFFECTIVE STERILIZATION, DEIMMUNIZATION, AND/OR DISINFECTION

(71) Applicant: ONEighty°C Technologies Corporation, Burlington, MA (US)

(72) Inventor: Theresa L. O'Keefe, Waltham, MA (US)

(73) Assignee: ONEighty°C Technologies Corporation, Burlington, MA (US)

( * ) Notice: Subject to any disclaimer, the term of this patent is extended or adjusted under 35 U.S.C. 154(b) by 0 days.

(21) Appl. No.: 15/472,499

(22) Filed: Mar. 29, 2017

(65) Prior Publication Data

US 2017/0283847 A1  Oct. 5, 2017

Related U.S. Application Data

(60) Provisional application No. 62/314,617, filed on Mar. 29, 2016.

(51) Int. Cl.
*C12Q 1/22* (2006.01)

(52) U.S. Cl.
CPC ...................... *C12Q 1/22* (2013.01)

(58) Field of Classification Search
None
See application file for complete search history.

(56) References Cited

U.S. PATENT DOCUMENTS

| | | | |
|---|---|---|---|
| 5,073,488 A * | 12/1991 | Matner | C12Q 1/22 435/31 |
| 7,851,178 B1 | 12/2010 | Belhumeur et al. | |
| 8,034,766 B2 | 10/2011 | Croud et al. | |
| 8,293,174 B2 | 10/2012 | Kaiser et al. | |
| 9,480,761 B2 | 11/2016 | Kritzler et al. | |
| 2006/0217282 A1 | 9/2006 | Jackson et al. | |
| 2009/0118470 A1 | 5/2009 | Riesner et al. | |
| 2011/0123508 A1 | 5/2011 | Kritzler et al. | |
| 2012/0315627 A1 * | 12/2012 | Aojula | C12Q 1/04 435/5 |
| 2015/0315530 A1 | 11/2015 | Frieze | |

FOREIGN PATENT DOCUMENTS

| | | |
|---|---|---|
| EP | 1377677 B1 | 2/2012 |
| WO | 2002053723 A2 | 7/2002 |

OTHER PUBLICATIONS

Rutala et al., "Guideline for Distinfection and Sterilization of Prion-Contaminated Medical Instruments", Infection Control and Hospital Epidemiology, Feb. 2010, vol. 31, No. 2, (twelve (12) pages).

Fichet et al., "Investigations of a Prion Infectivity Assay to Evaluate Methods of Decontamination", ScienceDirect, Journal of Microbiological Methods, 70 (2007), pp. 511-518.

* cited by examiner

*Primary Examiner* — Mary Maille Lyons
(74) *Attorney, Agent, or Firm* — Iandiorio Teska & Coleman, LLP

(57) ABSTRACT

A method for rapidly determining effective sterilization, deimmunization, and/or disinfection of equipment and/or supplies by a device. The method includes providing a defined surrogate protein having a predetermined sequence representative of an infectious agent potentially contaminating the equipment and/or the supplies to be sterilized, deimmunized, and/or disinfected by the device. The defined surrogate protein having the predetermined sequence is subjected to sterilization, deimmunization, or disinfection. The effectiveness of the sterilization deimmunization, or disinfection is rapidly determined by determining if the defined surrogate protein has been destroyed.

15 Claims, 29 Drawing Sheets

Specification includes a Sequence Listing.

|  | 10 | 20 | 30 | 40 | 50 | 60 |
|---|---|---|---|---|---|---|
| Human | KKRPKPGG.W | NTGGSRYPGQ | GSPGGNRYPP | Q.......G | GGGWGQPHGG | GWGQPHGGGW |
| Macaque | ---------,- | ---------- | ---------- | -,...,..- | ---------- | ---------- |
| Cat | --------G- | ---------- | ---------- | -,...,..- | ---------- | ---------- |
| Dog | --------G- | ---------- | ---------- | -,......- | ---------- | ---------- |
| Cow | --------G- | ---------- | ---------- | -GGGGWGQPH | ---------- | ---------- |
| Sheep | --------G- | ---------- | ---------- | -,...,..- | ---------- | ---------- |
| Mouse | ---------,- | ---------- | ---------- | -,......- | --T------- | ---------S- |
| Rat | ---------,- | ---------- | ---------- | -.......S | --T------- | ---------- |

|  | 70 | 80 | 90 | 100 | 110 | 120 |
|---|---|---|---|---|---|---|
| Human | GQPHGGGWGQ | PHGGG.WGQG | GGTHSQWNKP | SKPKTNMKHM | AGAAAAGAVV | GGLGGYMLGS |
| Macaque | ---------- | -----,---- | ----N----- | -----S---- | ---------- | ---------- |
| Cat | ---------- | -----G---- | -.S------- | ---------- | ---------V | ---------- |
| Dog | ---------- | -----G---- | -,--G----- | ---------- | ---------V | --------L-- |
| Cow | ---------- | -----G---- | -,--G----- | ---------- | ---------V | ---------- |
| Sheep | ---------- | -----G---- | -.S------- | ---------- | ---------V | ---------- |
| Mouse | -----S---- | -----,---- | ----N----- | ------L--V | ---------- | ---------- |
| Rat | ---------- | -----,-S-- | ----N----- | ------L--V | ---------- | ---------- |

|  | 130 | 140 | 150 | 160 | 170 | 180 |
|---|---|---|---|---|---|---|
| Human | AMSRPIIHFG | SDYEDRYYRE | NMHRYPNQVY | YRPMDEYSNQ | NNFVHDCVNI | TIKQHTVTTT |
| Macaque | ---------- | N--------- | ---Y------ | ---V-Q---- | ---------- | -V-------- |
| Cat | ---------- | N--------- | ---Y------ | ---V-Q---- | ---------- | -V-------- |
| Dog | ---------- | N-C------- | ---Y------ | --SV-Q-N-- | ST-------- | -V-------- |
| Cow | ---------- | ---------- | ---------- | ---V-Q---- | ---------- | -V-E------ |
| Sheep | ---------- | N--------- | ---Y------ | ---V-R---- | ---------- | -V-------- |
| Mouse | ----M----- | N--------- | ---Y------ | ---V-Q---- | ---------- | ---------- |
| Rat | ----ML---- | N--------- | ---Y------ | ---V-Q---- | ---------- | ---------- |

|  | 190 | 200 | 210 | | |
|---|---|---|---|---|---|
| Human | TKGENFTETD | VRMMERVVEQ | MCITQYERES | QAYY | SEQ ID NO: 26 |
| Macaque | ---------- | ---------- | ------K--- | ---- | SEQ ID NO: 27 |
| Cat | ---------- | M-I------- | ---V----QK- | E---QRRAS | SEQ ID NO: 28 |
| Dog | ---------- | I--------- | ------Q--- | E--- | SEQ ID NO: 29 |
| Cow | ---------- | I--------- | ------Q--- | ---- | SEQ ID NO: 30 |
| Sheep | ---------- | I-I------- | ------Q--- | ---- | SEQ ID NO: 31 |
| Mouse | ---------- | ---------- | --V---QK-- | ----DGRRS | SEQ ID NO: 32 |
| Rat | ---------- | ---------- | --V---QK-- | ----DGRRS | SEQ ID NO: 33 |

Amino Acid Sequence Comparison of Human PrP Proteins with a Selection of other Species PrP Proteins. Residues cover only standard mature protein sequences.

*FIG. 4*

(Clostridium)
Homology Diagram comparing protein sequence in a research (non-pathogenic) Clostridium species and 2 pathogenic Clostridium species. Standard single letter amino acid abbreviation is used. [-] indicates amino acid homology. [.] indicates gap in sequence.

```
                    10         20         30         40         50
C. sporogene   MEVNPLDPKL ........ IPKYTQELVI PRSELPTVCI SSVSGAVS.YN YTVTMNQHHQ
C. botulinum                                           I          Y--AKE-A--    200
C. novyi       -NIRRDNLRD ILDPNT--- -YVEQ-P--- -KV-V-QLIK DPNTCMVKGHY 60         70         80         90        100
C. sporogene   QILPPEFNPT TVWGYGGTIK DTSTGEEVKP .QNAPGFTFEA VRGIPVNYKW
C. botulinum                                   T          D--I                  200
C. novyi       L--RC-PK-  I-------- -KV- WF-- IYHD YRSY-- -T--V-I-Q--

110        120        130        140        150
C. sporogene   VNEITAPYSL AVDPTMHWAH PNNTPMPPPP GGWPFPFPGV PELAQKDVELV
C. botulinum                                     T         D                    200
C. novyi       -NL-GINP-  -------L- -D -MIG-IKP-. QDV----- L --Q--YPI--

160        170        180        190        200
C. sporogene   PHLHGGEQAS MPDGSRPEAWW TAKGLKGSHY  IDDIFHYLMKQ ESTTLMYHD
C. botulinum   T                            -PK-            -P-V-              200
C. novyi       T--------  VCS T--H---- -F -SNEKLIGPQ FGTSLYQ--  -P--A---

210        220        230        240        250
C. sporogene   HALGVTRLNV VMGLAGFYIL KDPANPLOYP GPLITSAKVR VPIAIQQRSF
C. botulinum                                              -S-                  202
C. novyi       T--L-----  --------- -I         -KM-P--K-  -CILPDR-C- -I-LV--DHT-
Test Protein                                                          -MINY--

260        270        280        290        300
C. sporogene   MEDGSLNFPS EGDNPTIHFY WQPEFFGDTI MVRGRVWPNM NVDMCKYRFR
C. botulinum                                              I K      -EQTM--      202
C. novyi       I--Y--N  V----- -D--- ----N---- S--MT----  -L------
Test Protein   --------- --------- --------- --------- ----------
```

FIG. 7

```
                    310        320        330        340        350
C. sporogene  LLNGSNARFV NLKFSNSMQF WQIGTDGGYL NKPVPLTSLL ISPGERADIL ─┐
C. botulinum  M---A----- ---F-T---- ---N-S---- ---S----L- EQ-K-QE-T  │ 202
C. novyi      ---------- ---------- ---------- ---------- LA-AQ----- ─┘
Test Protein 360        370        380        390        400
C. sporogene  VDFTEIPAGT RILLMNDANA PYFPADAPDK DTTQQIMQFT VQHHIDMNIP
C. botulinum  ---------- ----K----- ---------- ---------- ---N--M---
C. novyi      I--SSLKK-- ---K------ -S-------- --FSSIK-NN Q-V--V----  ─┐ 202
Test Protein                                              KGCYKPFFKL │
                                                          HHHHH      ─┘

410        420        430        440        450
C. sporogene  PELPEKLRCE PVPKLKSPCK BRVLTLYEIA GPNGP QMFTL NGQPWADPVS ─┐
C. botulinum  ---------- ---------Q K--------- ---------- -T-SA----- │ 204
C. novyi      V-.-K--NNI -MLVPNK... -K-------- K--IEI T-TG-I--. L-D- │
Test Protein H SEQ ID NO: 1                                K-SA-IT  ─┘

460        470        480        490        500
C. sporogene  ELPVVGSTEE WNIVNLITMDA HPIHLHLVQF KIACRQAFDV DAYTNDWIDL ─┐
C. botulinum  ---------- ----D----- ---------- ---------- ---N--E--- │ 204
C. novyi      ---------- ----L--EL- ----V-T--- ---------- QLQD--K-NS ─┘
                                                          --N--

510        520        530        540        550
C. sporogene  MSDIGSPPNM TTPKALCPGS YITGDDQPPA AMEAGWKDTV QAFPGEITRI ─┐
C. botulinum  ---------- --LP------ ---------- ---TI--N-- ---I---P-- │ 204
C. novyi      V..-YL-IN- HPT--ID--I -LQ--PI--D P--K--M--- R-Y--V---- ─┘

560        570        580        590        600
C. sporogene  RVRFAPQDVK TSC..PGENLYL FTDPSKGPGYV WHCHILDHED NDMMMRPYPVF P 601 SEQ ID NO: 34 ─┐
C. botulinum  ---N-E---- --P------- ---------- ---D------ ---M------L . 599 SEQ ID NO: 35 │
C. novyi      L-----IDAD --QVR--K-- P--A-QE--- ---------M ---E------MI-M NKQINNINRL 614 SEQ ID NO: 36 ─┘
```

```
                   260        270        280        290        300
B subtilis    RFRVINASNT RTYNLSLDNG GDFIQIGSDG GLLPRSVKLN SFSLAPAERY
B atrophae    ----IV---- ---------- -E-L-V---- ---------S ---------I    216
B pumilis     ----IL---- ----E-H--D ATIM------ ---F---P-RHQ -------I--F 310        320        330        340        350
B subtilis    DIIIDFTAYE GESIILANSA GCGGDVNPET DANIMQFRVT KPLAQKTKAE
B atrophae    -------A-F- --Q--V---- ---A--S--- -----V---- --KE-D----
B pumilis     ----V----S- NKT-T-K-T- -------Q-- ------K--- R---KGRVPKT    216

360        370        380        390        400
B subtilis    SRSTSPHT...LR YSMKDTNIRT LKLAGTQDEY GRPVILLNNK RWHDPVTETP
B atrophae    --KPRFL-NLPPV TDEKIQ--L- ---------T ---------- --S------A    218
B pumilis     .LRPIEKPLEP-- .PSRADRE-- --T-T----K- -------I-- -D-H F-----

410        420        430        440        450
B subtilis    KVGTTEIWSI INRHAEHILI HLHLVSFRVL DRPFDIARY QESGELSYTV
B atrophae    ---L---S-- ---------- --PTRGTHP- ---------- -T-K- A-TN-V-F-G    218
B pumilis     RL-SL-V--- ---V-PTRGTHP- -------Q--I -TEV- -ST--IV--G 460        470        480        490        500
B subtilis    RCPAAA.SEKG WKDTIQAHAG EVLRIAATFG PVSGRYVWHC HILEHEDYDM
B atrophae    PAVPPPP--- -------V-S- ---------- ---I--M-K- ----------    218
B pumilis     PME-PPLH-Q- ---------Y- ---------- ---I--V-R-V ----------

510
B subtilis    MRPMDITDPH K     511  SEQ ID NO: 37
B atrophae    ------VV--- N Q   513  SEQ ID NO: 38
B pumilis     ---------IQ      510  SEQ ID NO: 39
                218
```

```
                       260        270        280        290        300
M tuberculosis   LINGRIPVAA TSFKA

```
              260        270        280        290        300
s. aureus      VNPKLTAKEE KIRLRILNGS NARDLNIKLS NNQSFEYIAS DGGQLKNAKK ⎤
s. epidermidis ---------- ---------- ---------- ---------- ---------- ├─ 242
s. saprophyticus -D-----T--G ---------- ---------- E--H-EKT-- ---------- ⎦

310        320        330        340        350
s. aureus      LKEINLAPSE RKEIVIDLSK MKGEKISLVD NDKTVILPIS NKEKSSNKSN
s. epidermidis ---------- ---------- ---------- ---------- ----G-----
s. saprophyticus ---------A ---------- E----VN--- -----E---- ---------- ⎤
                                                    I              ├─ 242
                                                    T--DI          ⎦

360        370        380        390        400
s. aureus      TPKVGKKIKL EGMNDNVTIN GNKFDPNRID FTQKLNQKEV WEIENVKDKM ⎤
s. epidermidis ---------S ---------H ---------- ---------- ---------- ├─ 246
s. saprophyticus ---------D ---------- ---K------ -----V-R-T ---------- ⎦

410        420        430        440        450
s. aureus      GGMKHPFHIH GTQFKVLSVD GEKPPKDMRG KKDVISLEPG QKAKIEVVFK ⎤
s. epidermidis ---------- ---------- ---------- ---------- ---------I ├─ 246
s. saprophyticus ---------- ---------- K--ES----- ---------- ---------- ⎦

460        470
s. aureus      NTGTYMPHCH ILEHEDNGMM GQVKVTN 477 SEQ ID NO: 43
s. epidermidis ---------- ---E------ ------- 477 SEQ ID NO: 44
s. saprophyticus ---------- ---------- -----I-K 477 SEQ ID NO: 45
                                      └─ 246
```

*FIG. 13 Continued*

```
                    260        270        280        290        300
P. aeruginosa     VEPRGFEGQY WIGPGMRLEL ALKVPEAGTE LSLRDGPVRL ATIRSVASAE
P. fluorescens    ----FLGKE- -L-----IC- -I-A-P--E- ----N----- ----G-L---NND
P. putida         --T-AL.DE- -L-----IC- -IRI-----E -I---F---- ----G-L---ND
Test Protein                                                       HHH 310        320        330        340        350
P. aeruginosa     APAGDWPKPL PANPVSEPDL ANAEKIGFRF EWVGAMSDTS GKNPYPSFWQ
P. fluorescens    --T.E----- -----A---- -----LN--N -----SV-VNV DNGKPP-L---
P. putida         --S.D--PA- -P---IA--- -----EH--- -LN--N-- ---AAGV-VTA DPAKPS-M---
Test Protein      HHH SEQ ID NO: 5

360        370        380        390        400
P. aeruginosa     INGKAWEGGE EHKHNAPPLA KLKEGQSYIF ELRNMAQYQH PIHLHGMAFK
P. fluorescens    ----VITD KTCADR-IASL --------- ------K--T --------S---
P. putida         ----Q--DITD KTCADR-IATL Q..-K--- ------K--T --------S---

410        420        430        440        450
P. aeruginosa     VLDSDRREII .PYFTDTYLIG KNETARVALV ADNPGLWMFH CHVIDHMETG
P. fluorescens    --IA-N-HK- ---------- ---------- -----R-Q-- -------V---
P. putida         --IA-N-HD-K EPW-------- ---------- ---------- -----R-Q-- -------T---

460
P. aeruginosa     LMGTIAVGEA WCG         463 SEQ ID NO: 46
P. fluorescens    ---AA-E--K            458 SEQ ID NO: 47
P. putida         ---AA----V            459 SEQ ID NO: 48
```

FIG. 15 Continued

```
                 310        320        330        340        350
T. rubrum     DVLKWFKSLE ANGQEPVPDS FLINGAGRFN CSMALPTRPI DCVDEGYPTP ⌐272
T. tonsurane  ---------N ---------- ---------- ---------- -L-------

360        370        380        390        400
T. rubrum     ELLLDSST..SY RMRVINVGSL AGVSLGFEHG TVTPIQVDSG TEVELPSYSP ⌐272
T. tonsurane  ---SSS------ ---------- ----A----- ---------- ----------

410        420        430        440        450
T. rubrum     NARSMGIVYP GQRTDEVLRN ELGETGQSSI TVELDEECFS LPNPALTRVQ ⌐272
T. tonsurane  -------I-- ---------- ---------- AF-GAE---- ----------

460        470        480        490        500
T. rubrum     TFPISGSAKK PS.HPLSDNPI GEAGTHVDLT ELTSTASTIS HIPAKADETF ⌐274
T. tonsurane  -------K-- --S-T------ ----S----- ---------- ----E-----

510        520        530        540        550
T. rubrum     LVYTLLSKLS SNNYVPFAFF NHTSWRPQAD PELPLISLQR KDWDKRQFTI ⌐274
T. tonsurane  ---------- ---------- ---------- ---------- ----------

560        570        580        590        600
T. rubrum     KTSSRASWVD LIVNRILDEGP HPFHINGHDF YVMSLHEADT GMGSYNFWDP ⌐274
T. tonsurane  -------K-- ---V------ ---------- ---------- ----------

610        620        630        640        650
T. rubrum     SNKAPAYDHS QAILRDTVHI PARGHAVLRF RADNPGIWLF HCHILWHLAS ⌐274
T. tonsurane  -------Q-- ----N----- ---------- ---------- ----------

660        670
T. rubrum     ⌐GMAMLVDVMD SASRPFLHGIL NQTCRYLT   SEQ ID NO: 49
T. tonsurane   ----V----P ---------- --------   SEQ ID NO: 50
              274
```

*FIG. 17 Continued*

```
                    360        370        380        390        400
Candida albicans    GVNYAFFNNI TYMTPKVPTL LSVLSAGDAS TNELVYGSNT NSFVLQGGDV ⎤
Candida dubliniensis ---------- --KA------ -T-------A -----I--T-- ---------- ⎬ 284
Candida tropicalis  ---------- --AH------ M----S--DA S-------T-- ---------E- ⎪
Candida auris       ---------- S-VA--I-L- ATAM---ELA --SYI--.--- -A----KK-ET ⎦

410        420        430        440        450
Candida albicans    VDIVLNNLDT GRHPFHLHGH VFQLIERHKE IPDTEDPVSY NVSDHAEWPE ⎤ 284
Candida dubliniensis ---------- -K-------- A-------K- ---------T- -AT---D--- ⎬
Candida tropicalis  I---M----- -K-------- ---------- -EG VD-D----A- -S-------- ⎪
Candida auris       ------Q-D -T-------- ---------- -.G PEF.G----F DYNN-S-F-- ⎦

460        470        480        490        500
Candida albicans    YPMSRDTVYV KPQSYIVMRF KADNPGVWFF HCHIEWHLDQ GLAIVLIEDP ⎤ 284
Candida dubliniensis ---M------ R--------- ---------- ---------E- ---FQ----- ⎬
Candida tropicalis  ---L---I-I N-----A-L- ---------- ---------- ---------- ⎪
Candida auris       ---K------ N-N------- T--------- ---------E- ------V-A- ⎦

510        520        530        540        550
Candida albicans    EAIQKNSSQH LTDNHKQICE KVGVSWEGHA AAHSNNYLDL KGENIQVKRL
Candida dubliniensis -G---QE--Q I------E--- ----P----- -GNTE------ ----V-H---
Candida tropicalis  Q-----E..K I--------- ----P-Q--- ---NKD--N- D---L-----
Candida auris       -EM--DP--Q ---E-F-DV-S -G-MNYS--- -G--VDPM-- T-M-T-P---

560        570        580        590        600
Candida albicans    PTGFTARGIV ALVFSCIAAF LGIAAIAYYG MNDIEDVEER VARDLDVDLD
Candida dubliniensis ------K--- -------G-- --M---S--- -----QNM-K- I------YF-
Candida tropicalis  ------K--- ------GV -LV--S--- -T--KN--Q- ----------
Candida auris       -A-------- ------GV --MV--TI-- LA-VK-ID-- ----------

610        620
Candida albicans    EENEDEEEAE IVHEGSSSSG SNSKQH  SEQ ID NO: 51
Candida dubliniensis DDE-EDQS.. -TEQDATG-S -SPSNK  SEQ ID NO: 52
Candida tropicalis  DDDVEQLSEE GSSGSN-KQH         SEQ ID NO: 53
Candida auris       -IAA--SSQ. L-PGD---RN K        SEQ ID NO: 54
```

METHOD FOR RAPIDLY DETERMINING EFFECTIVE STERILIZATION, DEIMMUNIZATION, AND/OR DISINFECTION

RELATED APPLICATIONS

This application claims benefit of and priority to U.S. Provisional Application Ser. No. 62/314,617 filed Mar. 29, 2016, under 35 U.S.C. §§ 119, 120, 363, 365, and 37 C.F.R. § 1.55 and § 1.78, which is incorporated herein by this reference.

FIELD OF THE INVENTION

This invention relates to a method for rapidly determining effective sterilization, deimmunization, and/or disinfection.

BACKGROUND OF THE INVENTION

A wide range of infectious agents, including infectious proteins, spore forming bacteria, vegetative bacteria, fungus and viruses have major impacts in medical settings. The process to remove infectious organisms or render them non-infectious from medical equipment makes use of a wide range of sterilization devices or equipment and disinfection devices and processes. The CDC lists examples of infectious agents and microorganisms by resistance to standard disinfection and sterilization processes. See Table 1 below from CDC's Guideline for Disinfection and Sterilization in Healthcare Facilities, 2008.

Some infectious agents, such as the HIV virus, may be easy to remove from medical equipment. Many infectious agents, including vegetative bacteria, are moderately difficult to eliminate. Other infectious agents, such as prions, can only be destroyed by extremely harsh conditions that damage and/or destroy modern medical equipment. Failure to eliminate infectious agents from medical equipment before use can put patients at extreme risk of injury and death.

TABLE 1

Decreasing order of resistance of infectious agents and microorganisms to disinfection and sterilization.

| Agent Category | Example Organisms or Diseases |
| --- | --- |
| Prions | Creutfeldt-Jakob Disease |
| Bacterial spores | *Bacillius atrophaeus* |
| Coccidica | *Cryptosporidium* |
| Mycobacteria | *M. tuberculosis, M. terrae* |
| Nonlipid or small viruses | polio, coxsackie |
| Fungi | *Aspergillus, Candida* |
| Vegetative bacteria | *S. aureus, P. aeruginosa* |
| Lipid of medium-sized viruses | HIV, herpes, hepatitis B |

Some conventional methods to determine if sterilization equipment functions effectively may rely on FDA approved Biologic Indicator process (BI strips) in a multi-step process. This widely accepted conventional process starts with filter papers infused with a defined number of bacterial spores (BI strips). The BI strips are subjected to a standard cycle by the sterilization equipment or device, e.g., an ethylene oxide (EtO) sterilization, radiation, or steam sterilization equipment which is being qualified. After the sterilization process is completed, the treated strips are then placed in a defined bacterial media for growth; frequently for days to weeks. If no growth is seen after the defined period, the sterilization process by the medical equipment being certified is declared a success. Together this combination of supplies and techniques is the approved process to qualify sterilization equipment in positive or negative process. If there is growth, the sterilization equipment fails and if there is no growth the sterilization equipment passes.

The conventional biologic indicator tests may use one of three different species of bacteria. The standard species used to test the effectiveness of ethylene oxide (EtO) sterilization is *B. atrophaeus*. To test the effectiveness of gamma radiation sterilization, the bacteria species used is *B. pumilis*. To test the effectiveness of steam sterilization the bacteria species used is *G. stearothermophilus*. However, the three species that are used to qualify sterilization capacity of equipment are not bacteria that commonly cause disease in humans. Instead, the species are surrogate species, strains of soil bacteria that form high persistent spores. They are used instead of medically relevant infectious agents, because, inter alia, the spores of the bacteria are extremely difficult to damage such that they can no longer replicate, and if for some reason a health care worker or patient accidently comes in contact with the spores through use or on improperly cleaned equipment, there is very little chance that the human will become ill. As spores from the surrogate species are scientifically known to be more difficult to destroy than medically relevant species, such as Polio or *S. aureus*, e.g., Methicillin-resistant *Staphylococcus aureaus* (MRSA), when the sterilization equipment is qualified to destroy all spores on a BI test strip, the FDA accepts that the equipment is also able to destroy all organisms that rank lower for resistance to sterilization.

The conventional methods discussed above used to qualify effective sterilization, deimmunization, or disinfection may only measure the ability of the surrogate organisms to grow after sterilization treatment. However, such conventional methods do not indicate how the surrogate organisms are damaged and/or destroyed resulting in the absence of growth. Conventional surrogate testing methods also require the accurate production, storage, transport and handling of 10 thousand to 100 million pure bacteria spores, proper control of growth medias, extended period of growth of the specific spores and careful protection of all growth materials for environmental contamination to qualify if all the test surrogate organisms were completely eliminated. If any component of the process is not vigorously controlled, the sterilization qualification could give false positive or false negative results. False positive results will trigger extensive effort to unnecessarily repair sterilization equipment as well as the recall of days or weeks of sterilized medical equipment and the patients treated with such equipment. False negative results are worse because they will result in defective sterilization equipment being used and the resulting contaminated medical equipment endangering patients.

For other infectious organisms, such as members of the bacterial genera *Clostridium, Staphylococcus* or fungal genera *Trichophyton* or *Candida*, and the like, specific tests for each genera may be based on similar fundamentals. See Table 2 below for a list of common bacteria and fungus genera and species having an impact on human medicine.

TABLE 2

Common bacteria and fungus genera and species
having an impact on human medicine.

| Genus | Example Species | Health Care Application - Problem pathogen or BL1/sterilization testing organism. |
|---|---|---|
| *Bacillus* | *Bacillus subtilis* | Research organism, used as an "indicator organism" during disinfection testing. BL1. |
| | *Bacillus atrophaeus* | Used as an "indicator organism" during gas (EtO) sterilization procedure. BL1. |
| | *Bacillus pumilis* | Used as an "indicator organism" during radiation sterilization procedure. BL1. |
| | *Geobacillus stearothermophilus* (formerly *B. stearothermophilus*) | Used as an "indicator organism" during steam sterilization procedure. BL1. |
| | *Bacillus anthracis* | Causes anthrax. |
| | *Bacillus cereus* | Causes food poisoning similar to that caused by *Staphylococcus*. |
| *Clostridium* | *Clostridium sporogenes* | Used as a surrogate for *C. botulinum* when testing the efficacy of commercial sterilization. |
| | *Clostridium tetani* | Causes tetanus. |
| | *Clostridium botulinum* | Causes botulism poisoning. |
| | *Clostridium perfringens* | Causes gas gangrene |
| | *Clostridium difficile* | Causes *C. dif* GI infection. |
| | *Clostridium novyi* | Causes a wide range of human and animal infections depending on type. |
| *Mycobacterium* | *Mycobacterium tuberculosis* | Major cause of human tuberculosis. |
| | *Mycobacterium africanum* | Slow growing form of tuberculosis. |
| | *Mycobacterium caprae* | More rare form of human tuberculosis. |
| | *Mycobacterium kansasii* | Chronic human pulmonary disease resembling tuberculosis (involvement of the upper lobe). |
| | *Mycobacterium ulcerans* | Infects the skin and subcutaneous tissues, giving rise to indolent nonulcerated and ulcerated lesions. |
| | *Mycobacterium interjectum* | Chronic lymphadenitis |
| | *Mycobacterium leprae* | Causes leprosy |
| | *Mycobacterium lepromatosis* | Causes leprosy |
| | *Mycobacterium terrae* | Causes serious skin infections that are relatively resistant to antibiotic therapy. Used to study effectiveness of disinfection processes for reusable medical instruments. |
| | *Mycobacterium gastri* | Casual resident of human stomachs, but not considered an etiologic agent of disease. (BL1). |
| *Staphylococcus* | *Staphylococcus aureus* | Causes a variety of infections in the body, including boils, cellulitis, abscesses, wound infections, toxic shock syndrome, pneumonia, and food poisoning. Substrain - Methicillin-resistant *Staphylococcus aureus* (MRSA). Substrain - Vancomycin-resistant *Staphylococcus aureus* (VRSA) - acquired gene from VRE. |
| | *Staphylococcus capitis* | Associated with prosthetic valve endocarditis, forms biofilms. |
| | *Staphylococcus epidermidis* | Hospital-acquired concern as it forms biofilms catheters or other surgical implants. |
| | *Staphylococcus haemolyticus* | Second-most frequently isolated hospital-acquired Infection, often associated with the insertion of medical devices; highly antibiotic-resistant phenotype and able to form biofilms. |

TABLE 2-continued

Common bacteria and fungus genera and species having an impact on human medicine.

| Genus | Example Species | Health Care Application - Problem pathogen or BL1/sterilization testing organism. |
|---|---|---|
| | Staphylococcus lugdunensis | Wide variety of infections including cardiovascular infections, osteomyelitis and prosthetic/native joints infections, skin and soft-tissue infection, central nervous infections, peritonitis, endocephalitis, and urinary tract infections. |
| | Staphylococcus saccharolyticus | May cause of infective endocarditis. |
| | Staphylococcus saprophyticus | Common cause of community-acquired urinary tract infections. |
| | Staphylococcus auricularis | Occasionally can be involved with human skin infections. |
| Salmonella | Salmonella enterica | Causes food poisoning. |
| Enterococcus | Enterococcus faecalis | Can cause endocarditis and septicemia, urinary tract infections, meningitis, and other infections. Substrain - Vancomycin-resistant Enterococcus (VRE). |
| | Enterococcus faecium | Neonatal meningitis or endocarditis. Substrain - Vancomycin-resistant Enterococcus (VRE). |
| | Enterococcus gallinarum | Known to cause outbreaks and spread in hospitals. |
| | Enterococcus hirae | Endocarditis and septicemia in humans. |
| | Enterococcus malodoratus | Frequently the cause of hospital-acquired noscomial infections, bloodstream infections, and urinary tract infections. |
| Escherichia | Escherichia coli | Some serotypes can cause serious food poisoning in their hosts. Substrain K-12 strain commonly used in recombinant DNA work (BL1). Substrain O157:H7 causes serious illness or death in the elderly, the very young, or the immunocompromised. Substrain O104:H4, can trigger major cause of foodborne illness and lead to hemolytic-uremic syndrome (HUS). |
| | Escherichia fergusonii | Known to infect open wounds and may also cause bacteraemia or urinary tract infections; highly resistant to the antibiotic ampicillin and some also resistant to gentamicin and chloramphenicol. |
| Helicobacter | Helicobacter pylori | Cause gastritis and ulcers. |
| | Helicobacter hepaticus | May be associated with Crohn's disease and ulcerative colitis. |
| | Helicobacter bilis | May be associated with Crohn's disease and ulcerative colitis. |
| | Helicobacter ganmani | May be associated with Crohn's disease and ulcerative colitis. |
| Klebsiella | Klebsiella pneumoniae | Causes pneumonia, urinary tract infections, septicemia, meningitis, diarrhea, and soft tissue infections; naturally resistant to many antibiotics. Substrain - CREs - carbapenem-resistant Klebsiella pneumoniae (CRKP). |
| | Klebsiella oxytoca | Cause colitis and sepsis. |
| Neisseria | Neisseria gonorrhoeae | Causes Gonorrhea. |
| | Neisseria meningitidis | Causes meningitis. |

TABLE 2-continued

Common bacteria and fungus genera and species
having an impact on human medicine.

| Genus | Example Species | Health Care Application - Problem pathogen or BL1/sterilization testing organism. |
|---|---|---|
| *Pseudomonas* | *Pseudomonas aeruginosa* | A multidrug resistant pathogen associated with hospital-acquired infections such as ventilator-associated pneumonia and various sepsis syndromes. Common in CF patients. |
| | *Pseudomonas mendocina* | Occasionally causes hospital-acquired infections, such as infective endocarditis and spondylodiscitis. |
| | *Pseudomonas fluorescens* | Produces enzymes that cause milk to spoil and occasionally infects immunocompromised patients. |
| | *Pseudomonas putida* | Used in bioremediation, or the use of microorganisms to biodegrade oil. |
| *Trichophyton* (Fungus) | *Trichophyton rubrum* | Most common cause of athlete's foot, fungal infection of nail, jock itch, and ringworm. |
| | *Trichophyton tonsurans* | Causes ringworm infection of the scalp. |
| | *Trichophyton interdigitale* | One of three common fungi which cause ringworm. |
| | *Trichophyton mentagrophytes* | Causes tinea infections including athlete's foot, ringworm, jock itch, and similar infections of the nail, beard, skin and scalp. |
| | *Trichophyton concentricum* | Associated with the skin infection tinea imbricate. |
| *Candida* (Fungus) | *Candida albicans* | Dimorphic fungus that grows both as yeast and filamentous cells; Responsible for 50-90% of all cases of candidiasis in human. Important causes of morbidity and mortality in immunocompromised patients. Biofilms may form on the surface of implantable medical devices. Cause of 85-95% of vaginal infections cases are responsible for physician office visits every year. |
| | *Candida dubliniensis* | A fungal opportunistic pathogen originally isolated from AIDS patients. It is also occasionally isolated from immunocompetent individuals. |
| | *Candida tropicalis* | Common pathogen in neutropaenic hosts; research suggests that *C. tropicalis*, working synergistically with *Escherichia coli* and *Serratia marcescens*. May cause or contribute to Crohn's disease |
| | *Candida auris* | Causes candidiasis in humans; often acquired in the hospital when human immune systems are weakened; causes fungemia, yielding candidemia (systemic candidiasis); attracted clinical attention because of multidrug resistance. |

Examples of standardized methods for sterilization or disinfection (A) and standardized testing methods protocols (B) used to determine the effectiveness of sterilization or disinfection, as shown in Table 3 below:

TABLE 3

Approved Methods of Sterilization or Disinfection and Qualifying Test Protocols (A) Standard Methods for Preparing Healthcare Equipment

| Disinfection | Sterilization |
| --- | --- |
| Alcohol | Steam Sterilization |
| Chlorine and Chlorine Compounds | Flash Sterilization |
| Formaldehyde | Ethylene Oxide "Gas" Sterilization |
| Glutaraldehyde | Hydrogen Peroxide Gas Plasma |
| Hydrogen Peroxide | Peracetic Acid Sterilization |
| Iodophors | Ionizing Radiation |
| Ortho-phthalaldehyde | Dry-Heat Sterilizers |
| Peracetic Acid | Liquid Chemicals |
| Peracetic Acid and Hydrogen | Performic Acid |
| Peroxide | Filtration |
| Phenolics | Microwave |
| Quaternary Ammonium Compounds | Glass Bead "Sterilizer" |
| Radiation | Vaporized Hydrogen Peroxide |
| Pasteurization | Ozone |
| Flushing- and Washer-Disinfectors | Formaldehyde |
|  | Gaseous Chlorine Dioxide |
|  | Vaporized Peracetic Acid |
|  | Infrared radiation |

(B) Standard Test to Qualtify Healthcare Equipment

| Test Name | Example Test Species |
| --- | --- |
| BI (ethylene oxide (EtO) sterilization) | B. atrophaeus |
| BI (gamma radiation sterilization) | B. pumilis |
| BI (steam sterilization) | G. stearothermophilus |
| AOAC Sporicidal Efficacy Test Method | Clostridium sporogenes Bacillus subtilis |
| AOAC Tuberculosis Rate of Kill | Mycobacterium terrae |
| AOAC Use Dilution Test | Pseudomonas aeruginosa Staphylococcus aureus Salmonella enterica |
| AOAC Fungicidal Efficacy Test Method | Trichophyton mentagrophytes |

For each standard test protocol, a define number of organisms are placed on a carrier, such as tube, filter paper, or coated on and in a test solid surface. The specific organisms may be a particular infectious species or could be a surrogate species of the same genus that is closely related to the infectious species. In all cases, the species, carrier and growth conditions are defined by the FDA and/or the Association of Analytical Communities (AOAC) protocol. Following treatment with sterilization or disinfection equipment, the carrier with the specific species sample is placed into ideal growing conditions for the particular test species. After a required period in culture, usually 2 to 30 days, the culture is monitored. If no growth is observed, the sterilization or disinfection equipment is declared to be operating within required parameters.

In addition to enabling growth and infectivity, protein components of infectious organisms could trigger severe immunogenic or allergic reactions in susceptible individuals even at very low level. Examples include mold proteins that are able to trigger severe allergic reactions even if the mold has been rendered no longer able to grow. Immunogenic proteins can also occur in food such as gliadin, a highly immunogenic protein component of the seed storage protein gluten in wheat and related grains. Gliadin can trigger reactions in most individuals suffering from Crohn's disease. It is critical that immunogenic proteins are completely removed from any equipment that will be used in conjunction with susceptible individuals.

A wide range of pathogenic organisms use a multicopper oxidase with 3 cupredoxin superfamily domains for growth and survival. As disclosed herein, the loci suf I that contains a critical protein that confers different functions depending on the genus (bacteria or fungus) and this critical protein can be targeted. Depending on the genus, the suf I loci encoded protein can have different names. The functions of the protein encoded by suf I include cell division (FtsP), formation of spore coat proteins (CotA), chromosome partitioning, inorganic ion transport, and metabolism and cell wall, membrane, and envelope formation. As the protein product of the suf I loci are absolutely critical for the survival of the spores (in spore forming bacteria) and/or growth (all bacteria and fungus), if the protein product of the suf I loci is irreversibly fragmented into short polypeptides and amino acids, the bacteria or fungus cannot survive. Additionally, it is likely that a sterilization method that clearly demonstrates fragmentation of the protein product of the sufi I loci would also fragment other proteins in the bacterium or fungus. Bacteria and fungus can be divided into distinct genus each containing multiple species. Many species also have subspecies that carry unique characteristics include multi-drug resistance. In human health situations, certain bacteria and fungus species and subspecies are of major concern because they are capable of causing disease. Related species may be used in medical research, e.g., E. coli K12, or as indicator species for qualification of sterilization, e.g., B. atrophaeus used to qualify gas sterilization. See Table 2 above for a list of common bacteria and fungus genera and species with impact on human medicine.

Prions are a unique category of a transmissible infectious agent that comprised only of protein, without DNA or RNA. Prions can cause a wide range of neurodegenerative diseases known as transmissible spongiform encephalopathies (TSE) or prion diseases including the new variant Creutzfeldt-Jakob disease (nvCJD). See Table 4 below. Infectious prions are in fact an abnormally folded brain protein. This brain protein (Protease resistant Proteins, PrP) can be folded into two different structural (tertiary) forms, the normal brain protein, $PrP_c$, and the abnormal, disease triggering form, $PrP_{sc}$. The disease triggering form, $PrP_{sc}$, is found in high quantity in the brain of infected humans and animals and can be transferred to a new host with the transfer of infected material. Once in the new host, the abnormally folded protein ($PrP_{sc}$) causes disease symptoms by promoting the unfolding of the normal host protein ($PrP_c$) and refolding into the disease causing form ($PrP_{sc}$). PrP proteins can also be partially cleave and still retain their infectious characteristics. Full length mature PrP protein (both $PrP_c$ and $PrP_{sc}$) is 209 amino acids long. Limited proteolysis of $PrP_{sc}$ will cleave amino acids from the amino terminus resulting in another infectious protein form PrP 27-30 that is approximately 142 amino acids long. Additional cleavage that significantly reduces the 142 amino acid long PrP 27-30 is needed to render the PrP protein irreversibly non-infectious. Although most infectious agents can be permanently rendered non-infectious by heat or steam, these methods are not sufficient to eliminate infectious prions from medical equipment.

TABLE 4

Example of Prion Diseases in Different Species and Potential Origin of the Infectious Protein.

| Disease | Species | Potential Origin | Disease | Species | Potential Origin |
|---|---|---|---|---|---|
| Creutzfeldt-Jakob disease (CJD) | Human | Inherited | Scrapie | Sheep and Goat | Inherited/environmental |
| New Variant Creutzfeldt-Jakob disease (CJD) | Human | Consumption, Medical Contamination | Bovine Spongiform Encephalopathy (BSE) | Cattle | Consumption |
| Fatal Familial Insomnia (FFI) | Human | Inherited | Transmissible Mink Encephalopathy (TME) | Mink | Environmental |
| Gerstmann-Straussler disease (GSD) | Human | Inherited | Chronic Wasting Disease (CWD) | Mule Deer and Elk | Environmental |
| Huntington disease-like type 1 (HDL1) | Human | Inherited | Feline Spongiform Encephalopathy (FSE) | Cats | Consumption |
| Kuru | Human | Consumption of Human Brains | Exotic Ungulate Encephalopathy (EUE) | Nyala and Greater Kudu | Environmental |

As discussed above, prions are abnormally folded protease resistant proteins ($PrP_{sc}$) that cause disease symptoms by promoting the unfolding of normal proteins ($PrP_c$) and refolding into the disease causing protein form ($PrP_{sc}$). As the level of the $PrP_{sc}$ rises in the patient's brain, symptoms of progressive dementia, myoclonic seizures, abnormalities of high cortical function, cerebellar and corticospinal disturbances develop. The period between infection and development of disease can extend for years to decades. The duration of disease symptoms is variable but is typically 8 to 18 months.

Once prion proteins fold into the infectious form ($PrP_{sc}$), they are extremely difficult to render non-infectious. Conventional methods to sterilize medical equipment contaminated with prions, such as high heat to promote loss of function of other protein types by triggering loss of tertiary structure, are ineffective because unlike most proteins, the denatured prion proteins, both infectious and non-infectious, will spontaneously refold by themselves back to their pre-treatment forms. In some cases, conventional methods may actually result in refolded into infectious form promoting the conversion of the non-infection prion protein into the infectious prion protein.

To render infectious proteins such as prions irreversibly non-infectious, all infectious proteins must be fragmented into small polypeptides, amino acids or components. The only currently approved conventional method for this process is harsh treatment of medical equipment and supplies with caustic soda, an extremely harsh process that frequently damages and/or destroys medical equipment.

Determining whether or not an infectious prion ($PrP_{sc}$) sample has been permanently destroyed can be extremely difficult and time consuming. Conventional methods for determining whether an infectious prion has been permanently destroyed require that after attempted deactivation, the $PrP_{sc}$ sample is injected into a matched susceptible animal that is then followed for an extended time to see if the animal develops disease. In larger animals, the process can take years, but even in a small animal such as a mouse, the test can take months. As there is a potential for inter-animal variation and poor test accuracy, a large animal test pool is required to obtain relatively accurate results.

Immunogens may include a wide range of molecules including proteins that can trigger dramatic immunologic responses in susceptible individuals. The responses can trigger serious allergic reactions on the skin (e.g., poison ivy rash), in the gut (e.g., triggering a flare-up in Crohn's disease), in the lung (e.g., asthma) or a systemic response (e.g., anaphylaxis). Protein immunogens are a special class of immunogens produced by a wide range of bacteria, fungus (e.g. mold) or plants and can be difficult to destroy. An example of a common plant immunogen is gluten. Common grains such as various strains of wheat, farro, rye and spelt are derived from wild and domesticated grains of the *Triticum, Aegilops* and *Secale* genera. Common to all these species is the seed storage protein complex called gluten. When seeds are ground into flour, the gluten protein complex gives bread dough its elastic quality and bread its spongy texture. Unfortunately gluten is comprised of several proteins including Gliadin (also called Prolamin) which triggers severe T cell attack on the gut of patients with the autoimmune disease Celiac disease (CD). Gliadins can be typed as α, γ, and ω with a small protease resistant fragment (p57-73) of α-gliadins triggering the most severe destructive T cell response. As a results CD patients must not only avoid products containing gluten, but also need to be extremely careful to avoid small amounts of residual α-gliadin that may contaminate food preparation utensils.

Protease resistant proteins like α-gliadin are resistant to destruction so it is critical that devices and methods used to destroy them and other immunogens (also called allergens) can be easily checked to ensure they are operating at peak efficiency. If not, residual allergens can trigger life threatening responses in sensitive patients. The process of removing immunogens by deimmunization methods or devices is called deimmunization. The ability to test for the destruction of different immunogens on surfaces is not standardized. Usually affected patients are subjected to skin test regiments to determine their individual reactions to different candidate immunogens/allergens. The patient is then advised to avoid all immunogen contact and discard any materials potential contaminated with the specific immunogen or allergen. In cooking and manufacturing situations, extreme care must be taken to avoid potential cross contamination to the point that food packaging labels frequently carry warning labels about the potential issues.

Thus, a method is needed to determine irreversible destruction of proteins critical for the growth of infectious organisms, immunogenic proteins, and/or infectious proteins (e.g., prions) and thus rapidly and accurately determines the effectiveness of sterilization, deimmunization, and/or disinfection of equipment or supplies by a device.

With such a method for rapidly determining effective sterilization, deimmunization, and/or disinfection, medical personnel and patients can have confidence that the medical equipment used for patient treatment is not contaminated with potentially lethal or immunogenic proteins. Without such a method, medical personnel may believe they are using properly sterilized equipment and then later discover that they have accidentally exposed their patients to lethal infections and harmful immune reactions

SUMMARY OF THE INVENTION

In one aspect, a method for rapidly determining effective sterilization, deimmunization, and/or disinfection of equipment and/or supplies by a device is featured. The method includes providing a defined surrogate protein having a predetermined sequence representative of an infectious agent potentially contaminating the equipment and/or the supplies to be sterilized, deimmunized, and/or disinfected by the device. The defined surrogate protein having the predetermined sequence is subjected to sterilization, deimmunization, or disinfection. The effectiveness of the sterilization, deimmunization, or disinfection is rapidly determined by determining if the defined surrogate protein having the predetermined sequence has been destroyed.

In one embodiment, the defined surrogate protein may include proteins critical for stability, growth and/or infectious capacity of infectious agents. The defined surrogate protein may include a protein critical for stability, growth and/or infectious capacity of surrogate organisms of infectious agents. The infectious agent may include one or more of: an infectious protein, an infectious spore forming bacteria, an infectious vegetative bacteria, an infectious fungus, and an infectious virus. The defined surrogate protein may include pathogenic proteins, proteins critical for the growth of infectious agents, and immunogenic proteins. The predetermined sequence may be defined by the sequence:

```
                                                    (SEQ ID NO: 1)
         10          20          30          40          50
   MYNYTSAKYE  VPIAIQDRSF  NEDGSLNFPS  EGDNPTIHPY  WQPEFFGDTI

MVNGRVWPNM  NVDMTRYRFR  LLNGSNARFY  NLKFSNGMQF  WQIGTDGGYL

NKPVPLTSLL  ISPGERADIL  VDFTEIPAGT  RIILNNDANA  PYPTGDAPDK

DTTGQIMQFT  VQHNDHHHHH  H
```

The defined surrogate protein for SEQ ID NO: 1 may be at least 95% homologous the predetermined sequence or substantial fragment of the predetermined sequence. The predetermined sequence may be defined by the sequence:

```
                                                    (SEQ ID NO: 2)
         10          20          30          40          50
   MTLEKTYYEV  TMEECTHQLH  RDLPPTRLWG  YNGLFPGPTI  EVKRNENVYV

KWMNNLPSTH  FLPIDHTIHH  SDSQHEEPEV  KTVVHLHGGV  TPDDSDGYPE

AWFSKDFEQT  GPYFKREVYH  YPNQQRGAIL  WYHDHAMALT  RLNVYAGLVG

AYIIHDPKEK  RLKHHHHHH
```

The defined surrogate protein for SEQ ID NO: 2 may be at least 95% homologous to the predetermined sequence or substantial fragment of the predetermined sequence. The predetermined sequence may be defined by the sequence:

```
                                                    (SEQ ID NO: 3)
         10          20          30          40          50
   MTGMPEGEGV  DSNLLGGDGG  DIAYPYYLIN  GRIPVAATSF  KAKPGQRIRI

RIINSAADTA  FRIALAGHSM  TVTHTDGYPV  IPTEVDALLI  GMAERYDVMV

TAAGGVFPLV  ALAEGKNALA  RALLSTGAGS  PPDHHHHHH
```

The defined surrogate protein for SEQ ID NO: 3 may be at least 95% homologous to the predetermined sequence or substantial fragment of the predetermined sequence.

The predetermined sequence may be defined by the sequence:

```
                                                    (SEQ ID NO: 4)
         10          20          30          40          50
   MTGYKNYTLK  AQKGKTEFYK  NNFSNTLGYN  GNLLGPTLKL  KKGDKVKIKL

INNLDENTTF  HWHGLEVNGK  VDGGPSQVIK  PGKEKTIKFE  VNQDSATLWY

HPHPSPNTAK  QVYNGLSGLL  YIEDSKKNHH  HHHH
```

The defined surrogate protein SEQ ID NO: 4 may be at least 95% homologous to the predetermined sequence or substantial fragment of the predetermined sequence.

The predetermined sequence may be defined by the sequence:

```
                                                  (SEQ ID NO: 5)
         10         20         30         40         50
MTGFRHEKVL CLKTWHVDEQ GAFTPFSVPR QAAREGTRGR YSTINGKHVP

TIDLPAGQIV RVRLLNVDNT VTYRLNPNGE ARIYANDGHP VEPRGFEGQY

WIGPGMRLEL ALKVPEAGTE LSLRDGPVRL ATIRSVAHHH HHH
```

The defined surrogate protein SEQ ID NO: 5 may be at least 95% homologous to the predetermined sequence or substantial fragment of the predetermined sequence. The predetermined sequence may be defined by the sequence:

```
                                                  (SEQ ID NO: 6)
         10         20         30         40         50
MTITLEWSVT TGYRRLDGVK KRVYLINGLF PGPTIEARSG DSLQVQVTNN

IQDEGLVIHW HGLHMRGANH MDGVTGVTQC PIVPGDSMLY NFTISQSQSG

TFWYHAHSAL QRAEGLYGGF VVHKPSTHHH HHH
```

The defined surrogate protein SEQ ID NO: 6 may be at least 95% homologous to the predetermined sequence or substantial fragment of the predetermined sequence. The predetermined sequence may be defined by the sequence:

```
                                                  (SEQ ID NO: 7)
         10         20         30         40         50
MTAETHTWYF KTSWVDANPD GVFPPRKMIGF NDSWPLPTLR VKKGDTVNLY

LINGFDDRNT SLHFHGLFQH GTNQMDGPEM VTQCPIPPGE TFLYNFTVDD

QVGSYWYHSH TSGQYGDGMR GVFIIEDHHH HHH
```

The defined surrogate protein SEQ ID NO: 7 may be at least 95% homologous to the predetermined sequence or substantial fragment of the predetermined sequence. The predetermined sequence may be defined by the sequence:

```
                                                  (SEQ ID NO: 8)
         10         20         30         40         50
MKTVRVPVPQ PQPQNPSQPQ PQRQVPLVQQ QQFPGQQQQP PPQQPYPQPQ

PFPSQQPYLQ LQPFPQPQPF PPQLPYHHHH HH
```

The defined surrogate protein SEQ ID NO: 8 may be at least 95% homologous to the predetermined sequence or substantial fragment of the predetermined sequence. The rapidly determining may include a sensitive protein analysis procedure. The sensitive protein analysis procedure may include one or more of: a Western Blot analysis, a protein assay analysis, a magnetic separation analysis, a peptide analysis, a mass spectrometry analysis, and a gas chromatography analysis. The sensitive protein analysis procedure may include fluorescence analysis of proteins covalently crosslinked on a solid surface. The sensitive protein analysis procedure may include fluorescence analysis of proteins covalently crosslinked on magnetic beads. The defined surrogate protein having the predetermined sequence may be disposed on a surface, disposed on a test strip, disposed in or on a vessel, on a tube, or in or on a holder. The holder may be disposed to receive a flow of a sterilization agent, a deimmunization agent or a disinfection agent.

BRIEF DESCRIPTION OF THE SEVERAL VIEWS OF THE DRAWINGS

Other objects, features and advantages will occur to those skilled in the art from the following description of a preferred embodiment and the accompanying drawings, in which:

FIG. 4 shows an example of an amino acid comparison of human PrP proteins with a selection of other species of PrP proteins;

FIG. 7 is a homology diagram comparing protein sequences of a research *Clostridium* species and two pathogenic *Clostridium* species;

FIG. 8 shows an example of a Western Blot for a defined *Clostridium* surrogate protein having a predetermined sequence that has been subjected to sterilization, deimmunization, or disinfection;

DETAILED DESCRIPTION OF THE INVENTION

Figure 1:
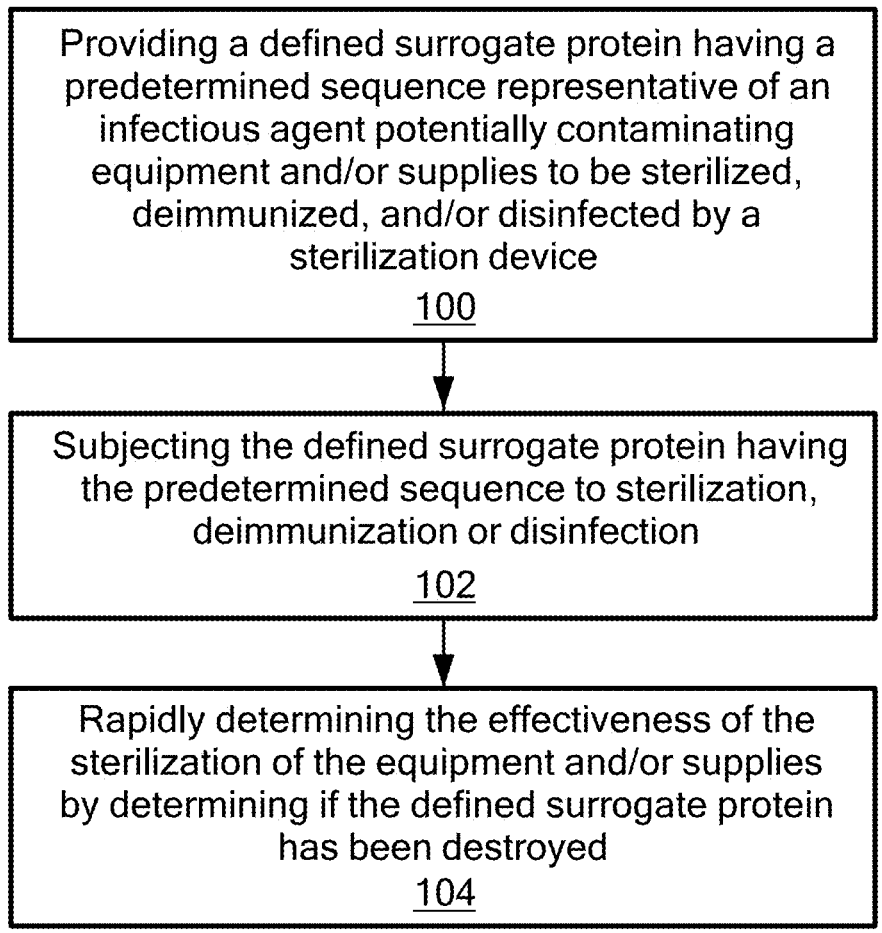
FIG. 1 is a schematic block diagram showing the primary steps of one embodiment of the method for rapidly determining effective sterilization, deimmunization, and/or disinfection of this invention.
Figure 2:
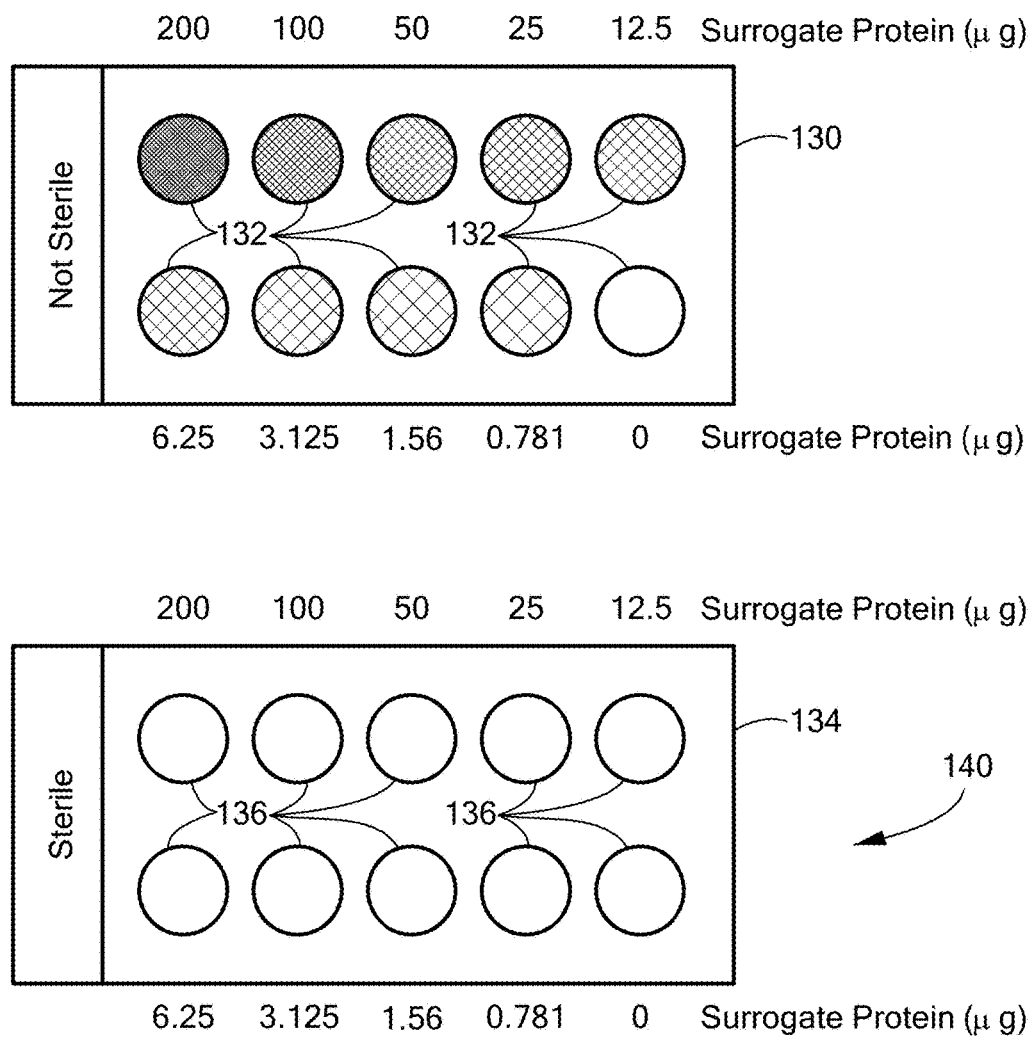
FIG. 2 is a schematic diagram showing examples of multi-well glass slides having samples of one or more of the defined surrogate protein having a predetermined sequence in wells which are subjected to sterilization, deimmunization, or disinfection to provide a visual depiction of the effectiveness of sterilization, deimmunization, and/or disinfection.
Figure 3:
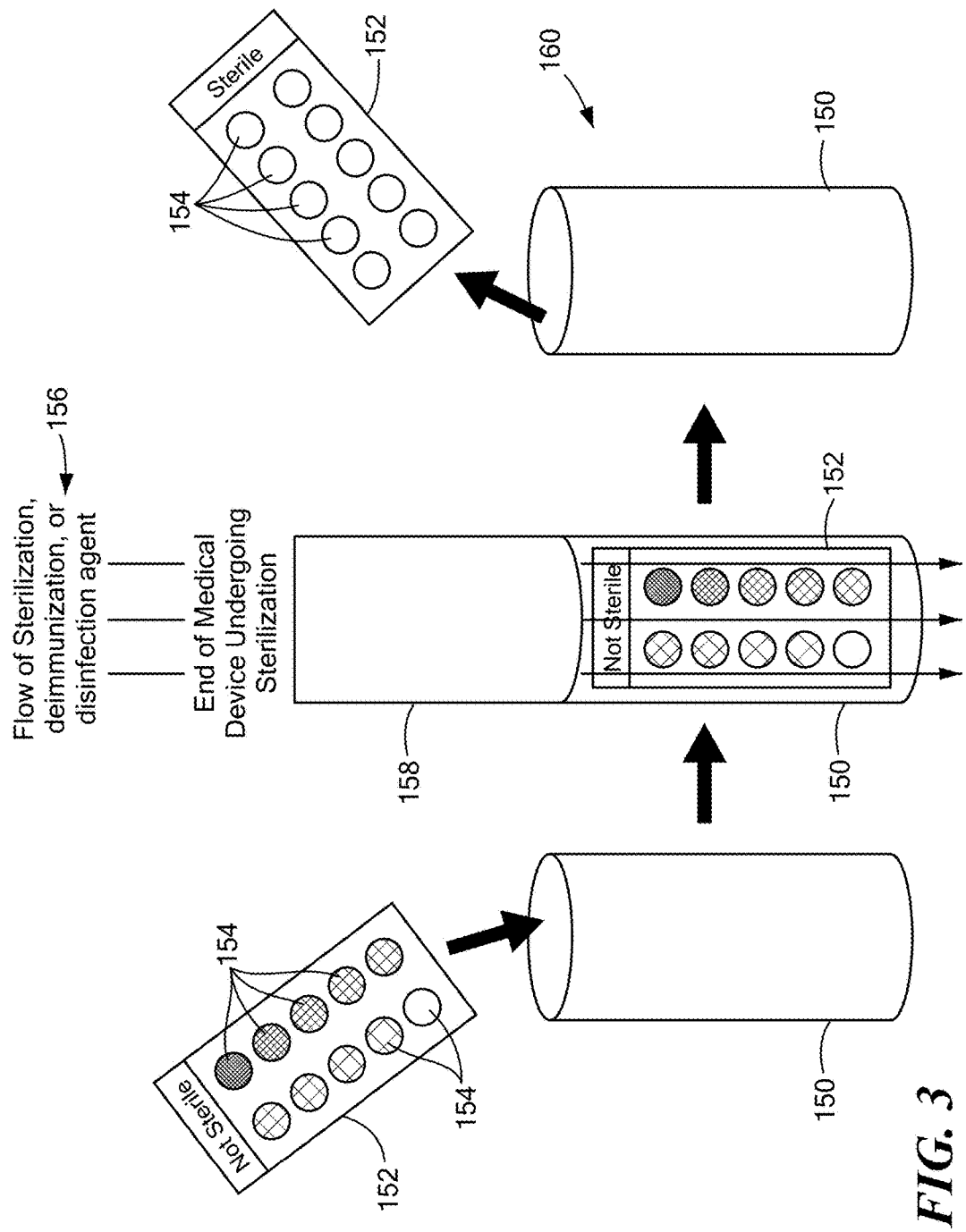
FIG. 3 is a schematic block diagram showing one example of the multi-well glass slides shown in FIG. 2 placed in a holder disposed at the end of a flow of sterilization, deimmunization, or disinfection agent in accordance with one embodiment of this invention.

Aside from the preferred embodiment or embodiments disclosed below, this invention is capable of other embodiments and of being practiced or being carried out in various ways. Thus, it is to be understood that the invention is not limited in its application to the details of construction and the arrangements of components set forth in the following description or illustrated in the drawings. If only one embodiment is described herein, the claims hereof are not to be limited to that embodiment. Moreover, the claims hereof are not to be read restrictively unless there is clear and convincing evidence manifesting a certain exclusion, restriction, or disclaimer.

The method for rapidly determining effective sterilization, deimmunization, and/or disinfection of equipment or supplies of one or more embodiments of this invention may be utilized to qualify sterilization, deimmunization, and/or disinfection by a device, e.g., a sterilization device, a deimmunization device, or a disinfection device and provide improvements to the conventional methods discussed above. In one example, the method for rapidly detecting effective sterilization, deimmunization, and/or disinfection of equipment or supplies of one or more embodiments of this invention may be based on a specific measuring the complete destruction of a specific protein critical for an organism's growth and requires only a few hours to return absolute results. The method for rapidly detecting effective sterilization, deimmunization, and/or disinfection of equipment or supplies of one or more embodiments of this invention also contains multiple layers of internal controls that enable a clear determination if either false positive and false negative results have occurred. This allows the avoidance of unnecessary repairs to sterilization, deimmunization, or disinfection equipment and eliminates false negative tests and more dangerous exposure of patients to improperly sterilized, deimmunized, or disinfected medical equipment or supplies.

The method for rapidly detecting effective sterilization, deimmunization, and/or disinfection of equipment or supplies of one or more embodiments of this invention may be used to rapidly determine if a sterilization, deimmunization, and/or disinfection device is effectively destroying specific infectious or immunogenic agents, defined herein as infectious or pathogenic proteins, infectious spore forming bacteria, infectious vegetative bacteria, infectious fungus, infectious viruses, and immunogenic proteins.

In one embodiment, the method for rapidly determining effective sterilization, deimmunization and/or disinfection of equipment and/or supplies by a device, such as a sterilization device, e.g., by a device that applies cycles of a solvent and electromagnetic radiation, e.g., microwaves, such as disclosed in U.S. application Ser. No. 15/330,469 by the assignee hereof, hereinafter the '469 patent application, any of the sterilization devices discussed in the Background section above, the devices for the methods of sterilization shown in Table 3 above, an autoclave, of similar type sterilization device known to those skilled in the art, a deimmunization device, e.g., a device that applies cycles of a solvent and electromagnetic radiation, e.g., microwaves, such as disclosed in the '469 patent application and/or disinfection device, e.g., a device that applies cycles of a solvent and electromagnetic radiation, e.g., microwaves, such as disclosed in the '469 patent application, or the devices for the methods of disinfection shown in Table 3 above, includes providing a defined surrogate protein having a predetermined sequence representative of an infectious agent potentially contaminating the equipment and/or supplies to be sterilized, deimmunized and/or disinfected by the device, step 100, FIG. 1. The defined surrogate protein having the predetermined sequence is then subjected to sterilization, deimmunization, or disinfection, step 102. The effectiveness of the sterilization, deimmunization, and/or disinfection by the device is then rapidly determined by determining if the defined surrogate protein having the predetermined sequence has been destroyed, step 106, as discussed further below.

The method preferably directly measures the irreversible destruction of the defined surrogate proteins having the predetermined sequence that are critical for survival and/or growth of such infectious agents.

In one embodiment, the method utilizes one or more prion detection indicator samples configured as a defined surrogate protein. In this example, the defined surrogate protein has the following predetermined sequence:

```
                                                 (SEQ ID No: 9)
KKRPKPGGWN TGGSRYPGQG SPGGNRYPPQ GGTWGQPHGG GWGQPHGGSW      50

GQPHGGSWGQ PHGGGWGQGG GTHNQWNKPS KPKTNLKHVA GAAAAGAVVG    100

GLGGYMLGSA MSRPMIHFGN DWEDRYYREN MYRYPNQVYY RPVDQYSNQN    150

NFVHDCVNIT IKQHTVTTTT KGENFTETDV KMMERVVEQM CVTQYQKESQ    200

AYYDGRRS                                                  208
```

The defined prion surrogate protein having the predetermined sequence above for prion detection is then subjected to sterilization, deimmunization, or disinfection, by a device, e.g., a sterilization device, a deimmunization device or a disinfection device, e.g., by conventional methods discussed in the Background section above, or by applying cycles of a solvent and electromagnetic radiation, e.g., microwaves, such as disclosed in the '469 patent application.

In this example, to rapidly determine the effectiveness of sterilization, deimmunization, or disinfection of equipment or supplies by the device, a determination is made if the defined surrogate protein has been destroyed using a sensitive protein analysis procedure, such as Western Blot analysis, or similar protein analysis techniques, such as fluorescence analysis of proteins covalently crosslinked to solid surfaces used in protein array analysis which are extremely sensitive processes that measure both the amount of full length intact defined surrogate protein having a predetermined sequence and the amount of the destroyed or degraded defined surrogate protein, protein array analysis, magnetic separation analysis, peptide analysis, mass spectrometry analysis, gas chromatography analysis, or similar type analysis. In one example, the defined surrogate protein includes a protein critical for stability, growth, and/or infectious capacity of an infectious agent. The defined surrogate protein may include a protein critical for stability, growth, and/or infectious capacity of a surrogate organism of the infectious agent.

One embodiment of the method for rapidly detecting effective sterilization, deimmunization, and/or disinfection of this invention includes providing the defined surrogate protein having a predetermined sequence that is based on the development of a synthetic recombinant test protein sequence with high homology to a section of a protein encoded by the suf I loci in the targeted pathogenic genus, e.g., one or more or all of the genus shown in Table 2 above, and the development of a monoclonal or polyclonal antibody that is able to detect the defined surrogate recombinant protein using Western Blot or other similar protein analysis techniques discussed above. In genera that form spores, such as *Bacillus* and *Clostridium*, the target protein encoded in the suf I loci or defined surrogate protein having the predetermined sequence of the tests forms the spore coat protein CotA. In non-spore forming genus such as the bacteria *Mycobacterium, Staphylococcus* and *Pseudomonas*, or the fungus *Candida*, the target protein encoded in the suf I loci or defied surrogate protein of the tests forms the cell division protein (FtsP). In other genera of bacteria and fungus, the target protein or encoded defined surrogate protein having the predetermined sequence in the suf I loci may have additional names but all carry the same protein structure of multicopper oxidase with 3 cupredoxin superfamily domains.

For each method of rapidly determining effective sterilization, deimmunization, or disinfection, specific for its unique genus, a predetermined quantity of the defined surrogate having the predetermined protein sequence is placed on a carrier, such as filter paper, or a tube, or on the surface of an object, such as a glass or slide, a microtiter plate, a flexible membrane, magnetic beads, e.g., magnetic beads used for magnetic bead separation or similar type object or surface. For Western analysis, the defined surrogate protein having the predetermined sequence is not covalently linked to the carrier or surface. In other protein analysis processes such as protein array or magnetic bead separation, the defined surrogate protein having the predetermined sequence is covalently linked to the carrier or solid surface. After treatment with the sterilization, deimmunization or disinfection equipment of process and Western analysis, this involves recovering the recombinant defined surrogate protein having the predetermined sequence, both in its intact and fragmented forms, from the carrier, surface tube, or object, treating the sample with denaturing loading buffer and running the sample on an acrylamide gel. A control sample that was not subjected to sterilization, deimmunization, or disinfection is also included. In one example, the samples are transferred nylon membrane and the intact and fragmented samples are visualized using the specific antibody. If the sterilization, deimmunizing or disinfection equipment is operating correctly, the control sample will have protein indicator bands that are easily visualized but the treated sample will be absent any type protein indicator bands indicating the sterilization, deimmunizing or disinfection equipment was able to irreversibly fragment the recombinant defined surrogate protein. If other protein analysis processes such as protein array or magnetic bead separation are used, the solid surface to which defined surrogate protein having the predetermined sequence was covalently linked will be tested such that intact defined surrogate protein having the predetermined sequence can be visualized using the specific antibody and fragment and/or destroyed defined surrogate protein having the predetermined sequence is no longer detected by the process. As the amino acid sequence and structure of the defined surrogate protein having a predetermined sequence is highly homologous to the target protein in the pathogenic members of the genus, irreversible destruction of the defined surrogate protein indicates that the sterilization, deimmunizing or disinfection equipment will have also destroyed the target proteins, resulting in destruction of all members of the genus that may be on the sterilization, deimmunizing or disinfection equipment or supplies.

In accordance with one or more embodiments of the method for rapidly determining effective sterilization, deimmunization, and/or disinfection, the predetermined sequence of the defined surrogate protein and the corresponding peptide used for development of a polyclonal antibody for Western Blot analysis include one or more of the following predetermined sequences:

For *Clostridium*:

```
                                              (SEQ ID NO: 1)
         10        20        30        40        50
MYNYTSAKYE VPIAIQDRSF NEDGSLNFPS EGDNPTIHPY WQPEFFGDTI

MVNGRVWPNM NVDMTRYRFR LLNGSNARFY NLKFSNGMQF WQIGTDGGYL

NKPVPLTSLL ISPGERADIL VDFTEIPAGT RIILNNDANA PYPTGDAPDK

DTTGQIMQFT VQHNDHHHHH H
```

The peptides used for the development of polyclonal and monoclonal antibodies for use by Western Blot analysis for the above sequence are:

```
                         (SEQ ID NO: 10)
         KYEVPIAIQDRSFNEDGSLNFPSE
         and (SEQ ID NO: 11)
         YLNKPVPLTSLLISPGERADILVD
```

For *Bacillus*:

```
                                              (SEQ ID NO: 2)
         10        20        30        40        50
MTLEKTYYEV TMEECTHQLH RDLPPTRLWG YNGLFPGPTI EVKRNENVYV

KWMNNLPSTH FLPIDHTIHH SDSQHEEPEV KTVVHLHGGV TPDDSDGYPE

ANFSKDFEQT GPYFKREVYH YPNQQRGAIL WYHDHAMALT RLNVYAGLVG

AYIIHDPKEK RLKHHHHHH
```

The peptides used for the development of polyclonal mid monoclonal antibodies for use by Western Blot analysis for the above sequence are:

```
                         (SEQ ID NO: 12)
         QRGAILWYHDHAMALTRLNVYAGL
         and (SEQ ID NO: 13)
         QLHRDLPPTRLWGYNGLFPGPTIE
```

For *Mycobacterium*:

```
                                              (SEQ ID NO: 3)
         10        20        30        40        50
MTGMPEGEGV DSNLLGGDGG DIAYPYYLIN GRIPVAATSF KAKPGQRIRI

RIINSAADTA FRIALAGHSM TVTHTDGYPV IPTEVDALLI GMAERYDVMV

TAAGGVFPLV ALAEGKNALA RALLSTGAGS PPDHHHHHH
```

The peptides used for the development of polyclonal and monoclonal antibodies for use by Western Blot analysis for the above sequence are:

```
                         (SEQ ID NO: 14)
         DTAFRIALAGHSMTVTHTDGYPVIPTEVD
         and (SEQ ID NO: 15)
         VFPLVALAEGKNALARALLSTGAGS
```

For *Staphylococcus*:

(SEQ ID NO: 4)
```
        10          20          30          40          50
MTGYKNYTLK  AQKGKTEFYK  NNFSNTLGYN  GNLLGPTLKL  KKGDKVKIKL

INNLDENTTF  HWHGLEVNGK  VDGGPSQVIK  PGKEKTIKFE  VNQDSATLWY

HPHPSPNTAK  QVYNGLSGLL  YIEDSKKNHH  HHHH
```

The peptides used for the development of polyclonal and monoclonal antibodies for use by Western Blot analysis for the above sequence are:

(SEQ ID NO: 16)
```
    NFSNTLGYNGNLLGPTLKLKKGDKVKIKL
    and
```

(SEQ ID NO: 17)
```
    KFEVNQDSATLWYHPHPSPNTAK
```

For *Pseudomonas*:

(SEQ ID NO: 5)
```
        10          20          30          40          50
MTGFRHEKVL  CLKTWHVDEQ  GAFTPFSVPR  QAAREGTRGR  YSTINGKHVP

TIDLPAGQIV  RVRLLNVDNT  VTYRLNPNGE  ARIYAVDGHP  VEPRGFEGQY

WIGPGMRLEL  ALKVPEAGTE  LSLRDGPVRL  ATIRSVAHHH  HHH
```

The peptides used for the development of polyclonal and monoclonal antibodies for use by Western Blot analysis for the above sequence are:

(SEQ ID NO: 18)
```
    DLPAGQIVRVRLLNVDNTVTYRLN
    and
```

(SEQ ID NO: 19)
```
    QYWIGPGMRLELALKVPEAG
```

For *Trichophyton*:

(SEQ ID NO: 6)
```
        10          20          30          40          50
MTITLEWSVT  TGYRRLDGVK  KRVYLINGLF  PGPTIEARSG  DSLQVQVTNN

IQDEGLVIHW  HGLHMRGANH  MDGVTGVTQC  PIVPGDSMLY  NFTISQSQSG

TFWYHAHSAL  QRAEGLYGGF  VVHKPSTHHH  HHH
```

The peptides used for the development of polyclonal and monoclonal antibodies for use by Western Blot analysis for the above sequence are:

(SEQ ID NO: 20)
```
    YRRLDGVKKRVYLINGLFPGPTIE
    and
```

(SEQ ID NO: 21)
```
    TQCPIVPGDSMLYNFTISQSQSG
```

For *Candida*:

```
              10         20         30         40         50
                                                  (SEQ ID NO: 7)
      MTAETHTWYF KTSWVDANPD GVFPRKMIGF NDSWPLPTLR VKKGDTVNLY

LINGFDDRNT SLHFHGLFQH GTNQMDGPEM VTQCPIPPGE TFLYNFTVDD

QVGSYWYHSH TSGQYGDGMR GVFIIEDHHH HHH
```

The peptides used for the development of polyclonal and monoclonal antibodies for use by Western Blot analysis for the above sequence are:

```
                                           (SEQ ID NO: 22)
              GFNDSWPLPTLRVKKGDTVNLYL
      and
                                           (SEQ ID NO: 23)
              WYFKTSWVDANPDGVFPRKMIG
```

For α-Gliadin:

```
              10         20         30         40         50
                                                  (SEQ ID NO: 8)
      MKTVRVPVPQ PQPQNPSQPQ PQRQVPLVQQ QQFPGQQQQF PPQQPYPQPQ

PFPSQQPYLQ LQPFPQPQPF PPQLPYHHHH HH
```

The peptide used for the development of monoclonal or polyclonal antibody used by Western Blot analysis for the above sequence is:

```
                                           (SEQ ID NO: 24)
              FPPQQPYPQPQPFPSQQPYLQLQPFPQPQ
```

Western Blot analysis typically utilizes equipment, e.g., acrylamide gel, a power supply to create an electric field to trigger protein migration where smaller fragments move faster than larger fragments to separate intact proteins from fragmented or degraded proteins, a membrane, transfer equipment, and visualization equipment. Western Blot analysis also preferably utilizes specific reagents, e.g., a positive control protein to show the location of a full length defined surrogate protein and specific antibody for the defined surrogate protein, e.g., any of the defined surrogate proteins having the associated predetermined sequences and the corresponding antibody above. The specific antibody binds to the associated defined surrogate protein, both full length, and fragments, to provide a visualization if the defined surrogate protein was destroyed by sterilization, deimmunization, or disinfection.

Western Blot analysis for infectious organisms may also typically include a defined number of colony forming units (CFU) or spores of the test pathogen which are added to a stable substrate such as filter paper (dried) or other sample holder. The number of CFU or spores will contain a defined quantity of each indication protein to be followed.

Western Blot analysis may also be conducted on defined surrogate proteins having the associated predetermined sequences samples placed on indicator strips or other small sample holders that maybe subjected to sterilization, deimmunization or disinfection. After sterilization, deimmunization or disinfection, the defined surrogate proteins from the indicator strips or other small sample holders are extracted from the filter paper or other sample holders into a loading dye and denatured (eliminating any tertiary protein structure). The samples are then run on the gel, including control wells with (1) size marker, (2) positive control protein, (3) other controls if needed. After transfer to membrane, defined surrogate proteins and protein fragments are visualized with unique antibodies preferably having a high affinity and specific binding to an indicator region of the protein being tested. Successful sterilization, deimmunization or disinfection will result in the loss of all indicator proteins of defined length. The development process may require side by side Western Blots and standard growth studies to demonstrate sufficient equivalence.

Western Blot analysis may also require defining the defined surrogate proteins having the associated predetermined sequence, positive control proteins, and/or a negative control proteins and may require the development of a polyclonal or monoclonal antibodies that specifically bind to specific defined surrogate proteins discussed above in Western Blot analysis or other protein analysis format, both full-length and fragments, and the positive control protein. The antibody will not bind to the negative control protein. It is also possible that a secondary antibody that is labeled with an enzyme or other visualization marker will be needed to visualize the detection antibody.

Protein array analysis can be used as a substitution for Western blot analysis in circumstances in which less sensitivity can be tolerated, but faster results are needed. In a Western Blot analysis, a substrate such as a piece of filter paper or tube is used to temporarily hold the recombinant protein sample during testing of sterilization equipment. After sterilization, deimmunization and/or disinfection, the recombinant protein sample is removed from the substrate, denatured, separated on an acrylamide gel and transferred to nylon membrane before visualizing with antibodies. In protein array analysis, the recombinant protein sample, e.g., one or more of the defined surrogate proteins having the associated predetermined sequence discussed above, is covalently crosslinked to solid surfaces such as glass, plastics or metal beads. After treatment by sterilization, deimmunization or disinfection, the solid surfaces, with the covalently crosslinked recombinant proteins are directly visualized with antibodies. Unlike Western blot analysis that can visualize the amount of protein fragmentation has occurred, protein array analysis can indicate how much of the protein sample has lost regions that are recognized by visualizing antibodies protein assay analysis but is unable to determine what other areas of the recombinant proteins were not destroyed. Thus, protein array analysis is highly suitable for testing the presence or absence of intact test proteins, such as the defined surrogate proteins having the associated predetermined sequence homologous to proteins critical for spore coats or bacteria or fungus survival or growth, e.g., one or more of the defined surrogate proteins having the predetermined sequences for *Clostridium, Bacillus, Mycobacterium, Staphylococcus, Pseudomonas, Trichophyton, Candida*, and α-Gliadin shown above. Because protein assay analysis cannot determine the absolute level of protein fragmentation that has occurred, protein array analysis may not be sensitive enough for quantifying the complete destruction of infectious proteins like prions although it is not excluded as a test method if less sensitivity is tolerated.

To establish a protein array analysis, defined quantities of the defined surrogate proteins for *Clostridium, Bacillus, Mycobacterium, Staphylococcus, Pseudomonas, Trichophyton, Candida*, and α-Gliadin above are covalently linked to a solid surface. The solid surface may include a wide support surface, such as a microscope slide made of glass or silicon, a flexible membrane, a magnetizable bead, a microtiter plate, or other similar solid surface to which a selection of the defined surrogate proteins having the associated predetermined sequence can be permanently attached. The surface used is determined by the type detector that will be used to determine the quantity of protein left on the support after sterilization, deimmunization or disinfection. After sterilization, deimmunization or disinfection, the solid surface is visualized with antibodies or other specific ligands that will specifically bind to the intact defined surrogate protein but not to destroyed defined surrogate proteins. The antibodies or other ligands can contain fluorescent dyes or other detection enabling attachments. Control slides that were not subjected to sterilization, deimmunization and/or disinfection are included as a positive control to enable estimations for the relative amount of test protein destroyed by sterilization, deimmunization and/or disinfection. FIG. 2 shows an example of multi-well glass slide 130 which has the control defined surrogate protein having the associated predetermined sequence in the wells exemplarily, indicated at 132 and multi-well glass slide 134 which has one of the defined surrogate proteins having the predetermined sequence for *Clostridium, Bacillus, Mycobacterium, Staphylococcus, Pseudomonas, Trichophyton, Candida*, and α-Gliadin in the wells, exemplarily indicated at 136. In this example, control multi well glass slide 130 was not subject to sterilization, deimmunization, or disinfection and visualization of the antibodies is indicated by the shading as shown which indicates the defined surrogate protein having the associated predetermined sequence was not sterilized, deimmunized, or disinfected. In this example, multi-well glass slide 134 was subject to sterilization, deimmunization and/or disinfection and visualization shows no presence of antibodies and, therefore, the defined surrogate proteins having the predetermined sequence were effectively sterilized. Thus, in this embodiment, the method for rapidly determining effective sterilization was able to quickly determine effective sterilization, deimmunization and/or disinfection in as little as two hours depending on the type of detection equipment used to rapidly determine effective sterilization, deimmunization or disinfection discussed above.

One key benefit of using protein array analysis in accordance with one embodiment of the method for rapidly determining effective sterilization, deimmunization, and/or disinfection of this invention is the covalently linked surrogate proteins on the surface of an object can be used for testing sterilization, deimmunization or disinfection by a sterilization, deimmunization or disinfection device that may use radiation or heat, as well as devices that use flowing disinfectants or gases to sterilize, deimmunize or disinfect medical equipment or supplies. In one example, holder 150, FIG. 3, may be used to hold multiwall glass slide 152 having one or more wells, exemplarily indicated at 154, which each holds one or more samples of the defined surrogate protein having the predetermined sequence discussed above, e.g., one of *Clostridium, Bacillus, Mycobacterium, Staphylococcus, Pseudomonas, Trichophyton, Candida* or α-Gliadin. Holder 150 with multi-well glass slide 152 including one or more samples of the defined surrogate protein having the predetermined sequence discussed above may then be placed below flow 156 of sterilization, deimmunization, or disinfection agent at the end of a medical device undergoing sterilization, deimmunization, or disinfection, indicated at 158. After the test is complete, holder 150 is then removed, indicated at 160, and multi-well glass slide 152 can be easily transferred for complete protein analysis and for rapid detection of sterilization, deimmunization, or disinfection as discussed above.

If magnetizable beads are used as the solid surface, one or more of the defined surrogate proteins having the associated predetermined sequence could also be mixed into liquid sterilization, deimmunization and/or disinfection steam and later harvested with a strong magnet. Flowing disinfectants or gases would result in the complete loss of the defined surrogate protein having the associated predetermined sequence samples that are not covalently linked to a support surface and the protein array analysis may be used to rapidly determine effective sterilization, deimmunization or disinfection.

Both Western Blot Analysis and protein array analysis are an indirect measurement of sterilization, deimmunization and/or disinfection. Sterilization is the complete destruction of spore forming infectious organisms so the standard direct measurements are long growth studies to determine the number of organisms that survived the sterilization process. Deimmunization is the complete destruction of immunogenic proteins such that no protein fragments capable of triggering an immune reaction in human or animal remain. Disinfection is the complete destruction of vegetative bacteria, fungus and/or viruses. As disclosed herein, the defined surrogate proteins are considered to be in the form of isolated fragments and destroyed if proteins critical for the survival of the infectious agents are used in quantities 10,000 to 1,000,000 times as much as would occur in a standard sample of intact infectious agents. To correctly establish the scale to determine success ratio between the direct and indirect tests, multiple conditions are preferably utilized to determine the Western Blot analysis and protein array analysis conditions that perfectly align with standard sterilization, deimmunization and/or disinfection studies using intact infectious organisms and post sterilization growth conditions.

The samples prepared for Western Blot analysis and protein array analysis may use a wide range of circumstances. If the sterilization, deimmunization and/or disinfection equipment uses flowing gases or liquid to wash over the surfaces to be sterilized holder 150, FIG. 3, and multi-well glass slide 152 or similar type device, may be used to ensure the defined surrogate protein samples remain in the flowing stream of disinfecting gas or liquid. For example, if the sterilization, deimmunization or disinfecting gas or liquid is washed through medical equipment to sterilize, deimmunize, or disinfect the inside of a lumen, holder 150 with the multi-well glass slide 150 having one or more defined surrogate proteins having the associated predetermined sequence therein, e.g., *Clostridium, Bacillus, Mycobacterium, Staphylococcus, Pseudomonas, Trichophyton, Can-* dida, and α-Gliadin analysis tests could be connected to the end of the stream to better measure the quality of sterilization, deimmunization, or disinfection that occurred through the entire length of the medical equipment lumen.

The following examples are exemplary and explanatory only and do not limit or restrict this invention.

Examples

Example 1: Comparing Amino Acid Sequence of Human PrP Protein to Other Species

It is important to qualify the ability of a sterilization device to destroy prions that may be contaminating medical equipment. For the specific test described herein in accordance with one or more embodiments of the method for rapidly determining effective sterilization, deimmunization, or disinfection of this invention, a defined quantity of the defined surrogate prion protein discussed above is provided and then evaluated using Western Blot analysis and an antibody specific for the defined prion surrogate protein.

To protect the human operators of the test, infectious human prions cannot be used. Instead, the defined surrogate protein is used that incorporates all the characteristics of human prion (PrP) proteins, with the critical exception that it cannot infect humans. In this example, to select the defined surrogate PrP protein to be used, a protein analysis was conducted comparing the amino acid protein sequence of human PrP protein against a selection of the protein sequence databases of other species including a primate, two companion animals, two food animals and two research animals. From this analysis, the mouse PrP protein was determined to be the best candidate surrogate protein. Structurally, mouse PrP protein is as robust as the human PrP protein and thus will be equivalently resistant to a wide range of destructive methods but is also sufficiently different as to be unable to infect humans. Arrow 168, FIG. 4, indicates the initiation location for Pr27-30, the smallest PrP fragment that retains infectivity. If a PrP protein is cleaved anywhere from this initiation point to the end of the protein sequence, the resulting fragments can no longer cause disease.

To evaluate additional surrogate PrP proteins that could be used, the mouse PrP protein sequence was compared against the protein sequence database. Table 5 below shows the wide diversity of a predetermined list of species PrP proteins that could be used as well as each protein's sequence ID and its homology to Mouse PrP. The human sequence is less than 90% homologous to mouse PrP. The search also demonstrates how conserved the PrP protein is across a wide range of mammalian species contained within the sequence database and any one of these could be used as the surrogate protein in the Protein Indicator Test. The database also contains the sequence for chicken PrP but as it is less than 50% homologous to other mammalian PrP proteins, it is possible that it or other related proteins could be used in the Protein Indicator Test but its divergence could impact its resistance to destruction. This would make it a less suitable surrogate for the test than other proteins, especially any mammalian PrP protein.

TABLE 5

Potential PrP Protein that could be used as Surrogate Protein in Sterilization Indication Tests. Information about each PrP protein includes species, Sequence ID number and homology to Mouse recombinant PrP protein.

| Species | Sequence ID Number | Homology to Mouse (%) |
|---|---|---|
| Mouse (*Mus musculus*) | sp\|P04925.2\|PRIO_MOUSE | 100 |
| Rat (*Rattus norvegicus*) | sp\|P13852.2\|PRIO_RAT | 98 |
| Cotton Rat (*Sigmodon hispidus*) | sp\|Q9Z0T3.1\|PRIO_SIGHI | 97 |
| Chinese Hamster (*Cricetulus griseus*) | sp\|Q60506.1\|PRIO_CRIGR | 97 |
| Grey Dwarf Hamster (*Cricetulus migratorius*) | sp\|Q60468.1\|PRIO_CRIMI | 95 |
| Golden Hamster (*Mesocricetus auratus*) | sp\|P04273.1\|PRIO_MESAU | 95 |
| Greater Kudu (*Tragelaphus strepsiceros*) | sp\|P40243.1\|PRIO2_TRAST | 90 |
| Red-bellied Titi (*Callicebus moloch*) | sp\|P40248.1\|PRIO_CALMO | 96 |
| Three-striped Night Monkey (*Aotus trivirgatus*) | sp\|P40245.1\|PRIO_AOTTR | 94 |
| Black-capped capuchin (*Sapajus apella*) | sp\|P40249.1\|PRIO_CEBAP | 95 |
| Common Marmoset (*Callithrix jacchus*) | sp\|P40247.1\|PRIO_CALJA | 95 |
| Red-faced Spider Monkey (*Ateles paniscus*) | sp\|P51446.1\|PRIO_ATEPA | 94 |
| Geoffrey's Spider Monkey (*Ateles geoffroyi*) | sp\|P40246.1\|PRIO_ATEGE | 91 |
| Nilgai (*Boselaphus tragocamelus*) | sp\|Q5UJG7.1\|PRIO_BOSTR | 86 |
| Alpine Musk Deer (*Moschus chrysogaster*) | sp\|Q68G95.1\|PRIO_MOSCH | 88 |
| Common Squirrel Monkey (*Saimiri sciureus*) | sp\|P40258.1\|PRIO_SAISC | 91 |
| Gelada Baboon (*Theropithecus gelada*) | sp\|Q95270.1\|PRIO_THEGE | 90 |
| Black Crested Mangabey(*Lophocebus aterrimus*) | sp\|P67990.1\|PRIO_LOPAT | 90 |
| Mona Monkey(*Cercopithecus mona*) | sp\|P61761.1\|PRIO_CERMO | 91 |
| Patas Monkey(*Erythrocebus patas*) | sp\|Q95174.1\|PRIO_ERYPA | 91 |
| Grivet(*Chlorocebus aethiops*) | sp\|P67988.1\|PRIO_CHLAE | 90 |
| Mantled Guereza(*Colobus guereza*) | sp\|P40251.1\|PRIO_COLGU | 91 |
| Bornean orangutan(*Pongo pygmaeus*) | sp\|P40256.1\|PRIO_PONPY | 91 |
| François' Langur (*Trachypithecus francoisi*) | sp\|P40257.2\|PRIO_TRAFR | 91 |
| Sooty Mangabey (*Cercocebus atys*) | sp\|Q95176.1\|PRIO_CERAT | 91 |
| Crab-eating Macaque (*Macaca fascicularis*) | sp\|P67992.1\|PRIO_MACFA | 91 |
| Mandrill(*Mandrillus sphinx*) | sp\|P40255.1\|PRIO_MANSP | 91 |
| Gorilla (*Gorilla gorilla gorilla*) | sp\|P40252.1\|PRIO_GORGO | 90 |
| Cat (*Felis catus*) | sp\|O18754.3\|PRIO_FELCA | 87 |
| Human (*Homo sapiens*) | sp\|P04156.1\|PRIO_HUMAN | 89 |
| Lar Gibbon(*Hylobates lar*) | sp\|P61766.1\|PRIO_HYLLA | 89 |
| Bighorn Sheep (*Ovis canadensis*) | sp\|Q7JIH3.1\|PRIO_OVICA | 88 |
| Goat(*Capra hircus*) | sp\|P52113.1\|PRIO_CAPHI | 88 |
| Blackbuck(*Antilope cervicapra*) | sp\|Q5UJG1.1\|PRIO_ANTCE | 85 |
| Takin(*Budorcas taxicolor*) | sp\|Q95M08.1\|PRIO_BUDTA | 87 |

TABLE 5-continued

Potential PrP Protein that could be used as Surrogate Protein in Sterilization Indication Tests. Information about each PrP protein includes species, Sequence ID number and homology to Mouse recombinant PrP protein.

| Species | Sequence ID Number | Homology to Mouse (%) |
|---|---|---|
| Sheep (*Ovis aries*) | sp\|P23907.1\|PRIO_SHEEP | 87 |
| Rabbit (*Oryctolagus cuniculus*) | sp\|Q95211.1\|PRIO_RABIT | 90 |
| Water Buffalo (*Bubalus bubalis*) | sp\|Q5UJH8.1\|PRIO_BUBBU | 84 |
| Rocky Mountain Elk (*Cervus canadensis nelsoni*) | sp\|P67986.1\|PRIO_CEREN | 87 |
| Mule Deer (*Odocoileus hemionus*) | sp\|P47852.1\|PRIO_ODOHE | 87 |
| Lesser Kudu (*Tragelaphus imberbis*) | sp\|Q5UJG3.1\|PRIO_TRAIM | 85 |
| Greater Kudu(*Tragelaphus strepsiceros*) | sp\|P40242.1\|PPIO1_TRAST | 84 |
| Cow (*Bos taurus*) | sp\|P10279.2\|PRIO_BOVIN | 84 |
| Common Brushtail Possum (*Trichosurus Vulpecula*) | sp\|P51780.1\|PRIO_TRIVU | 77 |
| Giant Panda(*Ailuropoda melanoleuca*) | sp\|Q6EH52.1\|PRIO_AILME | 84 |
| American Mink (*Neovison vison*) | sp\|P40244.1\|PRIO_NEOVI | 79 |
| Dromedary Camel (*Camelus dromedaries*) | sp\|P79141.1\|PRIO_CAMDR | 88 |
| Pig (*Sus scrofa*) | sp\|P49927.1\|PRIO_PIG | 79 |
| Ferret(*Mustela putorius furo*) | sp\|P52114.1\|PRIO_MUSPF | 78 |
| Artic Fox(*Vulpes lagopus*) | sp\|B0FYL5.1\|PRIO_VULLA | 78 |
| Dog (*Canis lupus familiaris*) | sp\|O46501.1\|PRIO_CANFA | 85 |
| Chicken (*Gallus gallus*) | sp\|P27177.2\|PRIO_CHICK | 43 |

Example 2: Developing Method for Testing the Ability to Destroy PrP Proteins

One purpose of developing the defined prion surrogate protein test is to provide a rapid method for determining effective sterilization equipment. The method preferably has multiple steps including at least: 1) preparing defined prion surrogate proteins having a predetermined sequence, 2) subjecting the prion surrogate protein samples to sterilization, and 3) using Western Blot analysis to visualize the effects of sterilization of defined prion surrogate protein samples. Successful sterilization has occurred when all of the defined prion surrogate protein sample was fragmented and, as a result of the protein fragmentation, none remains to bind to the visualization antibodies. If sterilization was not successful, protein bands will be see on the Western Blot analysis.

A defined surrogate protein having a sequence above for the prions, recombinant mouse PrP full-length protein (208 amino acids long) was obtained from Abcam, Cambridge Mass. On a Western gel, the recombinant protein runs at about approximated 28 kDa in size, indicated at 290, FIG. 5.

The Western Blot analysis discussed above is well-established and is an extremely sensitive method to determine the presence and/or absence of a specific protein. The first step in Western Blot analysis involves preparing the defined prion surrogate protein samples for separation by size. In accordance with one embodiment of the method for rapidly determining effective sterilization, deimmunization, or disinfection of the defined prion surrogate proteins will be run as single denatured proteins and thus must be denatured through the use of a denaturing loading buffer, boiled for 10 minutes and then run on a denaturing gel. Once loaded on to an appropriate acrylamide gel, the samples are subjected to electric current that results in the protein fragments traveling at different rates depending on size with smaller fragments moving faster than larger ones. In one example, the gel contained 8% acrylamide. To be able to monitor the separation of the defined prion surrogate protein samples, a standard sample with a mix of proteins of defined sizes was also included. For some experiments discussed herein, additional protein samples may be included to provide for controls of the sample handling conditions:

After separation, the defined prion surrogate protein samples are transferred to a special nylon membrane before being permanently cross-linked to the membrane. The final steps include incubating the nylon membrane with a primary antibody available from Abeam, Cambridge Mass. that specifically binds to the defined surrogate protein of interest. In the experiments discussed herein, the primary anti-PrP antibody was a rabbit monoclonal antibody that was raised against a synthetic peptide corresponding to residues near the C-terminus of human Prion protein PrP, as indicated by underlined region indicated at 170, FIG. 4. In addition to binding to both $PrP_c$ and $PrP_{sc}$, the antibody will bind to the infectious protein form PrP 27-30. The primary antibody binds to Human, Rat and Mouse PrP proteins. The secondary antibody is a HRP-labelled goat anti-rabbit available from Abcam, Cambridge Mass. to enable visualization of the infectious PrP fragments, both intact and fragmented. If the defined prion surrogate proteins have been fragmented into non-infectious fragments that eliminate the C-terminus region of the PrP, the antibody will not bind them. Without this C-terminus region, the degraded PrP protein is no longer infectious. Very small fragments and amino acids which are no longer infectious will be too small to be retained on the gel.

The first tests involved carefully drying defined quantities of recombinant mouse PrP protein onto filter papers to assist in storage, transport to and from location of sterilization equipment and handling during sterilization tests. To create, test strips of filter paper were cut 4 mm wide by 20 mm long and the bottoms were squared. Serial dilutions (1:3) of mouse PrP protein were created to contain protein solutions 0.1 μg/μl to 0.0037 μg/μl. The protein preps were added dropwise to the filter paper strips until 10 ul were added. The filter paper strips were then air dried. Filter paper strips were prepared in duplicate with 1 μg, 0.333 μg, 0.111 μg, or 0.033 μg applied respectively to a pair of strips. When dry, the strips were placed in Eppendorf tubes and 50 ul 1× Loading Buffer where BME was added. The strips and loading buffer were incubated at 95° C. for 5 minutes then given a quick spin in a micro centrifuge. For one of each paired sample, the filter paper strip was taken out of the Eppendorf tube and inserted into the well of the SDS-PAGE gel. For these samples, electroporation was used to extract any residual defined prion surrogate protein that was retained on the filter paper after extraction by boiling and centrifugation. Half of the loading buffer from these tubes was also loaded into the same well. For the other samples of the pair only boiling and centrifugation was used to extract the defined prion surrogate protein from the filter strips. From these, half of the loading buffer was added to the wells without also adding the filter paper. A control sample of 0.5 µg protein (equivalent to half of the 1 µg concentration samples) was also loaded on the gel for comparison. The gel was run and the Western Blot Analysis performed using the procedure described above.

The results demonstrated that there was no significant difference between the protein concentrations that were dried onto the filter paper and the control sample. There was also no significant difference between the extraction process using only boiling and centrifugation and the more difficult process of using boiling, centrifugation and electroporation for extraction. In addition, the Western Blot analysis demonstrated that the Western Blot analysis was sensitive to below 0.05 µg. Hence, a 1 µg of recombinant mouse PrP protein should be used for all sterilization tests. The samples should be extracted from filter paper using boiling in loading the buffer with BME and centrifugation and half of the sterilized samples used for Western Bolt analysis.

Figures 5, 6:
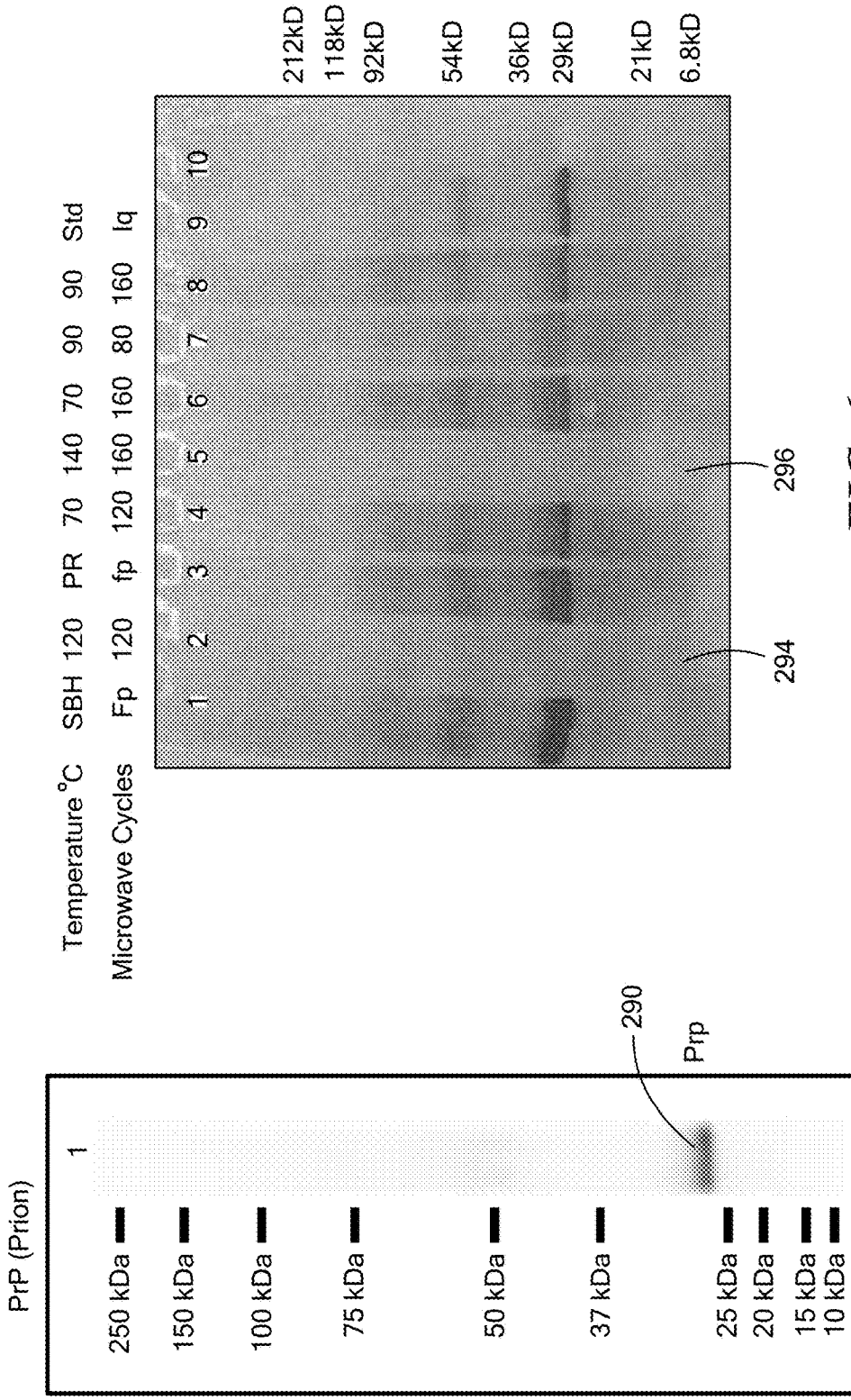
FIG. 5 shows an example of a Western gel where the recombinant protein runs approximately 28 kDa inside.
FIG. 6 shows an example of a Western Blot where the absence of bands indicates successful sterilization, deimmunization, or disinfection.

Example 3: Evaluation of Destruction of Prion Proteins Using Sterilization Equipment Experiments were conducted to demonstrate a combination of one or more of heat, a vaporizing solvent, and electromagnetic radiation, e.g., microwaves, e.g., as disclosed in the '469 patent application, could irreversibly destroy the defined prion surrogate protein shown with the sequence shown above. The stable PrP protein was selected for the experiments as it cannot be irreversibly destroyed using a standard sterilization autoclave device. For the experiments, samples were created that each contained 1 µg of a structurally robust mouse PrP protein and wrapped in 100% cotton paper to avoid extraneous contamination. This containment was placed in a second layer of 100% cotton paper to increase stability during treatment. The samples were treated with different temperatures and for differing numbers of moisture saturation and microwave cycles, e.g., as disclosed in the '469 patent application. After treatment, the samples were prepared in loading buffer and boiled. Half of each sample was then run on a denaturing protein gel. After Western Blot analysis, it was possible to see that certain combinations of temperature and treatment cycles completely destroyed the stable protein samples, shown by the absence of protein bands of gel indicated at 294, 296, FIG. 6. Other treatment conditions did not destroy the stable proteins.

Example 4: Evaluation of Destruction of Prion Proteins Contained within Polypropylene Tubes Additional experiments were conducted to demonstrate that with the combination of one or more of heat, saturating moisture and microwaves as disclosed in the '469 patent application could destroy the defined surrogate stable PrP proteins if the samples were contained within a vessel such as a polypropylene tube. In this example, samples of the defined prion surrogate proteins were created that each contained about 1 µg of a structurally robust mouse protein. However, instead of drying the protein samples onto filter paper, the 1 µg samples were dried within polypropylene tubes of different lengths including 0.75 cm and 3.5 cm in length. The tubes were closed at one end (on to which the samples were dried) and open at the other. The tubes were contained within 2 layers of 100% cotton paper to prevent cross contamination during treatment. The samples were subjected to sterilization by a combination of one or more of heat, a solvent, e.g., reverse osmois (RO) filtered water, and electromagnetic radiation with differing numbers of moisture saturation and radiation cycles, e.g., as disclosed in the '469 patent application. After treatment, the samples were prepared in loading buffer and boiled. Half of each sample was then run on a denaturing protein gel. After Western blot analysis, it was possible to see that certain combinations of temperature and treatment cycles completely destroyed the stable protein samples (as demonstrated by the absence of protein bands of gel). Other treatment conditions did not destroy the stable proteins. The results of the sterilization treatment of PrP samples dried onto filter paper and dried within a polypropylene tube were identical indicating that the method of containing the PrP sample did not alter the results.

Example 5: Comparison of Prion Protein Indicator Test Results and Mouse Model Prion Tests All mice were kept in an AAALAC-accredited facility and handled in compliance with guidelines provided by the US Guide for the Care and Use of Laboratory Animals.

Creating Prion Infected Brain Homogenate: Brains from terminally ill C57BL/6 mice infected with 22 L prions were prepared as follows: each brain was homogenized (10%, w/v) in phosphate-buffered saline (PBS) by repeatedly passing the material first through an 18-gauge needle and then repeatedly through a 26 gauge needle. The brain homogenates were combined to make a stock preparation, diluted with PBS (1/10), aliquoted into 100 ul preps in 2 ml polypropylene freezing vials and frozen at $-80°$ C. until use.

Division into treated and non-treated preps: frozen prion preps having the defined prion surrogate protein were allowed to thaw and the caps removed. In duplicate, samples were sterilized by a combination of one or more of heat, microwaves and saturating moisture, e.g., as disclosed in the '469 patent application. The used conditions were similar to the process disclosed in Example 4 above. In one example, the sterilization preferably includes: (A) 140° C., 100 cycles of microwave; (B) 100° C., 100 cycles of microwave; and (C) room temperature, 100 cycles with no microwaves. The Prion Protein Indicator Test having the defined surrogate protein samples were analyzed by Western Blot analysis as described in Example 4 above. Depending on treatment conditions, the test sample was completely destroyed (A), partially destroyed (B), or completely intact (C).

Testing infectiveness of Prion Prep: C57BL/6 mice aged 4-5 weeks were divided into 4 cohorts, 10 mice per cohort, to receive the samples that correlated with the following Prion Protein Indicator Test samples having the defined prion surrogate protein: (A) complete destruction; (B) partial destruction; (C) no treatment and (D) PBS control. After anesthesia each mouse was intracerebrally inoculated with a 20 ul-aliquot of the designated inoculum. The mice were observed up to one year after inoculation, unless they displayed terminal symptoms of PrP infection including persistent signs of ataxia, kyphosis, somnolence, and hind leg weakness. Terminally-ill mice were euthanized and their brains divided sagittally along the midline and place formalin fixation for histological analysis or flash-frozen in liquid nitrogen for protein analysis. At one year, all remaining mice (showed no obvious signs of neurologic disease) were euthanized and their brains also divided for histological analysis or protein analysis.

Results: Over the observation period, none of the mice that received either the PBS control (D) or the brain homogenate treated with the conditions that demonstrated complete destruction on the Prion Protein Indicator Test having the defined prion surrogate protein (A) demonstrated any symptoms of disease. After euthanization, none of the brains demonstrated any signs of prion disease. Western Blot analysis of the brains showed no increase in concentrations of PrP proteins over normal levels. The mice that received the brain homogenate and also received no sterilization treatment (C) or partial destruction (B) as indicated by the Priori Protein Indicator Test all demonstrated terminal symptoms of PrP infection before the completion of the 1 year observation period. Their brains demonstrated obvious signs of prion disease and by Western analysis, the concentration of PrP proteins were greatly increased over normal levels. Together the results of the mouse study indicated a clear correlation between the results from the Prion Protein Indicator Test results and the mouse model results.

Example 6: Comparing Amino Acid Sequence of Multiple Members of the *Clostridium* Genus It is important to qualify the ability of a sterilization device, a deimmunization device, or a disinfection device to destroy bacteria of any *Clostridium* species that may be contaminating medical equipment or supplies. In this example, a defined quantity of the defined surrogate protein having the predetermined SEQ ID NO: 1 discussed above was subjected to sterilization, deimmunization, or disinfection to rapidly determine the effectiveness of the sterilization, deimmunization, or disinfection using Western Blot analysis, protein array analysis, or similar type analysis, and the antibody for the defined *Clostridium* surrogate protein shown above. In this example, to protect the human operators of the test, the defined surrogate protein needs to incorporate critical characteristics of *Clostridium* proteins that are critical for the survival and growth of members of the *Clostridium* genus while avoiding organisms that can infect humans.

To design the synthetic defined surrogate, *Clostridium* protein having the predetermined sequence, SEQ ID NO: 1, a protein analysis was conducted comparing the amino acid sequences of the suf I loci gene from multiple species of the *Clostridium* genus shown in Table 2 above. In this example, the Sequence IDs (found in Pubmed, www.ncbi.nlm.nih.gov/Pubmed/) for the suf I loci proteins, multiple *Clostridium* species, used for the comparative are shown in Table 5 below:

TABLE 5

(*Clostridium*). Sequences used to determine regions of high homology in suf I locus of multiple *Clostridium* Species.

| Species | Sequence ID |
| --- | --- |
| Clostridium sporogenes | WP_061905762.1 |
| Clostridium botulinum | WP_011948579.1 |
| Clostridium novyi | WP_039217212.1 |

The protein produced by the suf I loci is fundamental to survival and growth of a wide range of spores, bacteria and fungus. In species of the *Clostridium* genus, the protein product of the suf I loci is called cotA and is critical for many live stages including strongly contributing to the stability of the spore coat.

To design the defined *Clostridium* surrogate protein having SEQ ID NO: 1, the specific amino acids from the proteins listed in Table 5 were aligned to determine amino acid sequence regions that are highly homologous in all evaluated *Clostridium* species as shown in FIG. 7. The protein encoded by the suf 1 loci includes three cupredoxin domains that are indicated at 200 for domain 1, 202 for domain 2, and 204 for domain 3. In the *Clostridium* genus, domain 2, indicated at 202, shows high homology between *Clostridium* species so was used to for the design of the synthetic surrogate protein SEQ ID NO: 1 above to be created for the *Clostridium* test and the corresponding peptides discussed above were used to develop the polyclonal and monoclonal antibodies for use by Western Blot analysis.

Example 7: Developing Western Test to Qualify Ability to Destroy *Clostridium* Test Protein One purpose of developing the synthetic defined *Clostridium* surrogate protein is to provide a method for rapidly determining the effectiveness of sterilization, deimmunization, and/or disinfection by a device, such as sterilization device, deimmunization device, or disinfection device. In this example, the method for rapidly determining effective sterilization, deimmunization, and/or disinfection includes multiple steps including at least: 1) preparing the synthetic defined *Clostridium* surrogate protein test samples, 2) subjecting the defined *Clostridium* surrogate protein test samples to sterilization, deimmunization, or disinfection, and 3) using Western Blot or similar type analysis to visualize the effects of sterilization, deimmunization, or disinfection of defined *Clostridium* surrogate protein test samples. Successful sterilization, deimmunization, or disinfection has occurred when all the defined *Clostridium* surrogate protein test samples are fragmented and as a result of the protein fragmentation, none remains to bind to the visualization antibodies indicating the defined *Clostridium* surrogate protein was destroyed. If sterilization, deimmunization, or disinfection was not successful, protein bands will be seen on the Western Blot analysis.

Following the process more fully described for the Prion test, a similar process was followed to create the *Clostridium* sterilization, deimmunization, and/or disinfection test. First, to create the sample for the test using the defined *Clostridium* surrogate protein, DNA encoding the amino acid SEQ ID NO: 1 for *Clostridium* above was synthesized and cloned into standard vectors both for *E. coli* and yeast expression. Using standard techniques, large quantities of protein were produced in *E. coli* or yeast and isolated by standard recombinant methods. Using a nickel column, a full-length defined *Clostridium* surrogate protein (171 amino acids long) was isolated. To create the samples having the defined *Clostridium* surrogate protein to qualify sterilization, deimmunization, or disinfection of the samples were dried onto small filter papers, dried inside small tubes or a surface of an object subjected to sterilization, deimmunization, or disinfection e.g., using cycles of applying a solvent and microwave energy as disclosed in the '469 patent application.

After sterilization, deimmunization, or disinfection, the treated *Clostridium* samples were transferred to tubes, denatured and separated by size and transferred to nylon membrane before being permanently cross-linked to the membrane. The final steps include incubating the nylon membrane with a primary antibody that specifically binds to the defined *Clostridium* surrogate protein of interest. In the experiments discussed herein, the primary anti-suf I loci encoded protein antibody was a rabbit polyclonal antibody that was raised against a synthetic peptide discussed above for SEQ ID NO: 1 residues. For added sensitivity, addition antibodies, both monoclonal and polyclonal, were raised against the other synthetic peptide(s). For the Western Blot Analysis, a secondary antibody may be a HRP-labelled goat anti-rabbit to enable visualization of the protein fragments, both intact and fragmented. If the defined *Clostridium* surrogate proteins have completely fragmented no bands will be visualize on the Western blot. Very small fragments and amino acids will be too small to be retained on the gel. When successful sterilization, deimmunization, or disinfection occurred, the visualized Western blot has a dark ban in the untreated control sample, e.g., indicated at 210, FIG. 8, and a complete absence of any bands for the defined *Clostridium* surrogate protein sample subjected to sterilization, deimmunization, or disinfection indicates successful sterilization, deimmunization, or disinfection, e.g., indicated at 212.

Example 8: Comparing Amino Acid Sequence of Multiple Members of the *Bacillus* Genus It is important to qualify the ability of a sterilization device, a deimmunization device or disinfection device to destroy bacteria of any *Bacillus* species that may be contaminating medical equipment or supplies. In this example, a defined quantity of the defined *Bacillus* surrogate protein having the predetermined SEQ ID NO: 2 discussed above is subjected to sterilization, deimmunization, or disinfection to rapidly determine the effectiveness of the sterilization, deimmunization, or disinfection using Western Blot analysis, protein array analysis, or similar type analysis, and the antibody for the defined *Bacillus* surrogate protein shown above. In this example, to protect the human operators of the test, the defined surrogate *Bacillus* surrogate protein needs to incorporate critical characteristics of *Bacillus* proteins that are critical for the survival and growth of members of the *Bacillus* genus while avoiding organisms that can infect humans.

To design the synthetic defined surrogate *Bacillus* protein having SEQ ID NO: 2, a protein analysis was conducted comparing the amino acid sequences of the suf I loci gene from multiple species of the *Bacillus* genus shown in Table 2 above. In this example, the Sequence IDs (found in Pubmed, www.ncbi.nlm.nih.gov/Pubmed/) for the suf I loci encoded proteins, multiple *Bacillus* species, used for the comparative are shown in Table 6 below.

TABLE 6

(*Bacillus*). Sequences used to determine regions of high homology in suf 1 locus of multiple *Bacillus* Species.

| Species | Sequence ID |
|---|---|
| *Bacillus subtilis* | AAB62305.1 |
| *Bacillus atrophaeus* | WP_011948579.1 |
| *Bacillus pumilus* | WP_039217212.1 |

The protein produced by the suf I loci is fundamental to survival and growth of a wide range of spores, bacteria and fungus. In species of the *Bacillus* genus, the protein product of the suf I loci is called cotA and is critical for many live stages including strongly contributing to the stability of the spore coat.

Figure 9:
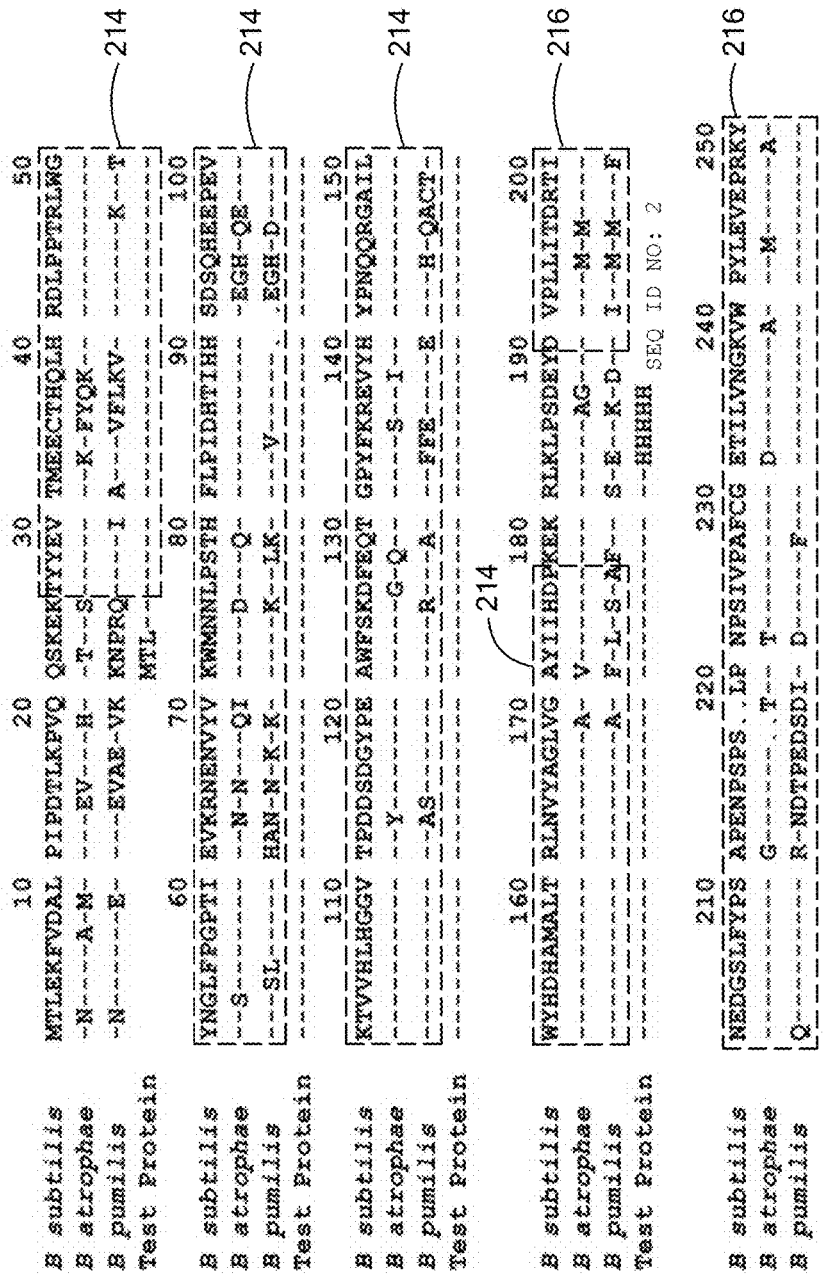
FIG. 9 is a homology diagram comparing protein sequences of a three research *Bacillus* species.

To design the synthetic defined *Bacillus* surrogate protein for SEQ ID NO: 2, the specific amino acids from the proteins listed in Table 6 were aligned to determine amino acid sequence regions that are highly homologous in all evaluated *Bacillus* species as shown in FIG. 9. The protein encoded by the suf 0.1 loci includes three cupredoxin domains, indicated at 214 for domain 1, 216 for domain 2, and 218 for domain 3. In the *Bacillus* genus, domain 2, indicated at 216, shows high homology between *Bacillus* species, so SEQ ID NO: 2 above was used as the synthetic defined *Bacillus* surrogate protein to be used for the *Bacillus* test and the corresponding peptide discussed above was used to raise a polyclonal antibody for use by Western Blot analysis. Additional polyclonal and monoclonal antibodies were created as needed.

Example 9: Developing Western Test to Qualify Ability to Destroy *Bacillus* Test Protein One purpose of developing the synthetic defined *Bacillus* surrogate protein is to provide a method for rapidly determining the effectiveness of sterilization, deimmunization, and/or disinfection by a device, such as a sterilization device, deimmunization device, or disinfection device. The method for rapidly determining effective sterilization, deimmunization, and/or disinfection preferably includes multiple steps including at least: 1) preparing synthetic defined *Bacillus* surrogate protein test samples, 2) subjecting the *Bacillus* surrogate protein test samples to sterilization, deimmunization, or disinfection, and 3) using Western Blot or similar analysis to visualize the effects of sterilization, deimmunization, or disinfection of defined *Bacillus* surrogate protein test samples. Successful sterilization, deimmunization, or disinfection has occurred when all the defined *Bacillus* surrogate protein test samples are fragmented and as a result of the protein fragmentation, none remains to bind to the visualization antibodies indicating the defined *Bacillus* surrogate protein was destroyed. If sterilization, deimmunization, or disinfection was not successful, protein bands will be see on the Western Blot analysis.

Following the process more fully described for the Prion test, a similar process was followed to create the *Bacillus* sterilization, deimmunization, and/or disinfection test. First, to create the sample for the test using the synthetic defined *Bacillus* surrogate protein, DNA encoding the amino acid for SEQ ID NO: 2 above was synthesized and cloned into standard vectors both for *E. coli* and yeast expression. Using standard techniques, large quantities of the defined *Bacillus* surrogate protein were produced in *E. coli* or yeast and isolated by standard recombinant methods. Using a nickel column, a full-length defined *Bacillus* surrogate protein (171 amino acids long) was isolated. To create the samples having the synthetic defined *Bacillus* surrogate protein to qualify sterilization, deimmunization, and/or disinfection the samples were dried onto small filter papers, dried inside small tubes or a surface of an object subjected to sterilization, deimmunization, or disinfection, e.g., using cycles of applying a solvent and microwave energy, e.g., as disclosed in the '469 patent application.

Figure 10:
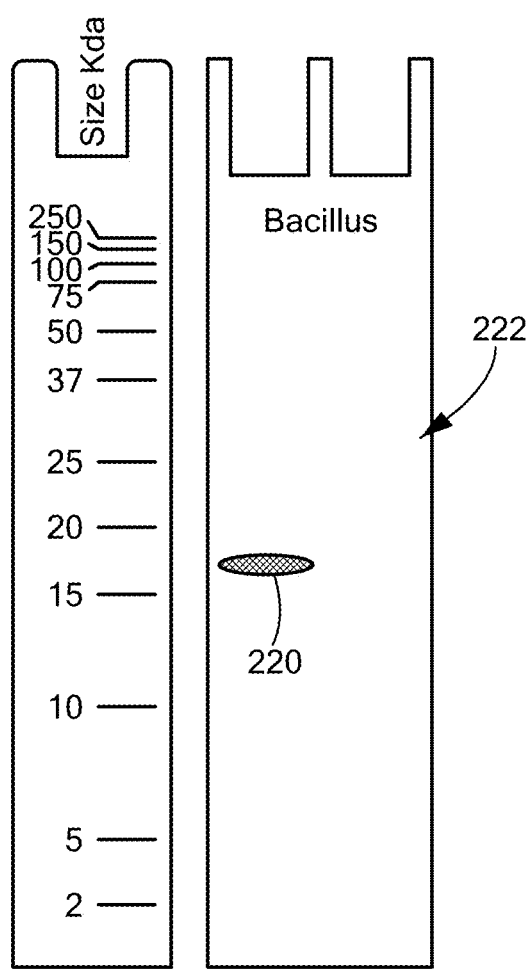
FIG. 10 shows an example of a Western Blot for a defined *Bacillus* surrogate protein having a predetermined sequence that has been subjected to sterilization, deimmunization, or disinfection.

After sterilization deimmunization and/or disinfection, the treated *Bacillus* samples were transferred to tubes, denatured and separated by size and transferred to nylon membrane before being permanently cross-linked to the membrane. The final steps include incubating the nylon membrane with a primary antibody that specifically binds to the defined *Bacillus* surrogate proteins. In the experiments discussed herein, the primary anti-suf I loci protein antibody was a rabbit polyclonal antibody that was raised against a synthetic peptide discussed above for SEQ ID NO: 2 residues. For added sensitivity, addition antibodies, both monoclonal and polyclonal, were raised against the other synthetic peptide(s). For the Western Blot Analysis, a secondary antibody may be a HRP-labelled goat anti-rabbit to enable visualization of the protein fragments, both intact and fragmented. If the defined *Bacillus* surrogate proteins have completely fragmented no bands will be visualize on the Western blot. Very small fragments and amino acids will be too small to be retained on the gel. When successful sterilization, deimmunization, or disinfection occurred, the visualized Western blot has a dark ban in the untreated control sample, e.g., indicated at 220, FIG. 10, and a complete absence of any bands for defined *Bacillus* surrogate protein sample subjected to sterilization, deimmunization, or disinfection indicates successful sterilization, deimmunization, or disinfection, indicated at 222.

Example 10: Comparing Amino Acid Sequence of Multiple Members of the *Mycobacterium* Genus It is important to qualify the ability of a sterilization device, a deimmunization device, or a disinfection device to destroy bacteria of any *Mycobacterium* species that may be contaminating medical equipment or supplies. In this example, a defined quantity of the defined surrogate protein having a SEQ ID NO: 3 discussed above is subjected to sterilization, deimmunization, or disinfection to rapidly determine the effectiveness of the sterilization, deimmunization, or disinfection using Western Blot analysis, protein array analysis, or similar type analysis and using an antibody specific for the protein. In this example, to protect the human operators of the test, the defined *Mycobacterium* surrogate protein needs to incorporate critical characteristics of *Mycobacterium* proteins that are critical for the survival and growth of members of the *Mycobacterium* genus while avoiding organisms that can infect humans.

To design the synthetic defined *Mycobacterium* surrogate protein SEQ ID NO: 3 above, a protein analysis was conducted comparing the amino acid sequences of the suf I loci gene from multiple species of the *Mycobacterium* genus shown in Table 2 above. In this example, the Sequence IDs (found in Pubmed, www.ncbi.nlm.nih.gov/Pubmed/) for the suf 1 loci proteins, multiple *Mycobacterium* species, used for the comparative are shown in Table 7 below:

TABLE 7

(Mycobacteria). Sequences used to determine regions of high homology in suf 1 locus of multiple *Mycobacterium* Species.

| Species | Sequence ID |
| --- | --- |
| Mycobacterium tuberculosis | WP_003404392.1 |
| Mycobacterium africanum | KBG17039.1 |
| Mycobacterium kansasii | WP_023367763.1 |

The protein produced by the suf I loci is fundamental to survival and growth of a wide range of spores, bacteria and fungus. In species of the *Mycobacterium* genus, the protein product of the suf I loci is called cumA and is critical for many live stages including cell survival and growth.

Figure 11:
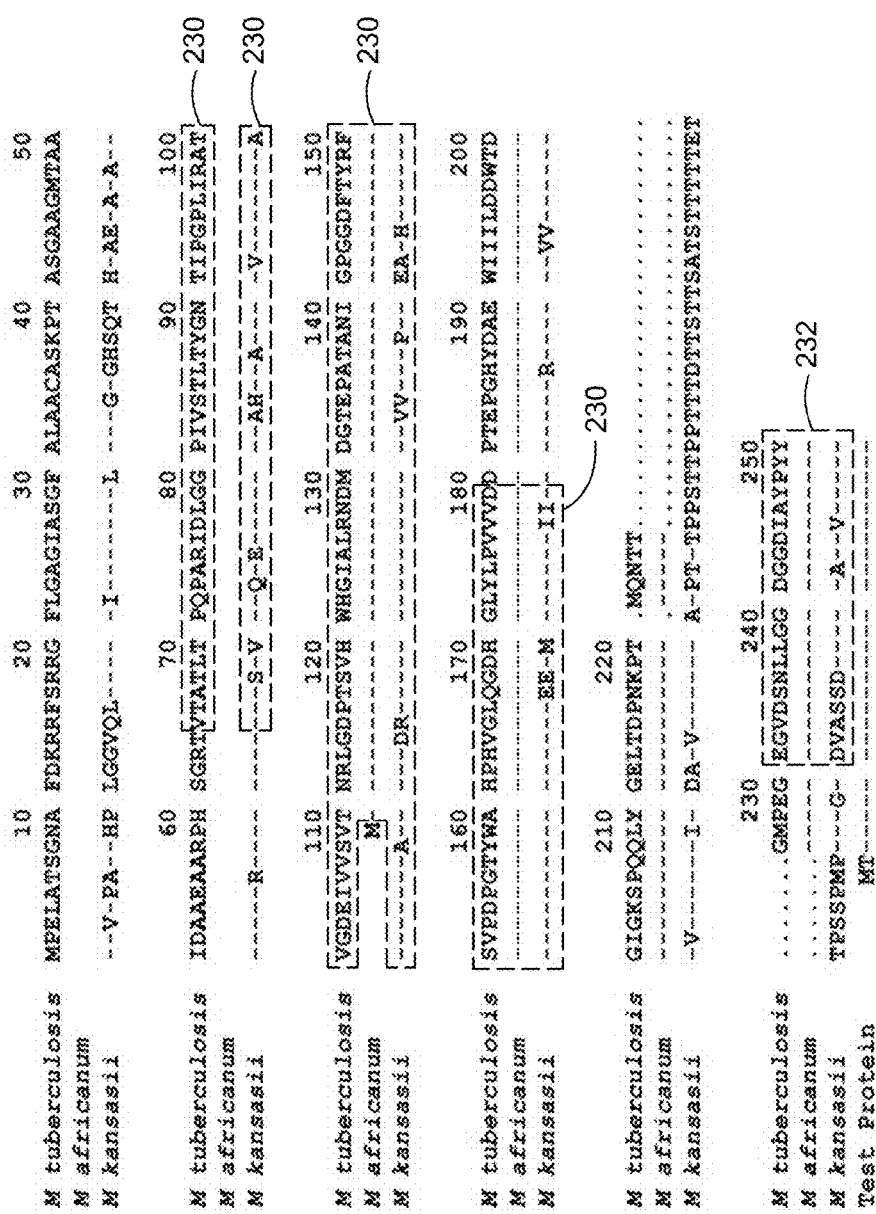
FIG. 11 is a homology diagram comparing protein sequences of three pathogenic *Mycobacterium* species.
Figure 12:
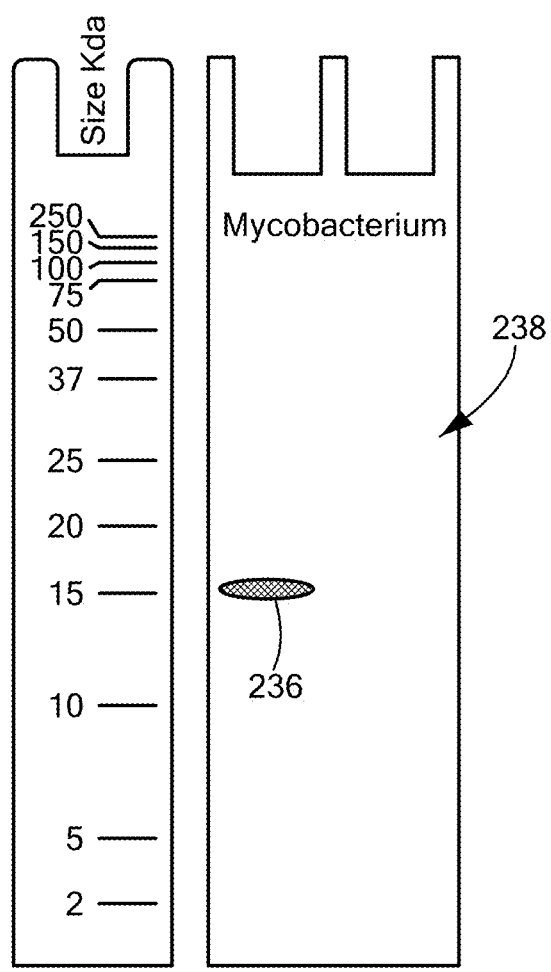
FIG. 12 shows an example of a Western Blot for a defined *Mycobacterium* surrogate protein having a predetermined sequence that has been subjected to sterilization, deimmunization, or disinfection.
Figure 13:
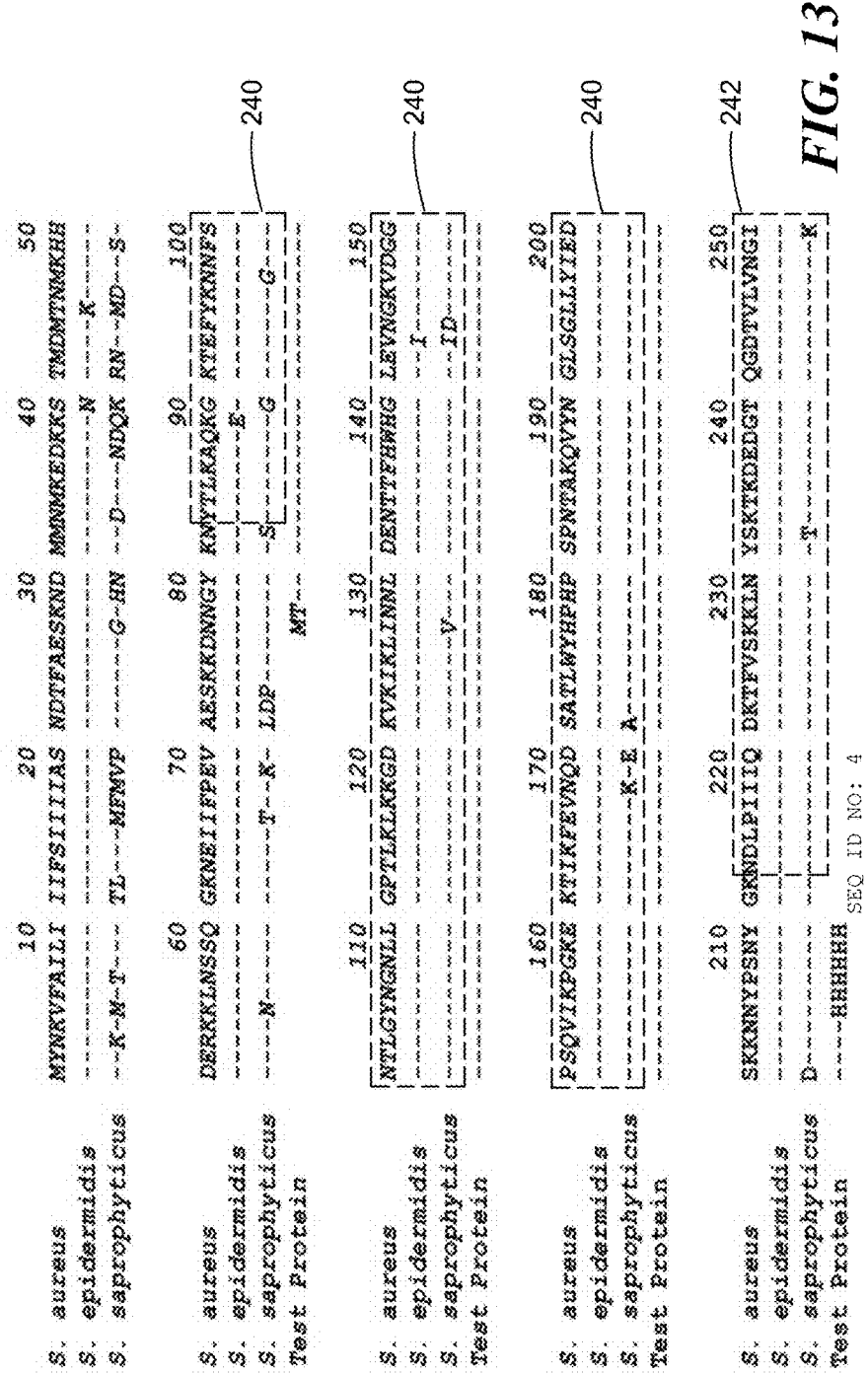
FIG. 13 is a homology diagram comparing protein sequences of three pathogenic *Staphylococcus* species.
Figure 14:
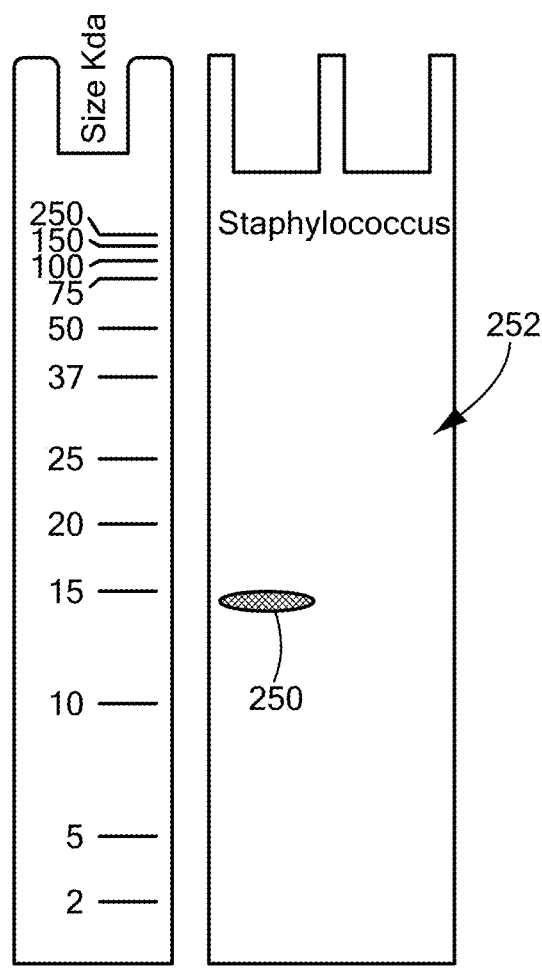
FIG. 14 shows an example of a Western Blot for a defined *Staphylococcus* surrogate protein having a predetermined sequence that has been subjected to sterilization, deimmunization, or disinfection.
Figure 15:
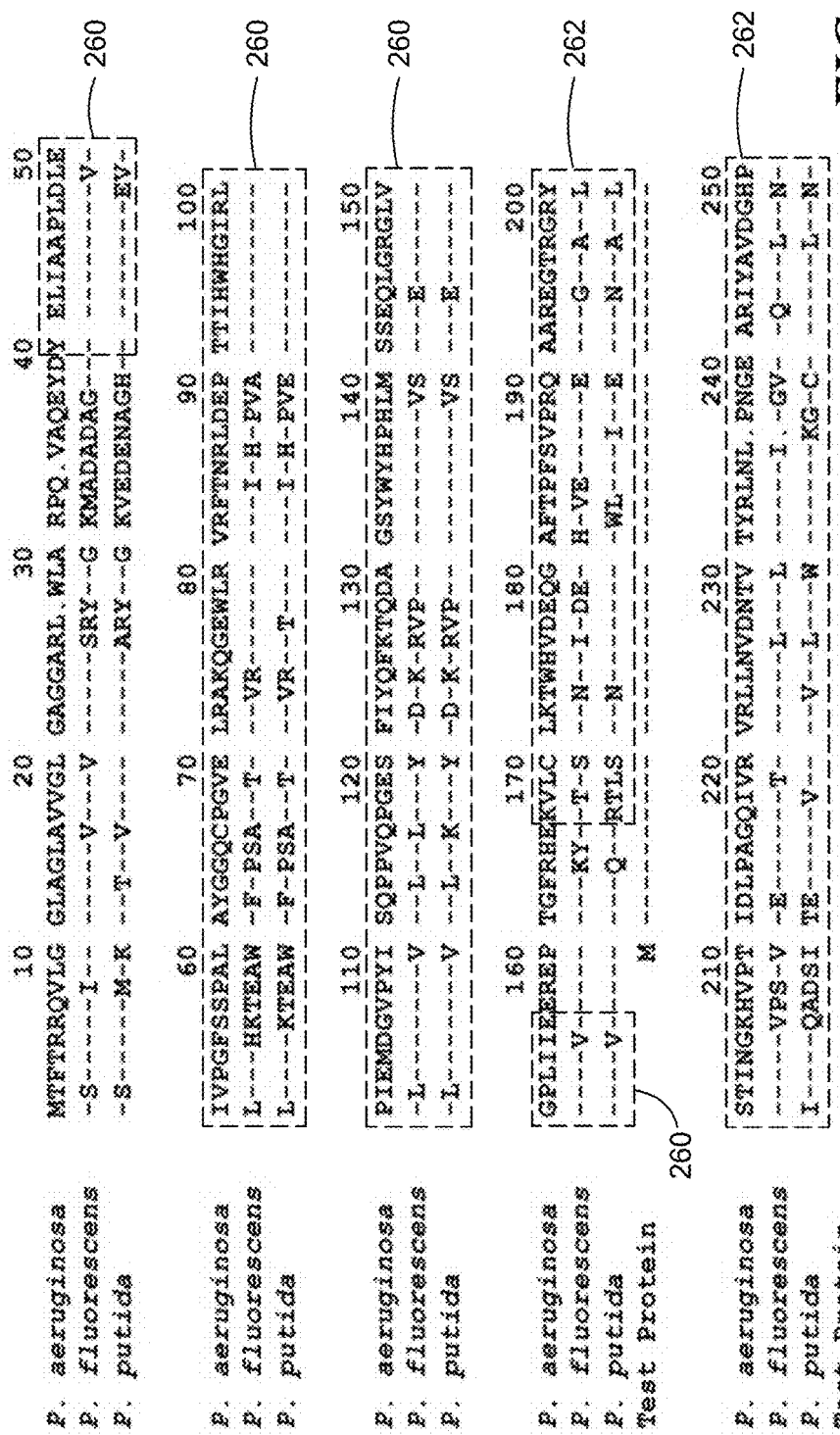
FIG. 15 is a homology diagram comparing protein sequences of a research *Pseudomonas* species and two pathogenic *Pseudomonas* species.

To design the synthetic defined *Mycobacterium* surrogate protein having SEQ ID NO: 3, the specific amino acids from the proteins listed in Table 7 were aligned to determine amino acid sequence regions that are highly homologous in all evaluated *Mycobacterium* species as shown in FIG. 11. The protein encoded by the suf 1 loci includes three cupredoxin domains that are indicated at 230 for domain 1, 232 for domain 2, and 234 for domain 3. In the *Mycobacterium* genus, domain 2, indicated at 232, shows high homology between *Mycobacterium* species so SEQ ID NO: 3 above was used to for the design for synthetic defined *Mycobacterium* surrogate protein to be created for the *Mycobacterium* test and the corresponding peptide for the defined *Mycobacterium* surrogate protein discussed above was used for a polyclonal antibody for use by Western Blot analysis.

Example 11: Developing Western Test to Qualify Ability to Destroy *Mycobacterium* Test Protein One purpose of developing the defined *Mycobacterium* surrogate protein is to provide a method for rapidly determining the effectiveness of sterilization, deimmunization, and/or disinfection by a device, such as a sterilization device, a deimmunization device, or a disinfection device. The method for rapidly determining effective sterilization, deimmunization, and/or disinfection preferably includes multiple steps including at least: 1) preparing the defined *Mycobacterium* surrogate protein test samples, 2) subjecting the defined *Mycobacterium* surrogate protein test samples to sterilization, deimmunization, or disinfection, and 3) using Western Blot or similar analysis to visualize the effects of sterilization, deimmunization, and/or disinfection of synthetic defined *Mycobacterium* surrogate protein test samples. Successful sterilization, deimmunization, and/or disinfection has occurred when all the synthetic defined *Mycobacterium* surrogate protein test samples are fragmented and as a result of the protein fragmentation, none remains to bind to the visualization antibodies indicating the defined *Mycobacterium* protein was destroyed. If sterilization, deimmunization, and/or disinfection was not successful, protein bands will be see on the Western Blot analysis.

Following the process more fully described for the Prion test, a similar process was followed to create the *Mycobacterium* sterilization, deimmunization, and/or disinfection test. First, to create the sample for the test using the defined *Mycobacterium* surrogate protein, DNA encoding the amino acid SEQ ID NO: 3 above was synthesized and cloned into standard vectors both for *E. coli* and yeast expression. Using standard techniques, large quantities of protein were produced in *E. coli* or yeast and isolated by standard recombinant methods. Using a nickel column, a full-length synthetic *Mycobacterium* surrogate protein (171 amino acids long) was isolated. To create the samples having the *Mycobacterium* surrogate protein to qualify sterilization, deimmunization, and/or disinfection the samples were dried onto small filter papers, dried inside small tubes or a surface of an object subjected to sterilization, deimmunization, and/or disinfection, e.g., using cycles of applying a solvent and microwave energy as disclosed in the '469 patent application.

Figure 16:
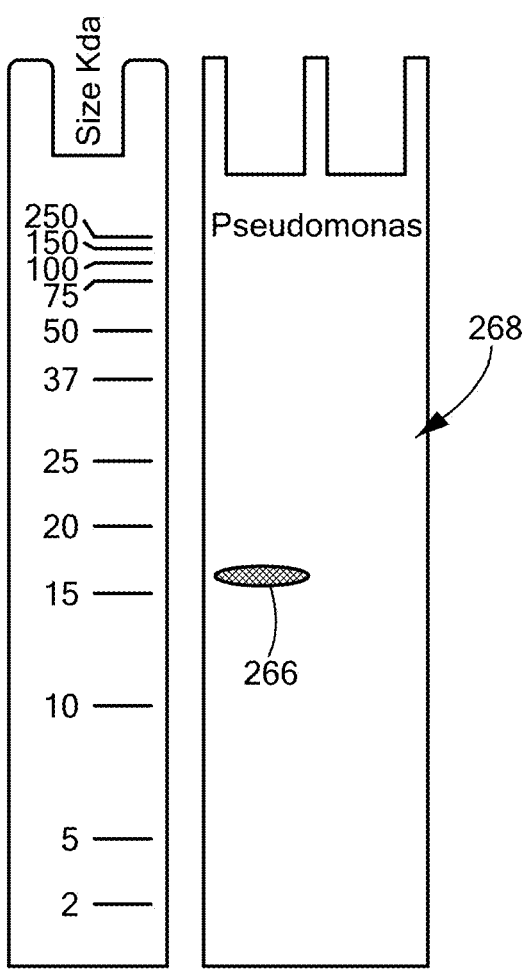
FIG. 16 shows an example of a Western Blot for a defined *Pseudomonas* surrogate protein having a predetermined sequence that has been subjected to sterilization, deimmunization, or disinfection.

After sterilization, deimmunization, and/or disinfection the treated *Mycobacterium* surrogate protein samples were transferred to tubes, denatured and separated by size and transferred to nylon membrane before being permanently cross-linked to the membrane. The final steps include incubating the nylon membrane with a primary antibody that specifically binds to the protein of interest. In the experiments discussed herein, the primary anti-suf I loci protein antibody was a rabbit polyclonal antibody that was raised against a synthetic peptide discussed above for SEQ ID NO: 3 for *Mycobacterium* above residues. For added sensitivity, addition antibodies, both monoclonal and polyclonal, were raised against the other synthetic peptide(s). For the Western Blot Analysis, a secondary antibody may be a HRP-labelled goat anti-rabbit to enable visualization of the protein fragments, both intact and fragmented. If the *Mycobacterium* surrogate proteins have completely fragmented no bands will be visualize on the Western blot. Very small fragments and amino acids will be too small to be retained on the gel. When successful sterilization, deimmunization, and/or disinfection has occurred, the visualized Western blot has a dark ban in the untreated control sample, e.g., indicated at 236, FIG. 12, and a complete absence of any bands for the *Mycobacterium* surrogate protein sample subjected to sterilization, deimmunization, or disinfection indicates successful sterilization, deimmunization, or disinfection, e.g., indicated at 238.

Example 12: Comparing Amino Acid Sequence of Multiple Members of the *Staphylococcus* Genus It is important to qualify the ability of a sterilization device, a deimmunization device, or a disinfection device to destroy bacteria of any *Staphylococcus* species that may be contaminating medical equipment or supplies. In this example, a defined quantity of the defined *Staphylococcus* surrogate protein having the predetermined SEQ ID NO: 4 discussed above is subjected to sterilization, deimmunization, or disinfection to rapidly determine the effectiveness of the sterilization, deimmunization, or disinfection using Western Blot analysis, protein array analysis, or similar type analysis and the antibody specific for the defined *Staphylococcus* surrogate protein. In this example, to protect the human operators of the test, the synthetic defined *Staphylococcus* surrogate protein needs to incorporate critical characteristics of *Staphylococcus* proteins that are critical for the survival and growth of members of the *Staphylococcus* genus while avoiding organisms that can infect humans.

To design the synthetic defined *Staphylococcus* surrogate protein having SEQ ID NO: 4, a protein analysis was conducted comparing the amino acid sequences of the sup loci gene from multiple species of the *Staphylococcus* genus shown in Table 2 above. In this example, the Sequence IDs (found in Pubmed, www.ncbi.nlm.nih.gov/Pubmed/) for the suf I loci proteins, multiple *Staphylococcus* species, used for the comparative are shown in Table 8 below:

TABLE 8

(*Staphylucoccus*). Sequences used to determine regions of high homology in Suf I locus of multiple *Staphylucoccus* Species.

| Species | Sequence ID |
|---|---|
| *Staphylucoccus aureus* | WP_000282432.1 |
| *Staphylucoccus epidermidis* | WP_023567454.1 |
| *Staphylucoccus saprophyticus* | OEK13316.1 |

The protein produced by the suf I loci is fundamental to survival and growth of a wide range of spores, bacteria and fungus. In species of the *Staphylococcus* genus, the protein product of the suf I loci is called cueO and is critical for many live stages including strongly contributing to cell survival and growth To design the synthetic defined *Staphylococcus* surrogate protein, the specific amino acids from the proteins listed in Table 8 were aligned to determine amino acid sequence regions that are highly homologous in all evaluated *Staphylococcus* species as shown in FIG. 13. The protein encoded by the suf 1 loci includes three cupredoxin domains that are indicated at 240 for domain 1, 242 for domain 2, and 244 for domain 3. In the *Staphylococcus* genus, domain 2 indicated at 242 shows high homology between *Staphylococcus* species, so SEQ ID NO: 4 above was used to for the design of the synthetic defined *Staphylococcus* surrogate protein to be created for the *Staphylococcus* test and the corresponding peptide discussed above was used for a polyclonal antibody for use by Western Blot analysis.

Example 13: Developing Western Test to Qualify Ability to Destroy *Staphylococcus* Test Protein One purpose of developing the defined *Staphylococcus* surrogate protein is to provide a method for rapidly determining the effectiveness of sterilization, deimmunization, and/or disinfection device, such as sterilization device, deimmunization device, or disinfection device and/or supplies. The method for rapidly determining effective sterilization, deimmunization, and/or disinfection includes multiple steps including at least: 1) preparing synthetic defined *Staphylococcus* surrogate protein test samples, 2) subjecting the defined *Staphylococcus* surrogate protein test samples to sterilization, deimmunization, and/or disinfection, and 3) using Western Blot or similar analysis to visualize the effects of sterilization, deimmunization, and/or disinfection of defined *Staphylococcus* surrogate protein test samples of the defined surrogate protein. Successful sterilization has occurred when all the defined *Staphylococcus* surrogate protein test samples are fragmented and as a result of the protein fragmentation, none remains to bind to the visualization antibodies indicating the defined *Staphylococcus* surrogate protein was destroyed. If sterilization, deimmunization, and/or disinfection was not successful, protein bands will be see on the Western Blot analysis.

Following the process more fully described for the Prion test, a similar process was followed to create the *Staphylococcus* sterilization, deimmunization, or disinfection test. First to create the sample for the test using the synthetic defined *Staphylococcus* surrogate protein, DNA encoding the amino acid SEQ ID NO: 4 above was synthesized and cloned into standard vectors both for *E. coli* and yeast expression. Using standard techniques, large quantities of the defined *Staphylococcus* surrogate protein were produced in *E. coli* or yeast and isolated by standard recombinant methods. Using a nickel column, a full-length defined *Staphylococcus* surrogate protein (171 amino acids long) was isolated. To create the samples having the synthetic defined *Staphylococcus* surrogate protein to qualify sterilization, deimmunization, and/or disinfection the samples were dried onto small filter papers, dried inside small tubes or a surface of an object subjected to sterilization, deimmunization, and/or disinfection e.g., using cycles of applying a solvent and microwave energy as disclosed in the '469 patent application.

After sterilization, deimmunization, and/or disinfection, the treated defined *Staphylococcus* surrogate protein samples were transferred to tubes, denatured and separated by size and transferred to nylon membrane before being permanently cross-linked to the membrane. The final steps include incubating the nylon membrane with a primary antibody that specifically binds to the *Staphylococcus* surrogate protein of interest. In the experiments discussed herein, the primary anti-suf I loci protein antibody was a rabbit polyclonal antibody that was raised against a synthetic peptide discussed above for SEQ ID NO: 4 residues. For added sensitivity, addition antibodies, both monoclonal and polyclonal, were raised against the other synthetic peptide(s). For the Western Blot analysis, a secondary antibody may be a HRP-labelled goat anti-rabbit to enable visualization of the protein fragments, both intact and fragmented. If the defined *Staphylococcus* surrogate proteins have completely fragmented no bands will be visualize on the Western blot. Very small fragments and amino acids will be too small to be retained on the gel. When successful sterilization, deimmunization, and/or disinfection occurred, the visualized Western blot has a dark ban in the untreated control sample, indicated at 250, FIG. 14, and a complete absence of any bands for defined *Staphylococcus* surrogate protein sample subjected to sterilization, deimmunization, or disinfection indicates successful sterilization, deimmunization, or disinfection, indicated at 252.

Example 14: Comparing Amino Acid Sequence of Multiple Members of the *Pseudomonas* Genus It is important to qualify the ability of a sterilization device, a deimmunization device or disinfection device to destroy bacteria of any *Pseudomonas* species that may be contaminating medical equipment or supplies. In this example, a defined *Pseudomonas* surrogate protein quantity of the defined surrogate protein having a predetermined SEQ ID NO: 5 discussed above is subjected to sterilization, deimmunization, or disinfection to rapidly determine the effectiveness of the sterilization, deimmunization, or disinfection using Western Blot analysis, protein array analysis, or similar type analysis, and using an antibody specific for the defined *Pseudomonas* surrogate protein shown above. In this example, to protect the human operators of the test, the defined *Pseudomonas* surrogate protein needs to incorporate critical characteristics of *Pseudomonas* proteins that are critical for the survival and growth of members of the *Pseudomonas* genus while avoiding organisms that can infect humans.

To design the synthetic defined *Pseudomonas* surrogate protein having SEQ ID NO: 5, a protein analysis was conducted comparing the amino acid sequences of the suf loci gene from multiple species of the *Pseudomonas* genus shown in Table 2 above. In this example, the Sequence IDs (found in Pubmed, www.ncbi.nlm.nih.gov/Pubmed/) for the suf I loci Table 9 below:

TABLE 9

*Pseudomonas*. Sequences used to determine regions of high homology in suf 1 locus of multiple *Pseudomonas* Species.

| Species | Sequence ID |
|---|---|
| *Pseudomonas aeruginosa* | WP_023096478.1 |
| *Pseudomonas fluorescens* | WP_003227851.1 |
| *Pseudomonas putida* | WP_019750583.1 |

The protein produced by the suf 1 loci is fundamental to survival and growth of a wide range of spores, bacteria and fungus. In species of the *Pseudomonas* genus, the protein product of the suf 1 loci is called cumA and is critical for many live stages including strongly contributing to the cell survival and growth To design the defined *Pseudomonas* surrogate protein, the specific amino acids from the proteins listed in Table 9 were aligned to determine amino acid sequence regions that are highly homologous in all evaluated *Pseudomonas* species as shown in FIG. 15. The protein encoded by the suf 1 loci includes three cupredoxin domains indicated at 260 for domain 1, 262 for domain 2, and 264 for domain 3. In the *Pseudomonas* genus, domain 2, indicated at 262, shows high homology between *Pseudomonas* species so SEQ ID NO: 5 above was used to for the design of the synthetic surrogate protein to be created for the defined *Pseudomonas* surrogate protein test and the corresponding peptide shown above was used for a polyclonal antibody for use by Western Blot analysis.

Example 15: Developing Western Test to Qualify Ability to Destroy *Pseudomonas* Test Protein One purpose of developing the defined *Pseudomonas* surrogate protein test is to create a method for rapidly determining the effectiveness of sterilization, deimmunization, and/or disinfection by a device, such as a sterilization device, a deimmunization device, or a disinfection device. The method for rapidly determining effective sterilization, deimmunization, and/or disinfection preferably includes multiple steps including at least: 1) preparing synthetic defined *Pseudomonas* surrogate protein test samples, 2) subjecting the synthetic *Pseudomonas* surrogate protein test samples to sterilization, deimmunization, and/or disinfection, and 3) using Western Blot or similar analysis to visualize the effects of sterilization, deimmunization, and/or disinfection of synthetic defined *Pseudomonas* surrogate test samples. Successful sterilization has occurred when all the defined *Pseudomonas* surrogate protein test samples are fragmented and as a result of the protein fragmentation, none remains to bind to the visualization antibodies indicating the defined *Pseudomonas* surrogate protein was destroyed. If sterilization, deimmunization, and/or disinfection was not successful, protein bands will be see on the Western Blot analysis.

Following the process more fully described for the Prion test, a similar process was followed to create the defined *Pseudomonas* sterilization, deimmunization and/or disinfection test. First, to create the sample for the test using the defined *Pseudomonas* surrogate protein, DNA encoding the amino acid SEQ ID NO: 5 defined above was synthesized and cloned into standard vectors both for *E. coli* and yeast expression. Using standard techniques, large quantities of the defined *Pseudomonas* surrogate protein were produced in *E. coli* or yeast and isolated by standard recombinant methods. Using a nickel column, a full-length synthetic defined *Pseudomonas* surrogate protein (171 amino acids long) was isolated. To create the samples having the synthetic defined surrogate protein to qualify sterilization, deimmunization, and/or disinfection of the samples were dried onto small filter papers, dried inside small tubes or a surface of an object subjected to sterilization, deimmunization, and/or disinfection, e.g., using cycles of applying a solvent and microwave energy as disclosed in the '469 patent application.

After sterilization, deimmunization, and/or disinfection, the treated defined *Pseudomonas* surrogate protein samples were transferred to tubes, denatured and separated by size and transferred to nylon membrane before being permanently cross-linked to the membrane. The final steps include incubating the nylon membrane with a primary antibody that specifically binds to the defined *Pseudomonas* surrogate protein. In the experiments discussed herein, the primary anti-suf 1 loci protein antibody was a rabbit polyclonal antibody that was raised against a synthetic peptide discussed above for SEQ ID NO: 5 residues. For added sensitivity, addition antibodies, both monoclonal and polyclonal, were raised against the other synthetic peptide(s). For the Western Blot Analysis, a secondary antibody may be a HRP-labelled goat anti-rabbit to enable visualization of the protein fragments, both intact and fragmented. If the synthetic defined *Pseudomonas* surrogate proteins have completely fragmented no bands will be visualize on the Western blot. Very small fragments and amino acids will be too small to be retained on the gel. When successful sterilization, deimmunization, or disinfection occurred, the visualized Western blot has a dark ban in the untreated control sample, e.g., indicated at 266, FIG. 16, and a complete absence of any bands for the defined *Pseudomonas* surrogate protein sample subjected to sterilization, deimmunization, or disinfection indicates successful sterilization, deimmunization, or disinfection, indicated at 268.

Example 16: Comparing Amino Acid Sequence of Multiple Members of the *Trichophyton* Genus It is important to qualify the ability of a sterilization device, a deimmunization device, and/or a disinfection device to destroy bacteria of any *Trichophyton* species that may be contaminating medical equipment. In this example, a defined quantity of the defined *Trichophyton* surrogate protein having a predetermined SEQ ID NO: 6 discussed above is subjected to sterilization, deimmunization, or disinfection to rapidly determine the effectiveness of the sterilization, deimmunization, or disinfection using Western Blot analysis, protein array analysis, or similar type analysis and using the antibody specific for the defined *Trichophyton* surrogate protein. In this example, to protect the human operators of the test, the synthetic defined *Trichophyton* surrogate protein needs to incorporate critical characteristics of *Trichophyton* proteins that are critical for the survival and growth of members of the *Trichophyton* genus while avoiding organisms that can infect humans.

To design the synthetic defined *Trichophyton* surrogate protein having the SEQ ID NO: 6, a protein analysis was conducted comparing the amino acid sequences of the suf I loci gene from multiple species of the *Trichophyton* genus shown in Table 2 above. In this example, the Sequence IDs (found in Pubmed, www.ncbi.nhn.nih.gov/Pubmed/) for the suf I loci proteins, multiple *Trichophyton* species, used for the comparative are shown in Table 10 below:

TABLE 10

*Trichophyton*. Sequences used to determine regions of high homology in suf 1 locus of *Trichophyton* Species.

| Species | Sequence ID |
|---|---|
| *Trichophyton rubrum* | XP_003236812.1 |
| *Trichophyton tonsurane* | EGD95875.1 |

Figure 17:
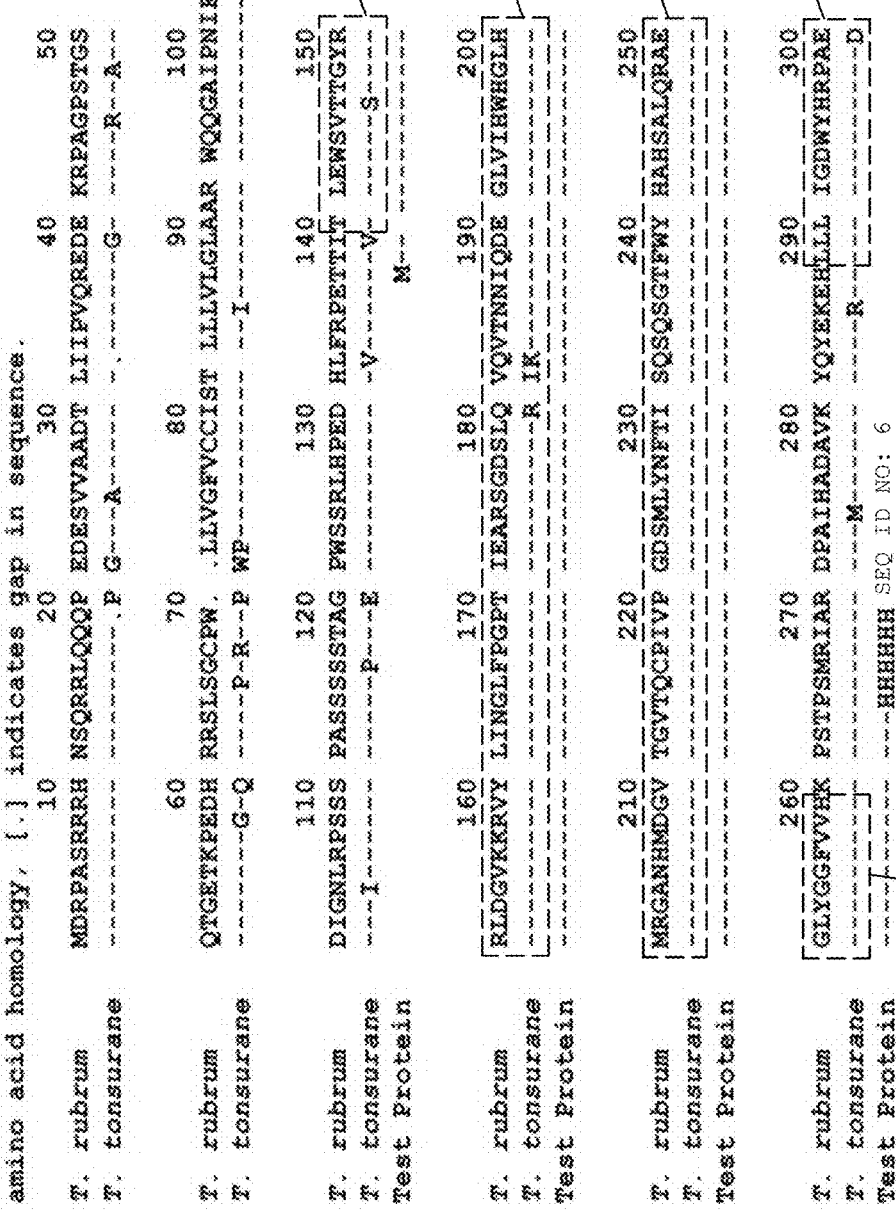
FIG. 17 is a homology comparing protein sequences of two pathogenic *Trichophyton* species.

The protein produced by the suf 1 loci is fundamental to survival and growth of a wide range of spores, bacteria and fungus. In species of the *Trichophyton* genus, the protein product of the suf 1 loci is called laccase and is critical for many live stages including strongly contributing to cell survival and growth To design the synthetic defined *Trichophyton* surrogate protein, the specific amino acids from the proteins listed in Table 10 above were aligned to determine amino acid sequence regions that are highly homologous in all evaluated *Trichophyton* species as shown in FIG. 17. The protein encoded by the suf 1 loci includes three cupredoxin domains that are indicated at 270 for domain 1, 272 for domain 2, and 274 for domain 3. In the *Trichophyton* genus, domain 2, indicated at 272, shows high homology between *Trichophyton* species so SEQ ID NO: 6 above was used to for the design of the synthetic defined *Trichophyton* surrogate protein to be created for the *Trichophyton* test and the corresponding peptide discussed above was used for a polyclonal antibody for use by Western Blot analysis.

Example 17: Developing Western Test to Qualify Ability to Destroy *Trichophyton* Test Protein One purpose of developing the defined *Trichophyton* surrogate protein is to provide a method for rapidly determining the effectiveness of sterilization, deimmunization, and/or disinfection by a device, such as sterilization device, a deimmunization device, or a disinfection device. The method for rapidly determining effective sterilization, deimmunization, or disinfection preferably includes multiple steps including at least: 1) preparing synthetic defined *Trichophyton* surrogate protein test samples, 2) subjecting the defined *Trichophyton* surrogate protein test samples to sterilization, deimmunization, or disinfection, and 3) using Western Blot or similar analysis to visualize the effects of sterilization, deimmunization, or disinfection of defined *Trichophyton* surrogate protein test samples. Successful sterilization, deimmunization, or disinfection has occurred when all the defined *Trichophyton* surrogate protein test samples are fragmented and as a result of the protein fragmentation, none remains to bind to the visualization antibodies indicating the defined *Trichophyton* surrogate protein was destroyed. If sterilization, deimmunization and/or disinfection was not successful, protein bands will be see on the Western Blot analysis.

Following the process more fully described for the Prion test, a similar process was followed to create the *Trichophyton* sterilization, deimmunization and/or disinfection test. First, to create the sample for the test using the synthetic defined *Trichophyton* surrogate protein, DNA encoding the amino acid SEQ ID NO: 7 above was synthesized and cloned into standard vectors both for *E. coli* and yeast expression. Using standard techniques, large quantities of defined *Trichophyton* surrogate protein were produced in *E. coli* or yeast and isolated by standard recombinant methods. Using a nickel column, a full-length synthetic defined *Trichophyton* surrogate protein (171 amino acids long) was isolated. To create the samples having the synthetic defined *Trichophyton* surrogate protein to qualify sterilization, deimmunization, or disinfection, the defined *Trichophyton* surrogate protein samples were dried onto small filter papers, dried inside small tubes or a surface of an object subjected to sterilization, deimmunization and/or disinfection, e.g., using cycles of applying a solvent and microwave energy as disclosed in the '469 patent application.

Figure 18:
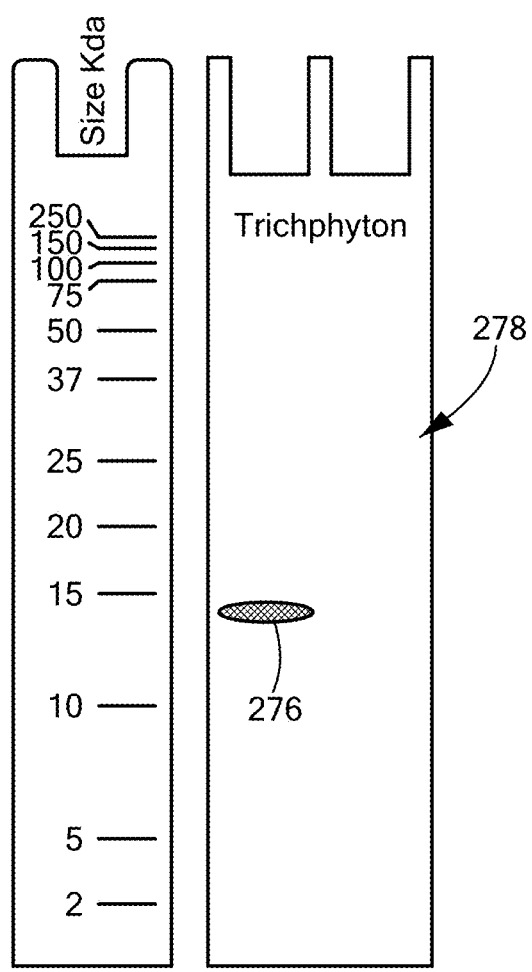
FIG. 18 shows an example of a Western Blot for a defined *Trichophyton* surrogate protein having a predetermined sequence that has been subjected to sterilization, deimmunization, or disinfection.
Figure 19:
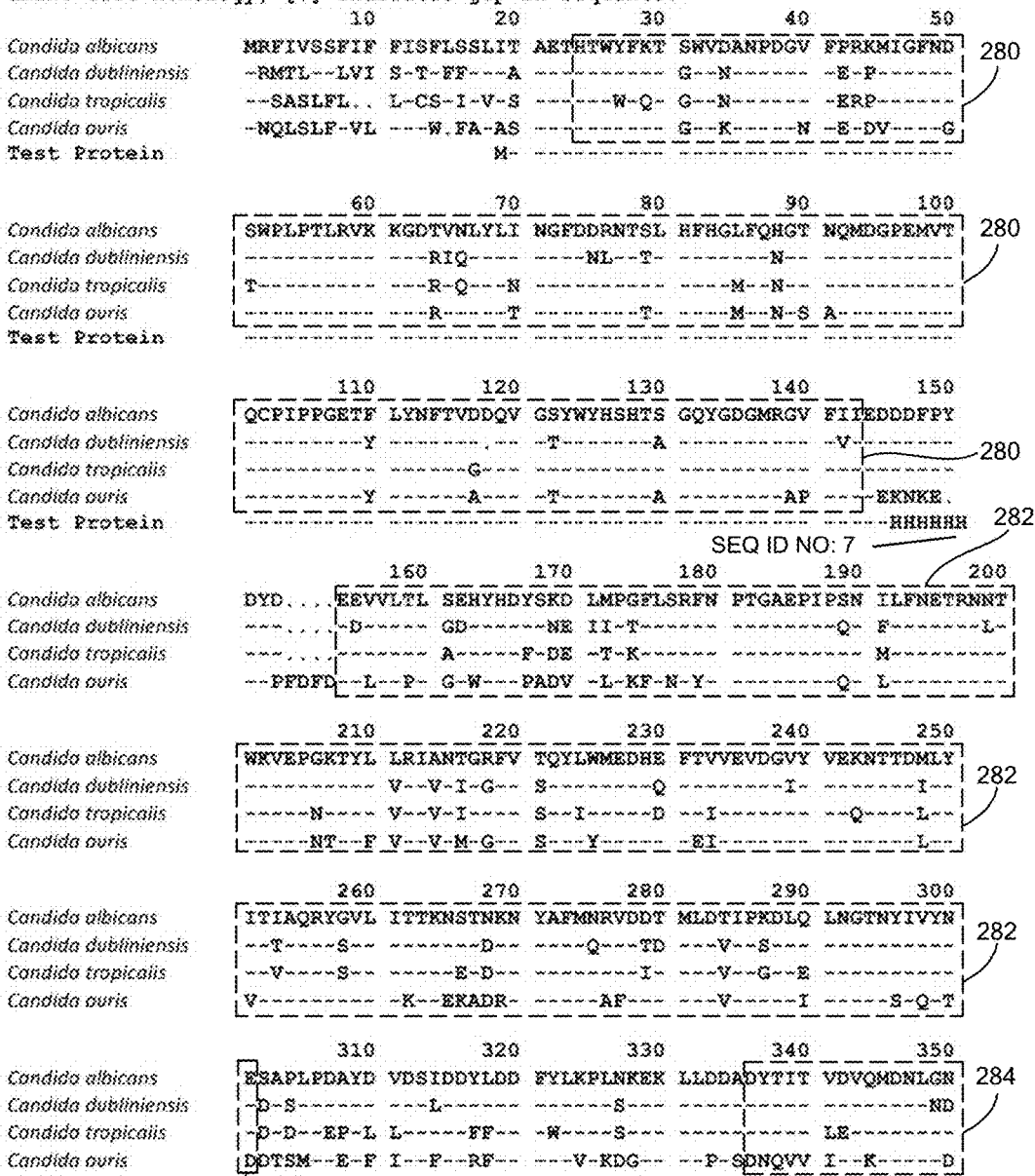
FIG. 19 is a homology comparing protein sequences of four pathogenic *Candida* species.
Figure 20:
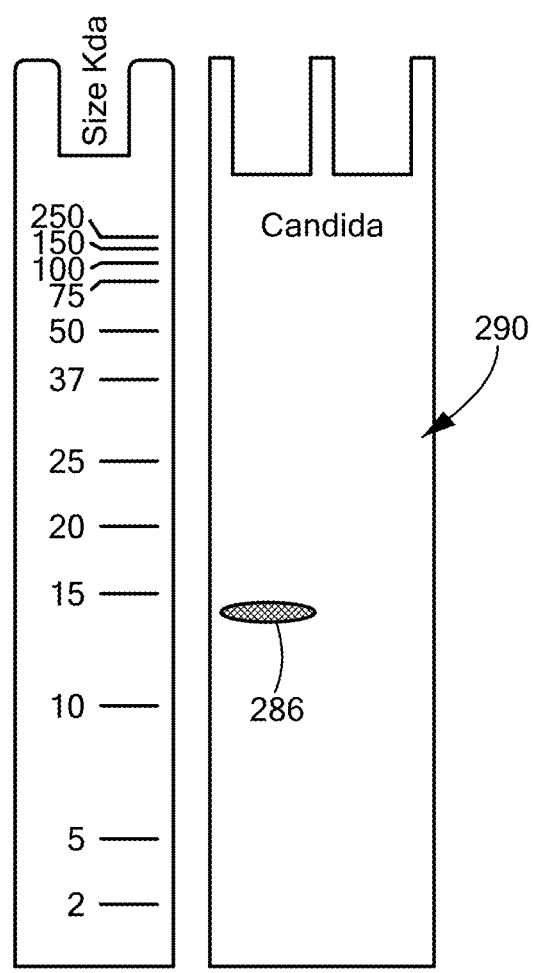
FIG. 20 shows an example of a Western Blot for a defined *Candida* surrogate protein having a predetermined sequence that has been subjected to sterilization, deimmunization, or disinfection.
Figure 21:
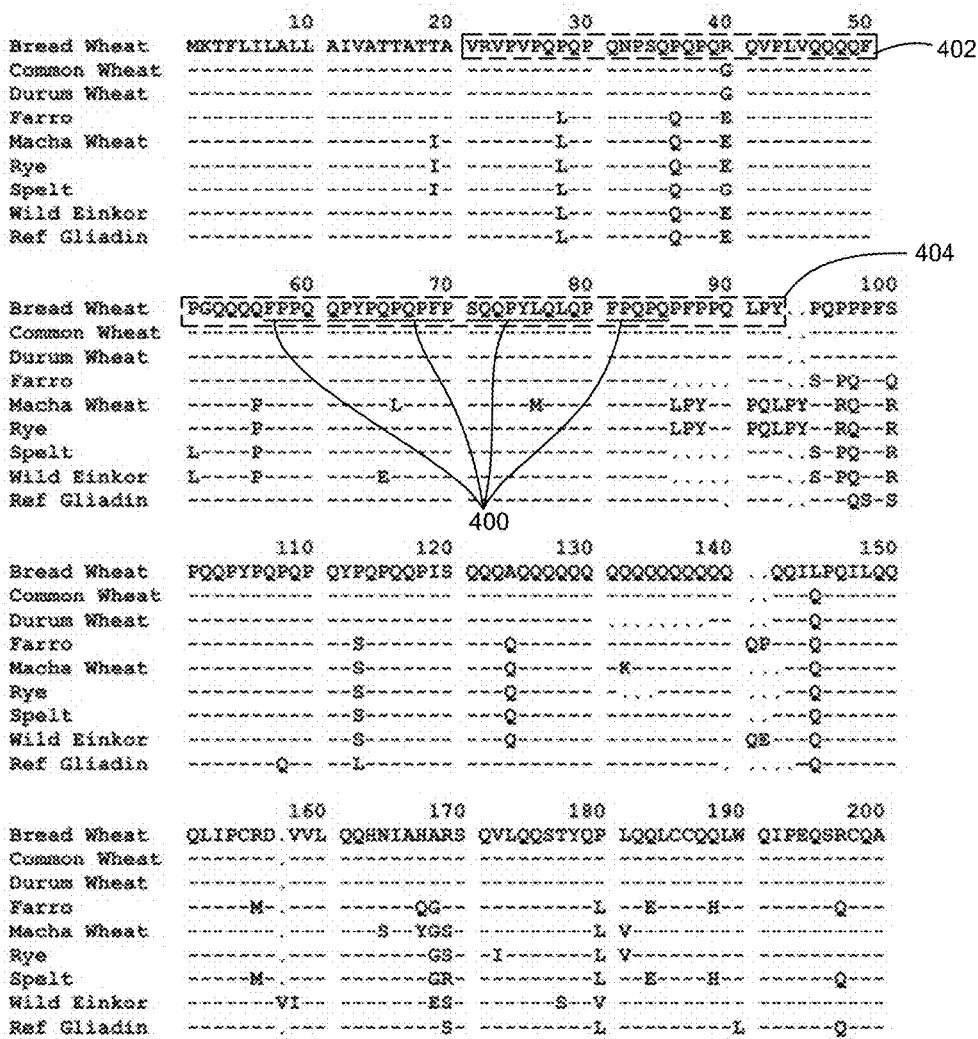
FIG. 21 is a homology comparing protein sequences of α-Gliadin from many species of commonly consumed grains.
Figure 22:
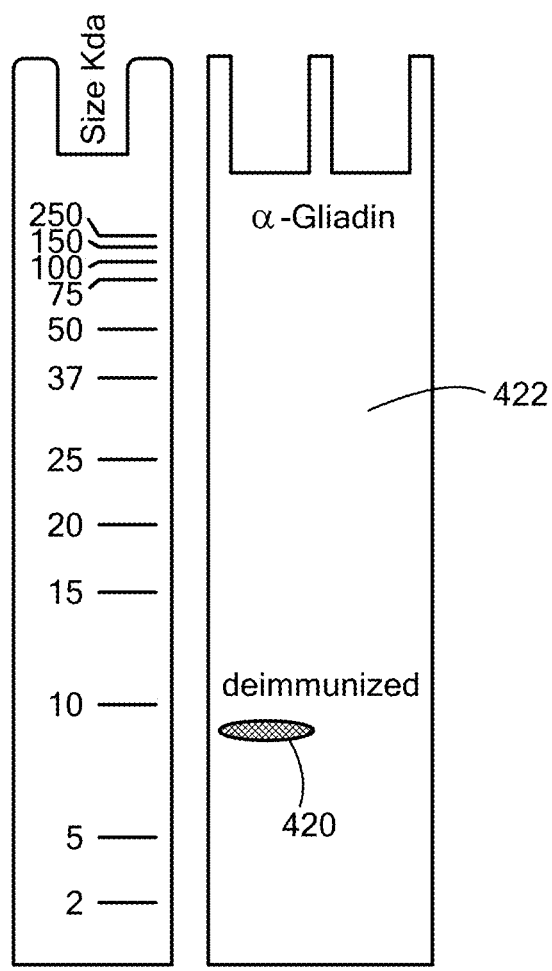
FIG. 22 shows an example of a Western Blot for a defined α-Gliadin surrogate protein having a predetermined sequence that has been subjected to sterilization, deimmunization, or disinfection.

After sterilization, deimmunization, or disinfection, the treated *Trichophyton* samples were transferred to tubes, denatured and separated by size and transferred to nylon membrane before being permanently cross-linked to the membrane. The final steps include incubating the nylon membrane with a primary antibody that specifically binds to the protein of interest. In the experiments discussed herein, the primary anti-suf 1 loci protein antibody was a rabbit polyclonal antibody that was raised against a synthetic peptide discussed above for SEQ ID NO: 6 residues. For added sensitivity, addition antibodies, both monoclonal and polyclonal, were raised against the other synthetic peptide(s). For the Western Blot analysis, a secondary antibody may be a HRP-labelled goat anti-rabbit to enable visualization of the protein fragments, both intact and fragmented. If the proteins have completely fragmented no bands will be visualize on the Western blot. Very small fragments and amino acids will be too small to be retained, on the gel. When successful sterilization, deimmunization, or disinfection has occurred, the visualized Western blot has a dark ban in the untreated control sample, e.g., indicated at 276, FIG. 18, and a complete absence of any bands for the defined *Trichophyton* surrogate protein sample subjected to sterilization, deimmunization, or disinfection indicates successful sterilization, deimmunization, or disinfection, indicated at 278.

Example 18: Comparing Amino Acid Sequence of Multiple Members of the *Candida* Genus It is important to qualify the ability of a sterilization device, a deimmunization device, or disinfection device, to destroy bacteria of any *Candida* species that may be contaminating medical equipment. In this example, a defined quantity of the defined *Candida* surrogate protein having a predetermined SEQ ID NO: 7 discussed above is subjected to sterilization, deimmunization, or disinfection to rapidly determine the effectiveness of the sterilization, deimmunization, or disinfection using Western Blot analysis, protein array analysis, or similar type analysis and the antibody specific for the defined *Candida* surrogate protein. In this example, to protect the human operators of the test, the defined *Candida* surrogate protein needs to incorporate critical characteristics of *Candida* proteins that are critical for the survival and growth of members of the *Candida* genus while avoiding organisms that can infect humans.

To design the synthetic defined *Candida* surrogate protein having the SEQ ID NO: 7, a protein analysis was conducted comparing the amino acid sequences of the suf 1 loci gene from multiple species of the *Candida* genus shown in Table 2 above. In this example, the Sequence IDs (found in Pubmed, www.ncbi.nlm.nih.gov/Pubmed/) for the suf 1 loci proteins, multiple *Candida* species, used for the comparative are shown in Table 11 below:

TABLE 11

(*Candida*). Sequences used to determine regions of high homology in Suf I locus of *Candida* Species.

| Species | Sequence ID |
| --- | --- |
| *Candida albicans* | KHC71512.1 |
| *Candida dubliniensis* | XP_002420841.1 |
| *Candida tropicalis* | XP_002548698.1 |
| *Candida auris* | XP_018169615.1 |

The protein produced by the suf I loci is fundamental to survival and growth of a wide range of spores, bacteria and fungus. In species of the *Candida* genus, the protein product of the suf I loci is called laccase and is critical for many live stages including strongly contributing to cell survival and growth To design the synthetic defined *Candida* surrogate protein, the specific amino acids from the proteins listed in Table 11 were aligned to determine amino acid sequence regions that are highly homologous in all evaluated *Candida* species as shown in FIG. 19. The protein encoded by the suf 1 loci includes three cupredoxin domains, indicated at 280 for domain 1, 282 for domain 2, and 284 for domain 3. In the *Candida* genus, domain 2, indicated at 284, shows high homology between *Candida* species so SEQ ID NO: 7 above was used to for the design of the synthetic defined *Candida* surrogate protein to be created for the *Candida* test and the corresponding peptide discussed above was used for a polyclonal antibody for use by Western Blot analysis.

Example 19: Developing Western Test to Qualify Ability to Destroy *Candida* Test Protein One purpose of developing the defined *Candida* surrogate protein test is to provide a method for rapidly determining the effectiveness of sterilization, deimmunization, and/or disinfection by a device, such as a sterilization device, a deimmunization device, or a disinfection device. The method for rapidly determining effective sterilization, deimmunization, and/or disinfection includes multiple steps preferably including at least: 1) preparing synthetic defined *Candida* surrogate protein test samples, 2) subjecting the defined *Candida* surrogate protein test samples to sterilization, deimmunization, or disinfection, and 3) using Western Blot or similar analysis to visualize the effects of sterilization, deimmunization, or disinfection of defined *Candida* surrogate protein test samples. Successful sterilization, deimmunization, or disinfection has occurred when all the defined *Candida* surrogate protein test samples are fragmented and as a result of the protein fragmentation, none remains to bind to the visualization antibodies indicating the defined *Candida* surrogate protein was destroyed. If sterilization, deimmunization, or disinfection was not successful, protein bands will be see on the Western Blot analysis.

Following the process more fully described for the Prion test, a similar process was followed to create the defined *Candida* surrogate protein sterilization, deimmunization and/or disinfection test. First, to create the sample for the synthetic defined *Candida* surrogate protein test using the defined *Candida* surrogate protein, DNA encoding the amino acid SEQ ID NO: 7 was synthesized and cloned into standard vectors both for *E. coli* and yeast expression. Using standard techniques, large quantities of protein were produced in *E. coli* or yeast and isolated by standard recombinant methods. Using a nickel column, a full-length synthetic defined *Candida* surrogate protein (171 amino acids long) was isolated. To create the samples having the synthetic defined *Candida* surrogate protein to qualify sterilization, deimmunization, or disinfection, the samples having the defined *Candida* surrogate protein were dried onto small filter papers, dried inside small tubes or a surface of an object subjected to sterilization, deimmunization, and/or disinfection, e.g., using cycles of applying a solvent and microwave energy as discussed in the '469 patent application.

After sterilization, deimmunization, or disinfection, the treated defined *Candida* surrogate protein samples were transferred to tubes, denatured and separated by size and transferred to nylon membrane before being permanently cross-linked to the membrane. The final steps include incubating the nylon membrane with a primary antibody that specifically binds to the defined *Candida* surrogate protein. In the experiments discussed herein, the primary anti-suf 1 loci protein antibody was a rabbit polyclonal antibody that was raised against a synthetic peptide discussed above for SEQ ID NO: 7 residues. For added sensitivity, addition antibodies, both monoclonal and polyclonal, were raised against the other synthetic peptide(s). For the Western Blot analysis, a secondary antibody may be a HRP-labelled goat anti-rabbit to enable visualization of the protein fragments, both intact and fragmented. If the proteins have completely fragmented no bands will be visualize on the Western blot. Very small fragments and amino acids will be too small to be retained on the gel. When successful sterilization, deimmunization, or disinfection has occurred, the visualized Western blot has a dark ban in the untreated control sample, indicated at 286, FIG. 20, and a complete absence of any bands for the defined *Candida* surrogate protein sample subjected to sterilization, deimmunization, or disinfection indicates successful sterilization, deimmunization, or disinfection, indicated at 290.

Example 20: Immobilizing Proteins onto a Solid Surface

Many processes and solid substrates are well known in the art for immobilizing proteins onto a solid surface. In this example, glass slides were obtained having round wells created by printing the glass with highly water-repellent mark, e.g., as shown by multi-well glass slides 130, 134, FIG. 2, or multi-well glass slide 152, FIG. 3. In this example, the glass slides were washed with acetone and milli-Q water before soaking overnight in 1 M NaOH (room temperature). To create amino silane-treated slides, washed slides using milli-Q water and 99.5% ethanol, were treated with 3-aminopropyltriethoxysilane for 2 hours at room temperature, washed with milli-Q water, and baked for 2 hr. at 100° C. The multi-well slides were soaked in 1% (v/v) glutaraldehyde overnight at 37° C. to produce glutaraldehyde-treated slides. The slides were then incubated overnight at 37° C. in chitosan (0.05% (w/v)) dissolved in 0.1 M acetic acid buffer (pH 5.0) supplemented with 0.25 mM sodium azide. The treated slides were rinsed twice with 0.1 M acetic acid buffer (pH 5) and then three times with water before being soaked in 1% (v/v) glutaraldehyde overnight at 37° C. The slides were incubated overnight at 37° C. in a 0.05% (w/v) solution of N-(5-Amino-1-carboxy pentyl) iminodiacetic acid (AB-NTA) in 0.1 M HEPES buffer (pH 8.0), then rinsed 3 times with milli-Q water. The slides were then soaked in blocking solution (1% (v/v) glycine) for 1 h at 37° C., then rinsed 3 times with milli-Q water, 3 times with 0.5 M NiCl2, and 3 times with milli-Q water to produce Ni-NTA immobilized slides ready for protein immobilization.

In this example, the defined *Clostridium* surrogate protein having SEQ ID NO: 1 was diluted in TG buffer (50 mM Tris-HCl (pH 8.0), 10% (v/v) glycerol) to 200 μg/ml. Different quantities of the defined *Clostridium* surrogate protein, e.g., 200 ng, 100 ng, 50 ng, 25 ng, 12.5 ng, 6.25 ng, 3.125 ng, 1.562 ng, 0.781 ng and 0 ng, were spotted in individual wells, e.g., the wells exemplarily indicated at 132 and 136, FIG. 2, and incubated for 60 min in a moist, dark chamber and finished by washing with TG buffer. After subjecting the slides 130 and 134 to sterilization, deimmunization, or disinfection using cycles of a solvent and electromagnetic radiation, e.g., microwaves as disclosed in the '469 patent application, slides 130 and 134 were incubated with anti-*Clostridium* antibodies discussed above raised against the peptide selected from SEQ ID NO: 1. To visualize the amount of the defined *Clostridium* surrogate protein remaining after sterilization, deimmunization, or disinfection, the slides were then treated with anti-Ig antibody labeled with the fluorescence dye fluorescence isothiocynate (FITC). A matched slide that was not sterilized in this example, slide 130, was used as a control for the protein array analysis. Using a fluorescence microscope with camera, the loss of protein can be visualized that can be detected with the specific anti-*Clostridium* antibodies. With additional fluorescence detection equipment, such as automated readers, increasing sensitivity and titration of detection can be added. An example of successful sterilization, deimmunization and/or disinfection is indicated at 140, for slide 134, FIG. 2, when compared against control slide 130 which visibly shows color, indicated by the shading in wells 132. Confirmatory tests were conducted by including samples of intact *C. sporogenes* using cycles of a solvent and electromagnetic energy or microwaves, e.g., as disclosed in the '469 patent application. After treatment, the intact bacteria were processed following industry standard protocols. Similar methods may be used for any of Examples 6 to 18 above.

Example 21: Comparing Amino Acid Sequence of α-Gliadin from Appropriate Human Consumed Grains To develop a test to qualify the ability of a sterilization device, deimmunization, or disinfection to destroy medically important immunogenic proteins, such as α-gliadin, that may be contaminating medical equipment, the following experiments were conducted. In this example, to rapidly detect effective deimmunization, a defined quality of an isolated protein needs to be deimmunized with a deimmunization device, e.g., using cycles of a combination of a solvent and electromagnetic microwaves radiation, e.g., microwaves, as disclosed in the '469 patent application and then evaluated by Western Blot analysis using an antibody specific for the protein. To design a candidate protein to serve as the representative defined surrogate α-gliadin protein having a predetermined sequence, the translated sequences of representative α-gliadin genes from many commonly consumed human grains were aligned. See Table 13 and Table 14 below. Gliadin protein is the immunogenic component of gluten and must be avoided by Celiac patients. FIG. 21 shows the amino acid numbering aligned with an example of Bread wheat α-Gliadin. The underline region, indicated at 400, is the polypeptide that acts as common immunogen in a majority of Celiac Patients. Regions at 402, 404 indicate protein region used to design test immunogen reagent.

TABLE 13

Sequence ID of α-Gliadin Proteins or Prolamins in Common Grains Used to Design Recombinant Protein Sequence.

| Common Name | Species Name | Sequence ID Number w/Link |
|---|---|---|
| Bread Wheat | *Triticum aestivum* | pir\|\|A27319 |
| Common Wheat | *Triticum sphaerococcum* | ABQ45316.1 |
| Durum wheat/Pasta Wheat | *Triticum turgidum* subsp. *durum* | ADA83698.1 |
| Farro/Emmer Wheat | *Triticum dicoccon* | AKC91191.1 |
| Macha Wheat | *Triticum macha* | AKC91223.1 |
| Rye | *Secale cereale* | AFK32718.1 |
| Spelt/Dinkel Wheat | *Triticum spelta* | APU92351.1 |
| Red Wild Einkor | *Triticum urartu* | AKC91171.1 |
| Precursor αGliadin Bateman et al 2004 | *Triticum aestivum* | Q41545 |

TABLE 14

Additional α-Gliadin Protein Sequences that could be used to design Recombinant Protein.

| Species | Common | Sequence ID | Species | Common Name | Sequence ID |
|---|---|---|---|---|---|
| *Triticum aestivum* | Bread Wheat | pir\|\|A27319<br>P04726.1 | *Triticum turgidum* subsp. *durum* | Durum wheat, pasta wheat or macaroni wheat | ADA83698.1<br>ADA83690.1 |
| | | AED99851.1 | *Triticum dicoccon* | Emmer wheat or Farro | AKC91191.1 |
| | | SCW25751.1 | *Triticum urartu* | red wild einkor | AKC91171.1 |
| | | AHY37812.1 | *Triticum macha* | Macha wheat | AKC91223.1 |
| | | AHY37818.1 | *Secale cereale* | Rye | AFK32718.1 |
| | | AFX69612.1 | | | |
| | | ABQ52118.1<br>AFX69616.1<br>AFX69586.1 | *Aegilops tauschii* | Tausch's goatgrass | AFX69602.1<br>XP_020186089.1<br>AKC91337.1 |
| *Triticum sphaerococcum* | Common wheat | ABQ45316.1 | | | ABQ52112.1 |
| *Triticum spelta* | Spelt or dinkel wheat | APU92351.1<br>APU92675.1<br>APU92554.1 | *Aegilops sharonensis* | Sharon goatgrass | AMS25611.1<br>AMS25610.1<br>AMS25614.1 |
| | | APU92300.1 | *Aegilops searsii* | Goatgrass | AKC91312.1 |
| | | APU92425.1 | | | AKC91311.1 |
| | | APU92357.1 | *Aegilops speltoides* | Goatgrass | AHN85624.1 |
| | | APU92415.1 | *Aegilops speltoides* | Goatgrass | AHN85626.1 |
| | | APU92583.1 | *Aegilops uniaristata* | Goatgrass | AEV55370.1 |
| | | APU92336.1<br>APU92334.1 | *Thinopyrum bessarabicum* | Wild *Thinopyrum* grasses | ADP94197.1 |

In this example, the defined α-Gliadin surrogate protein has the following predetermined sequence:
For α-Gliadin:

```
                                                            (SEQ ID NO: 8)
        10          20          30          40          50
MKTVRVPVPQ  PQPQNPSQPQ  PQRQVPLVQQ  QQFPGQQQQF  PPQQPYPQPQ

PFPSQQPYLQ  LQPFPQPQPF  PPQLPYHHHH  HH
```

The peptide used for the development of monoclonal or polyclonal antibody used by Western Blot analysis for the above sequence is:

```
                                    (SEQ ID NO: 24)
          FPPQQPYPQPQPFPSQQPYLQLQPFPQPQ
```

A fragment of this peptide (KLQPFPQPELPYPQPQ (SEQ ID NO: 25)) in form is the medically important immunogen is CD.

If the defined α-Gliadin surrogate proteins have completely fragmented, no bands will be visualized on the Western Blot. Very small fragments in amino acid would be too small to be retained on the gel. When successful deimmunization, in this example, has occurred, the visualized Western Blot has a dark band in the untreated control sample, e.g., indicated at 420, FIG. 22, and a complete absence of any bands for the defined α-Gliadin surrogate protein sample subject to deimmunization indicates successful deimmunization, e.g., indicated at 422.

Confirmatory tests were conducted by including samples of intact wheat flour using a combination of cycles of a solvent and microwaves, e.g., as disclosed in the '469 patent application. After treatment, the intact wheat flour samples were processed following industry standard protocols to test for the presence of gluten in food stuffs.

Although specific features of the invention are shown in some drawings and not in others, this is for convenience only as each feature may be combined with any or all of the other features in accordance with the invention. The words "including", "comprising", "having", and "with" as used herein are to be interpreted broadly and comprehensively and are not limited to any physical interconnection. Moreover, any embodiments disclosed in the subject application are not to be taken as the only possible embodiments. Other embodiments will occur to those skilled in the art and are within the following claims.

In addition, any amendment presented during the prosecution of the patent application for this patent is not a disclaimer of any claim element presented in the application as filed: those skilled in the art cannot reasonably be expected to draft a claim that would literally encompass all possible equivalents, many equivalents will be unforeseeable at the time of the amendment and are beyond a fair interpretation of what is to be surrendered (if anything), the rationale underlying the amendment may bear no more than a tangential relation to many equivalents, and/or there are many other reasons the applicant cannot be expected to describe certain insubstantial substitutes for any claim element amended.

SEQUENCE LISTING

<160> NUMBER OF SEQ ID NOS: 63

<210> SEQ ID NO 1
<211> LENGTH: 171
<212> TYPE: PRT
<213> ORGANISM: Clostridium sporogenes

<400> SEQUENCE: 1

```
Met Tyr Asn Tyr Thr Ser Ala Lys Tyr Glu Val Pro Ile Ala Ile Gln
1               5                   10                  15

Asp Arg Ser Phe Asn Glu Asp Gly Ser Leu Asn Phe Pro Ser Glu Gly
            20                  25                  30

Asp Asn Pro Thr Ile His Pro Tyr Trp Gln Pro Glu Phe Phe Gly Asp
        35                  40                  45

Thr Ile Met Val Asn Gly Arg Val Trp Pro Asn Met Asn Val Asp Met
    50                  55                  60

Thr Arg Tyr Arg Phe Arg Leu Leu Asn Gly Ser Asn Ala Arg Phe Tyr
65                  70                  75                  80

Asn Leu Lys Phe Ser Asn Gly Met Gln Phe Trp Gln Ile Gly Thr Asp
                85                  90                  95

Gly Gly Tyr Leu Asn Lys Pro Val Pro Leu Thr Ser Leu Leu Ile Ser
            100                 105                 110

Pro Gly Glu Arg Ala Asp Ile Leu Val Asp Phe Thr Glu Ile Pro Ala
        115                 120                 125

Gly Thr Arg Ile Ile Leu Asn Asn Asp Ala Asn Ala Pro Tyr Pro Thr
    130                 135                 140

Gly Asp Ala Pro Asp Lys Asp Thr Thr Gly Gln Ile Met Gln Phe Thr
145                 150                 155                 160

Val Gln His Asn Asp His His His His His His
                165                 170
```

<210> SEQ ID NO 2
<211> LENGTH: 169
<212> TYPE: PRT
<213> ORGANISM: Bacillus subtilis

<400> SEQUENCE: 2

```
Met Thr Leu Glu Lys Thr Tyr Tyr Glu Val Thr Met Glu Glu Cys Thr
1               5                   10                  15

His Gln Leu His Arg Asp Leu Pro Pro Thr Arg Leu Trp Gly Tyr Asn
            20                  25                  30

Gly Leu Phe Pro Gly Pro Thr Ile Glu Val Lys Arg Asn Glu Asn Val
        35                  40                  45

Tyr Val Lys Trp Met Asn Asn Leu Pro Ser Thr His Phe Leu Pro Ile
    50                  55                  60

Asp His Thr Ile His His Ser Asp Ser Gln His Glu Glu Pro Glu Val
65                  70                  75                  80

Lys Thr Val Val His Leu His Gly Gly Val Thr Pro Asp Asp Ser Asp
                85                  90                  95

Gly Tyr Pro Glu Ala Trp Phe Ser Lys Asp Phe Glu Gln Thr Gly Pro
            100                 105                 110

Tyr Phe Lys Arg Glu Val Tyr His Tyr Pro Asn Gln Gln Arg Gly Ala
        115                 120                 125

Ile Leu Trp Tyr His Asp His Ala Met Ala Leu Thr Arg Leu Asn Val
    130                 135                 140

Tyr Ala Gly Leu Val Gly Ala Tyr Ile Ile His Asp Pro Lys Glu Lys
```

```
145                 150                 155                 160

Arg Leu Lys His His His His His
                165

<210> SEQ ID NO 3
<211> LENGTH: 139
<212> TYPE: PRT
<213> ORGANISM: Mycobacterium tuberculosis

<400> SEQUENCE: 3

Met Thr Gly Met Pro Glu Gly Glu Gly Val Asp Ser Asn Leu Leu Gly
1               5                   10                  15

Gly Asp Gly Gly Asp Ile Ala Tyr Pro Tyr Tyr Leu Ile Asn Gly Arg
            20                  25                  30

Ile Pro Val Ala Ala Thr Ser Phe Lys Ala Lys Pro Gly Gln Arg Ile
        35                  40                  45

Arg Ile Arg Ile Ile Asn Ser Ala Ala Asp Thr Ala Phe Arg Ile Ala
    50                  55                  60

Leu Ala Gly His Ser Met Thr Val Thr His Thr Asp Gly Tyr Pro Val
65                  70                  75                  80

Ile Pro Thr Glu Val Asp Ala Leu Leu Ile Gly Met Ala Glu Arg Tyr
                85                  90                  95

Asp Val Met Val Thr Ala Ala Gly Gly Val Phe Pro Leu Val Ala Leu
            100                 105                 110

Ala Glu Gly Lys Asn Ala Leu Ala Arg Ala Leu Leu Ser Thr Gly Ala
        115                 120                 125

Gly Ser Pro Pro Asp His His His His His
    130                 135

<210> SEQ ID NO 4
<211> LENGTH: 134
<212> TYPE: PRT
<213> ORGANISM: Staphylococcus aureus

<400> SEQUENCE: 4

Met Thr Gly Tyr Lys Asn Tyr Thr Leu Lys Ala Gln Lys Gly Lys Thr
1               5                   10                  15

Glu Phe Tyr Lys Asn Asn Phe Ser Asn Thr Leu Gly Tyr Asn Gly Asn
            20                  25                  30

Leu Leu Gly Pro Thr Leu Lys Leu Lys Gly Asp Lys Val Lys Ile
        35                  40                  45

Lys Leu Ile Asn Asn Leu Asp Glu Asn Thr Thr Phe His Trp His Gly
    50                  55                  60

Leu Glu Val Asn Gly Lys Val Asp Gly Gly Pro Ser Gln Val Ile Lys
65                  70                  75                  80

Pro Gly Lys Glu Lys Thr Ile Lys Phe Glu Val Asn Gln Asp Ser Ala
                85                  90                  95

Thr Leu Trp Tyr His Pro His Pro Ser Pro Asn Thr Ala Lys Gln Val
            100                 105                 110

Tyr Asn Gly Leu Ser Gly Leu Leu Tyr Ile Glu Asp Ser Lys Lys Asn
        115                 120                 125

His His His His His His
    130

<210> SEQ ID NO 5
<211> LENGTH: 143
<212> TYPE: PRT
```

<213> ORGANISM: Pseudomonas aeruginosa

<400> SEQUENCE: 5

```
Met Thr Gly Phe Arg His Glu Lys Val Leu Cys Leu Lys Thr Trp His
1               5                   10                  15
Val Asp Glu Gln Gly Ala Phe Thr Pro Phe Ser Val Pro Arg Gln Ala
            20                  25                  30
Ala Arg Glu Gly Thr Arg Gly Arg Tyr Ser Thr Ile Asn Gly Lys His
        35                  40                  45
Val Pro Thr Ile Asp Leu Pro Ala Gly Gln Ile Val Arg Val Arg Leu
    50                  55                  60
Leu Asn Val Asp Asn Thr Val Thr Tyr Arg Leu Asn Pro Asn Gly Glu
65                  70                  75                  80
Ala Arg Ile Tyr Ala Val Asp Gly His Pro Val Glu Pro Arg Gly Phe
                85                  90                  95
Glu Gly Gln Tyr Trp Ile Gly Pro Gly Met Arg Leu Glu Leu Ala Leu
            100                 105                 110
Lys Val Pro Glu Ala Gly Thr Glu Leu Ser Leu Arg Asp Gly Pro Val
        115                 120                 125
Arg Leu Ala Thr Ile Arg Ser Val Ala His His His His His His
    130                 135                 140
```

<210> SEQ ID NO 6
<211> LENGTH: 133
<212> TYPE: PRT
<213> ORGANISM: Trichophyton rubrum

<400> SEQUENCE: 6

```
Met Thr Ile Thr Leu Glu Trp Ser Val Thr Thr Gly Tyr Arg Arg Leu
1               5                   10                  15
Asp Gly Val Lys Lys Arg Val Tyr Leu Ile Asn Gly Leu Phe Pro Gly
            20                  25                  30
Pro Thr Ile Glu Ala Arg Ser Gly Asp Ser Leu Gln Val Gln Val Thr
        35                  40                  45
Asn Asn Ile Gln Asp Glu Gly Leu Val Ile His Trp His Gly Leu His
    50                  55                  60
Met Arg Gly Ala Asn His Met Asp Gly Val Thr Gly Val Thr Gln Cys
65                  70                  75                  80
Pro Ile Val Pro Gly Asp Ser Met Leu Tyr Asn Phe Thr Ile Ser Gln
                85                  90                  95
Ser Gln Ser Gly Thr Phe Trp Tyr His Ala His Ser Ala Leu Gln Arg
            100                 105                 110
Ala Glu Gly Leu Tyr Gly Gly Phe Val Val His Lys Pro Ser Thr His
        115                 120                 125
His His His His His
    130
```

<210> SEQ ID NO 7
<211> LENGTH: 133
<212> TYPE: PRT
<213> ORGANISM: Candida albicans

<400> SEQUENCE: 7

```
Met Thr Ala Glu Thr His Thr Trp Tyr Phe Lys Thr Ser Trp Val Asp
1               5                   10                  15
Ala Asn Pro Asp Gly Val Phe Pro Arg Lys Met Ile Gly Phe Asn Asp
            20                  25                  30
```

```
Ser Trp Pro Leu Pro Thr Leu Arg Val Lys Lys Gly Asp Thr Val Asn
        35                  40                  45

Leu Tyr Leu Ile Asn Gly Phe Asp Asp Arg Asn Thr Ser Leu His Phe
 50                  55                  60

His Gly Leu Phe Gln His Gly Thr Asn Gln Met Asp Gly Pro Glu Met
 65                  70                  75                  80

Val Thr Gln Cys Pro Ile Pro Pro Gly Glu Thr Phe Leu Tyr Asn Phe
                 85                  90                  95

Thr Val Asp Asp Gln Val Gly Ser Tyr Trp Tyr His Ser His Thr Ser
                100                 105                 110

Gly Gln Tyr Gly Asp Gly Met Arg Gly Val Phe Ile Ile Glu Asp His
                115                 120                 125

His His His His His
                130

<210> SEQ ID NO 8
<211> LENGTH: 82
<212> TYPE: PRT
<213> ORGANISM: Unknown
<220> FEATURE:
<223> OTHER INFORMATION: surrogate protein sequence

<400> SEQUENCE: 8

Met Lys Thr Val Arg Val Pro Val Pro Gln Pro Gln Pro Gln Asn Pro
 1               5                  10                  15

Ser Gln Pro Gln Pro Gln Arg Gln Val Pro Leu Val Gln Gln Gln Gln
                 20                  25                  30

Phe Pro Gly Gln Gln Gln Gln Phe Pro Pro Gln Gln Pro Tyr Pro Gln
            35                  40                  45

Pro Gln Pro Phe Pro Ser Gln Gln Pro Tyr Leu Gln Leu Gln Pro Phe
         50                  55                  60

Pro Gln Pro Gln Pro Phe Pro Pro Gln Leu Pro Tyr His His His His
 65                  70                  75                  80

His His

<210> SEQ ID NO 9
<211> LENGTH: 208
<212> TYPE: PRT
<213> ORGANISM: Artificial Sequence
<220> FEATURE:
<223> OTHER INFORMATION: surrogate protein 9

<400> SEQUENCE: 9

Lys Lys Arg Pro Lys Pro Gly Gly Trp Asn Thr Gly Gly Ser Arg Tyr
 1               5                  10                  15

Pro Gly Gln Gly Ser Pro Gly Gly Asn Arg Tyr Pro Pro Gln Gly Gly
                 20                  25                  30

Thr Trp Gly Gln Pro His Gly Gly Gly Trp Gly Gln Pro His Gly Gly
             35                  40                  45

Ser Trp Gly Gln Pro His Gly Gly Ser Trp Gly Gln Pro His Gly Gly
         50                  55                  60

Gly Trp Gly Gln Gly Gly Gly Thr His Asn Gln Trp Asn Lys Pro Ser
 65                  70                  75                  80

Lys Pro Lys Thr Asn Leu Lys His Val Ala Gly Ala Ala Ala Ala Gly
                 85                  90                  95

Ala Val Val Gly Gly Leu Gly Gly Tyr Met Leu Gly Ser Ala Met Ser
                100                 105                 110
```

Arg Pro Met Ile His Phe Gly Asn Asp Trp Glu Asp Arg Tyr Tyr Arg
            115                 120                 125

Glu Asn Met Tyr Arg Tyr Pro Asn Gln Val Tyr Tyr Arg Pro Val Asp
    130                 135                 140

Gln Tyr Ser Asn Gln Asn Asn Phe Val His Asp Cys Val Asn Ile Thr
145                 150                 155                 160

Ile Lys Gln His Thr Val Thr Thr Thr Thr Lys Gly Glu Asn Phe Thr
                165                 170                 175

Glu Thr Asp Val Lys Met Met Glu Arg Val Val Glu Gln Met Cys Val
            180                 185                 190

Thr Gln Tyr Gln Lys Glu Ser Gln Ala Tyr Tyr Asp Gly Arg Arg Ser
        195                 200                 205

<210> SEQ ID NO 10
<211> LENGTH: 24
<212> TYPE: PRT
<213> ORGANISM: Clostridium sporogenes

<400> SEQUENCE: 10

Lys Tyr Glu Val Pro Ile Ala Ile Gln Asp Arg Ser Phe Asn Glu Asp
1               5                   10                  15

Gly Ser Leu Asn Phe Pro Ser Glu
            20

<210> SEQ ID NO 11
<211> LENGTH: 24
<212> TYPE: PRT
<213> ORGANISM: Clostridium sporogenes

<400> SEQUENCE: 11

Tyr Leu Asn Lys Pro Val Pro Leu Thr Ser Leu Leu Ile Ser Pro Gly
1               5                   10                  15

Glu Arg Ala Asp Ile Leu Val Asp
            20

<210> SEQ ID NO 12
<211> LENGTH: 24
<212> TYPE: PRT
<213> ORGANISM: Bacillus subtilis

<400> SEQUENCE: 12

Gln Arg Gly Ala Ile Leu Trp Tyr His Asp His Ala Met Ala Leu Thr
1               5                   10                  15

Arg Leu Asn Val Tyr Ala Gly Leu
            20

<210> SEQ ID NO 13
<211> LENGTH: 24
<212> TYPE: PRT
<213> ORGANISM: Bacillus subtilis

<400> SEQUENCE: 13

Gln Leu His Arg Asp Leu Pro Pro Thr Arg Leu Trp Gly Tyr Asn Gly
1               5                   10                  15

Leu Phe Pro Gly Pro Thr Ile Glu
            20

<210> SEQ ID NO 14
<211> LENGTH: 29
<212> TYPE: PRT

<213> ORGANISM: Mycobacterium tuberculosis

<400> SEQUENCE: 14

```
Asp Thr Ala Phe Arg Ile Ala Leu Ala Gly His Ser Met Thr Val Thr
1               5                   10                  15

His Thr Asp Gly Tyr Pro Val Ile Pro Thr Glu Val Asp
            20                  25
```

<210> SEQ ID NO 15
<211> LENGTH: 25
<212> TYPE: PRT
<213> ORGANISM: Mycobacterium tuberculosis

<400> SEQUENCE: 15

```
Val Phe Pro Leu Val Ala Leu Ala Glu Gly Lys Asn Ala Leu Ala Arg
1               5                   10                  15

Ala Leu Leu Ser Thr Gly Ala Gly Ser
            20                  25
```

<210> SEQ ID NO 16
<211> LENGTH: 29
<212> TYPE: PRT
<213> ORGANISM: Staphylococcus aureus

<400> SEQUENCE: 16

```
Asn Phe Ser Asn Thr Leu Gly Tyr Asn Gly Asn Leu Leu Gly Pro Thr
1               5                   10                  15

Leu Lys Leu Lys Lys Gly Asp Lys Val Lys Ile Lys Leu
            20                  25
```

<210> SEQ ID NO 17
<211> LENGTH: 23
<212> TYPE: PRT
<213> ORGANISM: Staphylococcus aureus

<400> SEQUENCE: 17

```
Lys Phe Glu Val Asn Gln Asp Ser Ala Thr Leu Trp Tyr His Pro His
1               5                   10                  15

Pro Ser Pro Asn Thr Ala Lys
            20
```

<210> SEQ ID NO 18
<211> LENGTH: 24
<212> TYPE: PRT
<213> ORGANISM: Pseudomonas aeruginosa

<400> SEQUENCE: 18

```
Asp Leu Pro Ala Gly Gln Ile Val Arg Val Arg Leu Leu Asn Val Asp
1               5                   10                  15

Asn Thr Val Thr Tyr Arg Leu Asn
            20
```

<210> SEQ ID NO 19
<211> LENGTH: 20
<212> TYPE: PRT
<213> ORGANISM: Pseudomonas aeruginosa

<400> SEQUENCE: 19

```
Gln Tyr Trp Ile Gly Pro Gly Met Arg Leu Glu Leu Ala Leu Lys Val
1               5                   10                  15

Pro Glu Ala Gly
            20
```

-continued

<210> SEQ ID NO 20
<211> LENGTH: 24
<212> TYPE: PRT
<213> ORGANISM: Trichophyton rubrum

<400> SEQUENCE: 20

Tyr Arg Arg Leu Asp Gly Val Lys Lys Arg Val Tyr Leu Ile Asn Gly
1               5                   10                  15

Leu Phe Pro Gly Pro Thr Ile Glu
            20

<210> SEQ ID NO 21
<211> LENGTH: 23
<212> TYPE: PRT
<213> ORGANISM: Trichophyton rubrum

<400> SEQUENCE: 21

Thr Gln Cys Pro Ile Val Pro Gly Asp Ser Met Leu Tyr Asn Phe Thr
1               5                   10                  15

Ile Ser Gln Ser Gln Ser Gly
            20

<210> SEQ ID NO 22
<211> LENGTH: 23
<212> TYPE: PRT
<213> ORGANISM: Candida albicans

<400> SEQUENCE: 22

Gly Phe Asn Asp Ser Trp Pro Leu Pro Thr Leu Arg Val Lys Lys Gly
1               5                   10                  15

Asp Thr Val Asn Leu Tyr Leu
            20

<210> SEQ ID NO 23
<211> LENGTH: 22
<212> TYPE: PRT
<213> ORGANISM: Candida albicans

<400> SEQUENCE: 23

Trp Tyr Phe Lys Thr Ser Trp Val Asp Ala Asn Pro Asp Gly Val Phe
1               5                   10                  15

Pro Arg Lys Met Ile Gly
            20

<210> SEQ ID NO 24
<211> LENGTH: 29
<212> TYPE: PRT
<213> ORGANISM: Unknown
<220> FEATURE:
<223> OTHER INFORMATION: alpha-Gliadin

<400> SEQUENCE: 24

Phe Pro Pro Gln Gln Pro Tyr Pro Gln Pro Gln Phe Pro Ser Gln
1               5                   10                  15

Gln Pro Tyr Leu Gln Leu Gln Pro Phe Pro Gln Pro Gln
            20                  25

<210> SEQ ID NO 25
<211> LENGTH: 16
<212> TYPE: PRT
<213> ORGANISM: Unknown
<220> FEATURE:

<223> OTHER INFORMATION: alpha-Gliadin

<400> SEQUENCE: 25

Lys Leu Gln Pro Phe Pro Gln Pro Glu Leu Pro Tyr Pro Gln Pro Gln
1               5                   10                  15

<210> SEQ ID NO 26
<211> LENGTH: 204
<212> TYPE: PRT
<213> ORGANISM: Homo sapiens

<400> SEQUENCE: 26

Lys Lys Arg Pro Lys Pro Gly Gly Trp Asn Thr Gly Gly Ser Arg Tyr
1               5                   10                  15

Pro Gly Gln Gly Ser Pro Gly Gly Asn Arg Tyr Pro Pro Gln Gly Gly
                20                  25                  30

Gly Gly Trp Gly Gln Pro His Gly Gly Trp Gly Gln Pro His Gly
            35                  40                  45

Gly Gly Trp Gly Gln Pro His Gly Gly Trp Gly Gln Pro His Gly
50                  55                  60

Gly Gly Trp Gly Gln Gly Gly Thr His Ser Gln Trp Asn Lys Pro
65                  70                  75                  80

Ser Lys Pro Lys Thr Asn Met Lys His Met Ala Gly Ala Ala Ala
                85                  90                  95

Gly Ala Val Val Gly Gly Leu Gly Gly Tyr Met Leu Gly Ser Ala Met
                100                 105                 110

Ser Arg Pro Ile Ile His Phe Gly Ser Asp Tyr Glu Asp Arg Tyr Tyr
                115                 120                 125

Arg Glu Asn Met His Arg Tyr Pro Asn Gln Val Tyr Tyr Arg Pro Met
130                 135                 140

Asp Glu Tyr Ser Asn Gln Asn Asn Phe Val His Asp Cys Val Asn Ile
145                 150                 155                 160

Thr Ile Lys Gln His Thr Val Thr Thr Thr Lys Gly Glu Asn Phe
                165                 170                 175

Thr Glu Thr Asp Val Lys Met Met Glu Arg Val Val Glu Gln Met Cys
                180                 185                 190

Ile Thr Gln Tyr Glu Arg Glu Ser Gln Ala Tyr Tyr
                195                 200

<210> SEQ ID NO 27
<211> LENGTH: 204
<212> TYPE: PRT
<213> ORGANISM: Macaca mulatta

<400> SEQUENCE: 27

Lys Lys Arg Pro Lys Pro Gly Gly Trp Asn Thr Gly Gly Ser Arg Tyr
1               5                   10                  15

Pro Gly Gln Gly Ser Pro Gly Gly Asn Arg Tyr Pro Pro Gln Gly Gly
                20                  25                  30

Gly Gly Trp Gly Gln Pro His Gly Gly Trp Gly Gln Pro His Gly
            35                  40                  45

Gly Gly Trp Gly Gln Pro His Gly Gly Trp Gly Gln Pro His Gly
50                  55                  60

Gly Gly Trp Gly Gln Gly Gly Thr His Asn Gln Trp Asn Lys Pro
65                  70                  75                  80

Ser Lys Pro Lys Thr Ser Met Lys His Met Ala Gly Ala Ala Ala Ala
                85                  90                  95

Gly Ala Val Val Gly Gly Leu Gly Gly Tyr Met Leu Gly Ser Ala Met
            100                 105                 110

Ser Arg Pro Ile Ile His Phe Gly Asn Asp Tyr Glu Asp Arg Tyr Tyr
            115                 120                 125

Arg Glu Asn Met Tyr Arg Tyr Pro Asn Gln Val Tyr Tyr Arg Pro Val
130                 135                 140

Asp Gln Tyr Ser Asn Gln Asn Asn Phe Val His Asp Cys Val Asn Ile
145                 150                 155                 160

Thr Ile Lys Gln His Thr Val Thr Thr Thr Lys Gly Glu Asn Phe
            165                 170                 175

Thr Glu Thr Asp Val Lys Met Met Glu Arg Val Val Glu Gln Met Cys
            180                 185                 190

Ile Thr Gln Tyr Glu Lys Glu Ser Gln Ala Tyr Tyr
            195                 200

<210> SEQ ID NO 28
<211> LENGTH: 210
<212> TYPE: PRT
<213> ORGANISM: Felis catus

<400> SEQUENCE: 28

Lys Lys Arg Pro Lys Pro Gly Gly Gly Trp Asn Thr Gly Gly Ser Arg
1               5                   10                  15

Tyr Pro Gly Gln Gly Ser Pro Gly Gly Asn Arg Tyr Pro Pro Gln Gly
            20                  25                  30

Gly Gly Gly Trp Gly Gln Pro His Gly Gly Gly Trp Gly Gln Pro His
        35                  40                  45

Gly Gly Gly Trp Gly Gln Pro His Gly Gly Gly Trp Gly Gln Pro His
    50                  55                  60

Gly Gly Gly Gly Trp Gly Gln Gly Gly Ser His Ser Gln Trp Asn Lys
65                  70                  75                  80

Pro Ser Lys Pro Lys Thr Asn Met Lys His Met Ala Gly Ala Ala Ala
                85                  90                  95

Ala Gly Ala Val Val Gly Gly Leu Gly Gly Tyr Met Leu Gly Ser Ala
            100                 105                 110

Met Ser Arg Pro Ile Ile His Phe Gly Asn Asp Tyr Glu Asp Arg Tyr
        115                 120                 125

Tyr Arg Glu Asn Met Tyr Arg Tyr Pro Asn Gln Val Tyr Tyr Arg Pro
    130                 135                 140

Val Asp Gln Tyr Ser Asn Gln Asn Asn Phe Val His Asp Cys Val Asn
145                 150                 155                 160

Ile Thr Val Lys Gln His Thr Val Thr Thr Thr Thr Lys Gly Glu Asn
                165                 170                 175

Phe Thr Glu Thr Asp Met Lys Ile Met Glu Arg Val Val Glu Gln Met
            180                 185                 190

Cys Val Thr Gln Tyr Gln Lys Glu Ser Glu Ala Tyr Tyr Gln Arg Arg
        195                 200                 205

Ala Ser
    210

<210> SEQ ID NO 29
<211> LENGTH: 205
<212> TYPE: PRT
<213> ORGANISM: Canis familiaris

<400> SEQUENCE: 29

```
Lys Lys Arg Pro Lys Pro Gly Gly Gly Trp Asn Thr Gly Gly Ser Arg
1               5                   10                  15

Tyr Pro Gly Gln Gly Ser Pro Gly Gly Asn Arg Tyr Pro Pro Gln Gly
                20                  25                  30

Gly Gly Gly Trp Gly Gln Pro His Gly Gly Trp Gly Gln Pro His
            35                  40                  45

Gly Gly Gly Trp Gly Gln Pro His Gly Gly Trp Gly Gln Pro His
50                  55                  60

Gly Gly Gly Gly Trp Gly Gln Gly Gly Thr His Ser Gln Trp Asn Lys
65                  70                  75                  80

Pro Ser Lys Pro Lys Thr Asn Met Lys His Val Ala Gly Ala Ala Ala
                85                  90                  95

Ala Gly Ala Val Val Gly Gly Leu Gly Gly Tyr Leu Leu Gly Ser Ala
            100                 105                 110

Met Ser Arg Pro Ile Ile His Phe Gly Asn Asp Cys Glu Asp Arg Tyr
        115                 120                 125

Tyr Arg Glu Asn Met Tyr Arg Tyr Pro Asn Gln Val Tyr Tyr Arg Ser
        130                 135                 140

Val Asp Gln Tyr Asn Asn Gln Ser Thr Phe Val His Asp Cys Val Asn
145                 150                 155                 160

Ile Thr Val Lys Gln His Thr Val Thr Thr Thr Lys Gly Glu Asn
                165                 170                 175

Phe Thr Glu Thr Asp Ile Lys Met Met Glu Arg Val Val Glu Gln Met
                180                 185                 190

Cys Ile Thr Gln Tyr Gln Arg Glu Ser Glu Ala Tyr Tyr
            195                 200                 205

<210> SEQ ID NO 30
<211> LENGTH: 213
<212> TYPE: PRT
<213> ORGANISM: Bos taurus

<400> SEQUENCE: 30

Lys Lys Arg Pro Lys Pro Gly Gly Gly Trp Asn Thr Gly Gly Ser Arg
1               5                   10                  15

Tyr Pro Gly Gln Gly Ser Pro Gly Gly Asn Arg Tyr Pro Pro Gln Gly
                20                  25                  30

Gly Gly Gly Trp Gly Gln Pro His Gly Gly Trp Gly Gln Pro His
            35                  40                  45

Gly Gly Gly Trp Gly Gln Pro His Gly Gly Trp Gly Gln Pro His
50                  55                  60

Gly Gly Gly Trp Gly Gln Pro His Gly Gly Gly Trp Gly Gln Gly
65                  70                  75                  80

Gly Thr His Gly Gln Trp Asn Lys Pro Ser Lys Pro Lys Thr Asn Met
            85                  90                  95

Lys His Val Ala Gly Ala Ala Ala Gly Ala Val Val Gly Gly Leu
            100                 105                 110

Gly Gly Tyr Met Leu Gly Ser Ala Met Ser Arg Pro Ile Ile His Phe
        115                 120                 125

Gly Ser Asp Tyr Glu Asp Arg Tyr Tyr Arg Glu Asn Met His Arg Tyr
        130                 135                 140

Pro Asn Gln Val Tyr Tyr Arg Pro Val Asp Gln Tyr Ser Asn Gln Asn
145                 150                 155                 160

Asn Phe Val His Asp Cys Val Asn Ile Thr Val Lys Glu His Thr Val
```

```
                    165                 170                 175
Thr Thr Thr Thr Lys Gly Glu Asn Phe Thr Glu Thr Asp Ile Lys Met
                180                 185                 190

Met Glu Arg Val Val Glu Gln Met Cys Ile Thr Gln Tyr Gln Arg Glu
            195                 200                 205

Ser Gln Ala Tyr Tyr
        210

<210> SEQ ID NO 31
<211> LENGTH: 205
<212> TYPE: PRT
<213> ORGANISM: Ovis aries

<400> SEQUENCE: 31

Lys Lys Arg Pro Lys Pro Gly Gly Gly Trp Asn Thr Gly Gly Ser Arg
1               5                   10                  15

Tyr Pro Gly Gln Gly Ser Pro Gly Gly Asn Arg Tyr Pro Pro Gln Gly
            20                  25                  30

Gly Gly Gly Trp Gly Gln Pro His Gly Gly Gly Trp Gly Gln Pro His
        35                  40                  45

Gly Gly Gly Trp Gly Gln Pro His Gly Gly Gly Trp Gly Gln Pro His
    50                  55                  60

Gly Gly Gly Gly Trp Gly Gln Gly Gly Ser His Ser Gln Trp Asn Lys
65                  70                  75                  80

Pro Ser Lys Pro Lys Thr Asn Met Lys His Val Ala Gly Ala Ala Ala
                85                  90                  95

Ala Gly Ala Val Val Gly Gly Leu Gly Gly Tyr Met Leu Gly Ser Ala
            100                 105                 110

Met Ser Arg Pro Ile Ile His Phe Gly Asn Asp Tyr Glu Asp Arg Tyr
        115                 120                 125

Tyr Arg Glu Asn Met Tyr Arg Tyr Pro Asn Gln Val Tyr Tyr Arg Pro
    130                 135                 140

Val Asp Arg Tyr Ser Asn Gln Asn Asn Phe Val His Asp Cys Val Asn
145                 150                 155                 160

Ile Thr Val Lys Gln His Thr Val Thr Thr Thr Lys Gly Glu Asn
                165                 170                 175

Phe Thr Glu Thr Asp Ile Lys Ile Met Glu Arg Val Val Glu Gln Met
            180                 185                 190

Cys Ile Thr Gln Tyr Gln Arg Glu Ser Gln Ala Tyr Tyr
        195                 200                 205

<210> SEQ ID NO 32
<211> LENGTH: 209
<212> TYPE: PRT
<213> ORGANISM: Mus musculus

<400> SEQUENCE: 32

Lys Lys Arg Pro Lys Pro Gly Gly Trp Asn Thr Gly Gly Ser Arg Tyr
1               5                   10                  15

Pro Gly Gln Gly Ser Pro Gly Gly Asn Arg Tyr Pro Pro Gln Gly Gly
            20                  25                  30

Gly Thr Trp Gly Gln Pro His Gly Gly Gly Trp Gly Gln Pro His Gly
        35                  40                  45

Gly Ser Trp Gly Gln Pro His Gly Ser Gly Trp Gly Gln Pro His Gly
    50                  55                  60

Gly Gly Trp Gly Gln Gly Gly Gly Thr His Asn Gln Trp Asn Lys Pro
```

```
            65                  70                  75                  80
        Ser Lys Pro Lys Thr Asn Leu Lys His Val Ala Gly Ala Ala Ala Ala
                            85                  90                  95

Gly Ala Val Val Gly Gly Leu Gly Gly Tyr Met Leu Gly Ser Ala Met
                        100                 105                 110

Ser Arg Met Ile Ile His Phe Gly Asn Asp Tyr Glu Asp Arg Tyr Tyr
                        115                 120                 125

Arg Glu Asn Met Tyr Arg Tyr Pro Asn Gln Val Tyr Tyr Arg Pro Val
                    130                 135                 140

Asp Gln Tyr Ser Asn Gln Asn Asn Phe Val His Asp Cys Val Asn Ile
        145                 150                 155                 160

Thr Ile Lys Gln His Thr Val Thr Thr Thr Lys Gly Glu Asn Phe
                        165                 170                 175

Thr Glu Thr Asp Val Lys Met Met Glu Arg Val Val Glu Gln Met Cys
                        180                 185                 190

Val Thr Gln Tyr Gln Lys Glu Ser Gln Ala Tyr Tyr Asp Gly Arg Arg
                        195                 200                 205

Ser

<210> SEQ ID NO 33
<211> LENGTH: 209
<212> TYPE: PRT
<213> ORGANISM: Rattus norvegicus

<400> SEQUENCE: 33

Lys Lys Arg Pro Lys Pro Gly Gly Trp Asn Thr Gly Gly Ser Arg Tyr
        1               5                   10                  15

Pro Gly Gln Gly Ser Pro Gly Gly Asn Arg Tyr Pro Pro Gln Ser Gly
                        20                  25                  30

Gly Thr Trp Gly Gln Pro His Gly Gly Gly Trp Gly Gln Pro His Gly
                        35                  40                  45

Gly Gly Trp Gly Gln Pro His Gly Gly Gly Trp Gly Gln Pro His Gly
                    50                  55                  60

Gly Gly Trp Ser Gln Gly Gly Gly Thr His Asn Gln Trp Asn Lys Pro
        65                  70                  75                  80

Ser Lys Pro Lys Thr Asn Leu Lys His Val Ala Gly Ala Ala Ala Ala
                            85                  90                  95

Gly Ala Val Val Gly Gly Leu Gly Gly Tyr Met Leu Gly Ser Ala Met
                        100                 105                 110

Ser Arg Met Leu Ile His Phe Gly Asn Asp Tyr Glu Asp Arg Tyr Tyr
                        115                 120                 125

Arg Glu Asn Met Tyr Arg Tyr Pro Asn Gln Val Tyr Tyr Arg Pro Val
                    130                 135                 140

Asp Gln Tyr Ser Asn Gln Asn Asn Phe Val His Asp Cys Val Asn Ile
        145                 150                 155                 160

Thr Ile Lys Gln His Thr Val Thr Thr Thr Lys Gly Glu Asn Phe
                        165                 170                 175

Thr Glu Thr Asp Val Lys Met Met Glu Arg Val Val Glu Gln Met Cys
                        180                 185                 190

Val Thr Gln Tyr Gln Lys Glu Ser Gln Ala Tyr Tyr Asp Gly Arg Arg
                        195                 200                 205

Ser

<210> SEQ ID NO 34
```

<211> LENGTH: 601
<212> TYPE: PRT
<213> ORGANISM: Clostridium sporogenes

<400> SEQUENCE: 34

| Met | Glu | Val | Asn | Pro | Leu | Asp | Pro | Lys | Leu | Ile | Pro | Lys | Tyr | Thr | Gln |
|---|---|---|---|---|---|---|---|---|---|---|---|---|---|---|---|
| 1 | | | | 5 | | | | | 10 | | | | | 15 | |

Glu Leu Val Ile Pro Pro Ser Phe Leu Pro Thr Val Cys Thr Ser Ser
                20                  25                  30

Val Ser Gly Ala Val Ser Tyr Asn Tyr Thr Val Thr Met Asn Gln Phe
            35                  40                  45

Glu Gln Gln Ile Leu Pro Pro Glu Phe Asn Pro Thr Thr Val Trp Gly
    50                  55                  60

Tyr Gly Gly Thr Ile Lys Asp Thr Ser Thr Gly Glu Glu Val Lys Phe
65                  70                  75                  80

Gln Asn Ala Pro Gly Pro Thr Phe Glu Ala Val Arg Gly Ile Pro Val
                85                  90                  95

Asn Val Lys Trp Val Asn Glu Ile Thr Ala Pro Tyr Ser Leu Ala Val
            100                 105                 110

Asp Pro Thr Met His Trp Ala Asn Pro Asn Asn Thr Pro Met Pro Pro
        115                 120                 125

Pro Pro Gly Gly Trp Pro Pro Phe Pro Gly Val Pro Glu Ala Gln
    130                 135                 140

Lys Asp Val Pro Leu Val Pro His Leu His Gly Glu Gln Ala Ser
145                 150                 155                 160

Met Phe Asp Gly Asn Pro Glu Ala Trp Trp Thr Ala Lys Gly Leu Lys
                165                 170                 175

Gly Ser Arg Tyr Ile Thr Asp Thr Phe His Tyr Leu Asn Thr Gln Glu
            180                 185                 190

Ser Thr Thr Leu Trp Tyr His Asp His Ala Leu Gly Val Thr Arg Leu
        195                 200                 205

Asn Val Val Met Gly Leu Ala Gly Phe Tyr Ile Leu Arg Asp Pro Ala
    210                 215                 220

Asn Pro Leu Asp Tyr Pro Gly Pro Leu Ile Thr Ser Ala Lys Tyr Glu
225                 230                 235                 240

Val Pro Ile Ala Ile Gln Asp Arg Ser Phe Asn Glu Asp Gly Ser Leu
                245                 250                 255

Asn Phe Pro Ser Glu Gly Asp Asn Pro Thr Ile His Pro Tyr Trp Gln
            260                 265                 270

Pro Glu Phe Phe Gly Asp Thr Ile Met Val Asn Gly Arg Val Trp Pro
        275                 280                 285

Asn Met Asn Val Asp Met Thr Arg Tyr Arg Phe Arg Leu Leu Asn Gly
    290                 295                 300

Ser Asn Ala Arg Phe Tyr Asn Leu Lys Phe Ser Asn Gly Met Gln Phe
305                 310                 315                 320

Trp Gln Ile Gly Thr Asp Gly Gly Tyr Leu Asn Lys Pro Val Pro Leu
                325                 330                 335

Thr Ser Leu Leu Ile Ser Pro Gly Glu Arg Ala Asp Ile Leu Val Asp
            340                 345                 350

Phe Thr Glu Ile Pro Ala Gly Thr Arg Ile Ile Leu Asn Asn Asp Ala
        355                 360                 365

Asn Ala Pro Tyr Pro Thr Gly Asp Ala Pro Asp Lys Asp Thr Thr Gly
    370                 375                 380

Gln Ile Met Gln Phe Thr Val Gln His Asn Asp Asp Met Thr Ile Pro 385             390             395             400

Pro Glu Leu Pro Glu Lys Leu Arg Cys Glu Pro Val Pro Lys Leu Lys
                405                 410                 415

Ser Pro Cys Lys Arg Val Leu Thr Leu Tyr Glu Ile Ala Gly Pro
            420                 425                 430

Asn Gly Pro Gln Met Val Thr Leu Asn Gly Gln Arg Trp Ala Asp Pro
                435                 440                 445

Val Ser Glu Leu Pro Val Val Gly Ser Thr Glu Trp Asn Ile Val
        450                 455                 460

Asn Leu Thr Met Asp Ala His Pro Ile His Leu His Leu Val Gln Phe
465                 470                 475                 480

Lys Ile Ala Cys Arg Gln Ala Phe Asp Val Asp Ala Tyr Thr Asn Asp
                485                 490                 495

Trp Leu Asp Leu Asn Ser Asp Ile Gly Ser Pro Pro Trp Met Thr Thr
                500                 505                 510

Pro Lys Ala Leu Cys Pro Gly Ser Tyr Ile Thr Gly Asp Asp Gln Pro
                515                 520                 525

Pro Ala Ala Asn Glu Ala Gly Trp Lys Asp Thr Val Gln Ala Phe Pro
        530                 535                 540

Gly Glu Ile Thr Arg Ile Arg Val Arg Phe Ala Pro Gln Asp Val Lys
545                 550                 555                 560

Thr Ser Cys Pro Gly Glu Asn Leu Tyr Leu Phe Asp Pro Ser Lys Gly
                565                 570                 575

Pro Gly Tyr Val Trp His Cys His Ile Leu Asp His Glu Asp Asn Asp
                580                 585                 590

Met Met Arg Pro Tyr Arg Val Phe Pro
                595                 600

<210> SEQ ID NO 35
<211> LENGTH: 598
<212> TYPE: PRT
<213> ORGANISM: Clostridium botulinum

<400> SEQUENCE: 35

Met Glu Val Asn Pro Leu Asp Pro Lys Leu Ile Pro Lys Tyr Thr Gln
1               5                   10                  15

Glu Leu Val Ile Pro Pro Ser Phe Leu Pro Thr Ile Cys Thr Ser Ser
                20                  25                  30

Val Ser Gly Ala Val Ser Tyr Asn Tyr Thr Val Thr Met Asn Gln Phe
            35                  40                  45

Glu Gln Gln Ile Leu Pro Pro Glu Phe Asn Pro Thr Thr Val Trp Gly
        50                  55                  60

Tyr Gly Gly Thr Ile Lys Asp Thr Ser Thr Gly Glu Glu Val Lys Phe
65                  70                  75                  80

Gln Asn Ala Pro Gly Pro Thr Phe Glu Ala Val Arg Asp Ile Pro Ile
                85                  90                  95

Asn Val Lys Trp Val Asn Glu Ile Thr Ala Pro Tyr Ser Leu Ala Val
                100                 105                 110

Asp Pro Thr Ile His Trp Ala Asn Pro Asn Asn Thr Pro Met Thr Pro
            115                 120                 125

Pro Pro Gly Gly Trp Pro Pro Phe Pro Pro Gly Val Pro Glu Asp Gln
        130                 135                 140

Lys Asp Val Pro Leu Val Thr His Leu His Gly Gly Glu Gln Ala Ser
145                 150                 155                 160

```
Met Phe Asp Gly Asn Pro Glu Ala Trp Trp Thr Ala Lys Gly Leu Lys
            165                 170                 175

Gly Pro Lys Tyr Ile Thr Asp Thr Phe His Tyr Pro Asn Val Gln Glu
        180                 185                 190

Ser Thr Thr Leu Trp Tyr His Asp His Ala Leu Gly Val Thr Arg Leu
            195                 200                 205

Asn Val Val Met Gly Leu Ala Gly Phe Tyr Ile Leu Arg Asp Pro Ala
210                 215                 220

Asn Pro Leu Asp Tyr Pro Gly Ser Leu Ile Thr Ser Ala Lys Tyr Glu
225                 230                 235                 240

Val Pro Ile Ala Ile Gln Asp Arg Ser Phe Asn Glu Asp Gly Ser Leu
                245                 250                 255

Asn Phe Pro Ser Glu Gly Asp Asn Pro Thr Ile His Pro Tyr Trp Gln
                260                 265                 270

Pro Glu Phe Phe Gly Asp Thr Ile Met Val Asn Gly Arg Val Trp Pro
            275                 280                 285

Asn Leu Asn Val Asp Met Thr Lys Tyr Arg Phe Arg Leu Leu Asn Gly
            290                 295                 300

Ser Asn Ala Arg Phe Tyr Asn Leu Lys Phe Ser Asn Gly Met Gln Phe
305                 310                 315                 320

Trp Gln Ile Gly Thr Asp Gly Gly Tyr Leu Asn Lys Pro Val Pro Leu
                325                 330                 335

Thr Ser Leu Leu Ile Ser Pro Gly Glu Arg Ala Asp Ile Leu Val Asp
            340                 345                 350

Phe Thr Glu Ile Pro Ala Gly Thr Lys Ile Ile Leu Asn Asn Asp Ala
            355                 360                 365

Asn Ala Pro Tyr Pro Thr Gly Asp Ala Pro Asp Lys Asp Thr Thr Gly
370                 375                 380

Gln Ile Met Gln Phe Thr Val Gln Asp Asn Met Thr Met Pro Pro Glu
385                 390                 395                 400

Leu Pro Glu Lys Leu Arg Cys Glu Pro Val Pro Lys Leu Gln Ser Pro
                405                 410                 415

Cys Lys Lys Arg Val Leu Thr Leu Tyr Glu Ile Ala Gly Pro Asn Gly
                420                 425                 430

Pro Gln Met Val Thr Leu Asn Gly Gln Thr Trp Ser Ala Pro Val Ser
        435                 440                 445

Glu Leu Pro Val Val Gly Ser Thr Glu Glu Trp Asp Ile Val Asn Leu
            450                 455                 460

Thr Met Asp Ala His Pro Ile His Leu His Leu Val Gln Phe Lys Ile
465                 470                 475                 480

Ala Cys Arg Gln Ala Phe Asp Val Asn Ala Tyr Thr Glu Asp Trp Leu
                485                 490                 495

Asp Leu Asn Ser Asp Ile Gly Ser Pro Pro Trp Met Thr Thr Pro Lys
            500                 505                 510

Ala Leu Cys Pro Gly Ser Tyr Thr Ile Gly Asp Asn Gln Pro Pro Ala
            515                 520                 525

Ala Asn Glu Ala Gly Trp Lys Asp Thr Ile Gln Ala Pro Pro Gly Glu
530                 535                 540

Ile Ser Arg Ile Arg Val Arg Phe Ala Pro Gln Asn Val Glu Cys Ser
545                 550                 555                 560

Cys Pro Gly Glu Asn Leu Tyr Pro Phe Asp Pro Ser Lys Gly Pro Asp
                565                 570                 575

Tyr Val Trp His Cys His Ile Leu Asp His Glu Asp Asn Asp Met Met
```

Arg Pro Tyr Arg Val Leu
                595

<210> SEQ ID NO 36
<211> LENGTH: 611
<212> TYPE: PRT
<213> ORGANISM: Clostridium novyi

<400> SEQUENCE: 36

Met Asn Ile Arg Arg Asp Asn Leu Asn Asp Ile Leu Asp Pro Asn Thr
1               5                   10                  15

Ile Pro Lys Tyr Val Glu Gln Leu Pro Ile Pro Lys Val Phe Val Pro
            20                  25                  30

Gln Leu Ile Lys Asp Pro Asn Thr Cys Met Val Lys Gly Glu Tyr Tyr
        35                  40                  45

Tyr Val Thr Ala Lys Glu Phe Ala Gln Gln Leu Leu Pro Arg Cys Phe
    50                  55                  60

Pro Lys Thr Ile Val Trp Gly Tyr Gly Gly Lys Val Lys Asp Trp Phe
65                  70                  75                  80

Thr Gly Glu Ile Tyr His Asp Tyr Arg Ser Tyr Pro Gly Pro Thr Phe
                85                  90                  95

Glu Ala Thr Arg Gly Val Pro Ile Asn Val Gln Trp Val Asn Asn Leu
            100                 105                 110

Thr Gly Tyr Asn Pro Leu Ala Val Asp Pro Thr Leu His Trp Ala Asp
        115                 120                 125

Pro Lys Ile Gly Pro Ile Lys Pro Gln Asp Val Pro Phe Pro Pro
    130                 135                 140

Gly Leu Pro Gln Ala Gln Tyr Pro Ile Pro Leu Val Thr His Leu His
145                 150                 155                 160

Gly Gly Glu Val Cys Ser Thr Phe Asp Gly His Pro Glu Ala Trp Phe
                165                 170                 175

Thr Ser Asn Glu Lys Leu Ile Gly Pro Gln Phe Gly Thr Ser Leu Tyr
            180                 185                 190

Gln Tyr Leu Asn Thr Gln Pro Ser Thr Ala Leu Trp Tyr His Asp His
        195                 200                 205

Thr Leu Gly Leu Thr Arg Leu Asn Val Val Met Gly Leu Ala Gly Phe
    210                 215                 220

Tyr Ile Ile Arg Asp Lys Asn Pro Leu Asp Lys Pro Gly Cys Ile
225                 230                 235                 240

Leu Pro Asp Arg Lys Tyr Glu Ile Pro Leu Val Ile Gln Asp His Thr
                245                 250                 255

Phe Asn Ile Asp Gly Thr Leu Tyr Phe Pro Asn Val Gly Asp Asn Pro
            260                 265                 270

Asp Ile His Pro Tyr Trp Gln Pro Glu Phe Phe Gly Asn Thr Ile Ser
        275                 280                 285

Val Asn Gly Met Thr Trp Pro Asn Leu Asn Val Glu Gln Thr Met Tyr
    290                 295                 300

Arg Phe Arg Met Leu Asn Gly Ala Asn Ala Arg Phe Phe Thr Leu Lys
305                 310                 315                 320

Phe Ser Asn Asn Met Ser Phe Leu Gln Ile Gly Ser Asp Gly Gly Tyr
                325                 330                 335

Phe Glu Gln Pro Val Lys Leu Gly Glu Leu Thr Leu Ala Pro Ala Gln
            340                 345                 350

```
Arg Ala Asp Ile Leu Ile Asp Phe Ser Ser Leu Lys Lys Gly Thr Lys
            355                 360                 365

Ile Ile Leu Asn Asn Ser Ala Asn Ala Pro Phe Ser Ser Ile Lys Ala
    370                 375                 380

Pro Asn Asn Gln Thr Val Gly Gln Val Met Gln Phe Thr Val Lys Gly
385                 390                 395                 400

Cys Tyr Lys Pro Phe Lys Leu Val Leu Pro Lys Lys Leu Asn Asn Ile
                405                 410                 415

Pro Met Leu Val Pro Asn Lys Pro Lys Arg Val Leu Thr Leu Ile Glu
            420                 425                 430

Ile Thr Gly Thr Gly Gly Ile Gln Leu Leu Asp Gly Gln Lys Trp Ser
            435                 440                 445

Ala Pro Ile Thr Glu Leu Pro Leu Val Gly Ser Thr Glu Leu Trp Glu
            450                 455                 460

Leu Val Asn Leu Thr Val Asp Thr His Pro Ile His Leu His Leu Val
465                 470                 475                 480

Gln Phe Gln Leu Gln Asp Arg Gln Lys Phe Asn Ser Asp Lys Tyr Asn
                485                 490                 495

Ser Asp Trp Leu Asn Leu Asn Gly Tyr Leu Pro Leu Asn His Pro Thr
            500                 505                 510

Lys Ala Ile Asp Pro Gly Ile Tyr Leu Gln Gly Asp Pro Ile Pro Pro
            515                 520                 525

Asp Pro Asn Glu Lys Gly Trp Met Asp Thr Val Arg Ala Tyr Pro Gly
            530                 535                 540

Glu Val Thr Arg Ile Leu Val Arg Phe Ala Pro Ile Asp Ala Asp Thr
545                 550                 555                 560

Ser Gln Val Lys Pro Gly Lys Asn Leu Tyr Pro Phe Ala Pro Gln Glu
                565                 570                 575

Gly Pro Gly Tyr Val Trp His Cys His Met Leu Asp His Glu Asp Asn
            580                 585                 590

Glu Met Met Arg Pro Met Ile Val Met Asn Lys Gln Ile Asn Asn Ile
            595                 600                 605

Asn Arg Leu
    610

<210> SEQ ID NO 37
<211> LENGTH: 511
<212> TYPE: PRT
<213> ORGANISM: Bacillus subtilis

<400> SEQUENCE: 37

Met Thr Leu Glu Lys Phe Val Asp Ala Leu Pro Ile Pro Asp Thr Leu
1               5                   10                  15

Lys Pro Val Gln Gln Ser Lys Glu Lys Thr Tyr Tyr Glu Val Thr Met
            20                  25                  30

Glu Glu Cys Thr His Gln Leu His Arg Asp Leu Pro Pro Thr Arg Leu
            35                  40                  45

Trp Gly Tyr Asn Gly Leu Phe Pro Gly Pro Thr Ile Glu Val Lys Arg
    50                  55                  60

Asn Glu Asn Val Tyr Val Lys Trp Met Asn Asn Leu Pro Ser Thr His
65                  70                  75                  80

Phe Leu Pro Ile Asp His Thr Ile His Ser Asp Ser Gln His Glu
                85                  90                  95

Glu Pro Glu Val Lys Thr Val Val His Leu His Gly Gly Val Thr Pro
            100                 105                 110
```

Asp Asp Ser Asp Gly Tyr Pro Glu Ala Trp Phe Ser Lys Asp Phe Glu
        115                 120                 125

Gln Thr Gly Pro Tyr Phe Lys Arg Glu Val Tyr His Tyr Pro Asn Gln
        130                 135                 140

Gln Arg Gly Ala Ile Leu Trp Tyr His Asp His Ala Met Ala Leu Thr
145                 150                 155                 160

Arg Leu Asn Val Tyr Ala Gly Leu Val Gly Ala Tyr Ile Ile His Asp
                165                 170                 175

Pro Lys Glu Lys Arg Leu Lys Leu Pro Ser Asp Glu Tyr Asp Val Pro
            180                 185                 190

Leu Leu Ile Thr Asp Arg Thr Ile Asn Glu Asp Gly Ser Leu Phe Tyr
        195                 200                 205

Pro Ser Ala Pro Glu Asn Pro Ser Pro Ser Leu Pro Asn Pro Ser Ile
210                 215                 220

Val Pro Ala Phe Cys Gly Glu Thr Ile Leu Val Asn Gly Lys Val Trp
225                 230                 235                 240

Pro Tyr Leu Glu Val Glu Pro Arg Lys Tyr Arg Phe Arg Val Ile Asn
                245                 250                 255

Ala Ser Asn Thr Arg Thr Tyr Asn Leu Ser Leu Asp Asn Gly Gly Asp
            260                 265                 270

Phe Ile Gln Ile Gly Ser Asp Gly Gly Leu Leu Pro Arg Ser Val Lys
        275                 280                 285

Leu Asn Ser Phe Ser Leu Ala Pro Ala Glu Arg Tyr Asp Ile Ile Ile
        290                 295                 300

Asp Phe Thr Ala Tyr Glu Gly Glu Ser Ile Ile Leu Ala Asn Ser Ala
305                 310                 315                 320

Gly Cys Gly Gly Asp Val Asn Pro Glu Thr Asp Ala Asn Ile Met Gln
                325                 330                 335

Phe Arg Val Thr Lys Pro Leu Ala Gln Lys Thr Lys Ala Glu Ser Arg
            340                 345                 350

Ser Thr Ser Pro His Thr Leu Arg Tyr Ser Met Lys Asp Thr Asn Ile
        355                 360                 365

Arg Thr Leu Lys Leu Ala Gly Thr Gln Asp Glu Tyr Gly Arg Pro Val
        370                 375                 380

Leu Leu Leu Asn Asn Lys Arg Trp His Asp Pro Val Thr Glu Thr Pro
385                 390                 395                 400

Lys Val Gly Thr Thr Glu Ile Trp Ser Ile Ile Asn Arg His Ala Glu
                405                 410                 415

His Ile Leu Ile His Leu His Leu Val Ser Phe Arg Val Leu Asp Arg
            420                 425                 430

Arg Pro Phe Asp Ile Ala Arg Tyr Gln Glu Ser Gly Glu Leu Ser Tyr
        435                 440                 445

Thr Val Arg Cys Pro Ala Ala Ala Ser Glu Lys Gly Trp Lys Asp Thr
450                 455                 460

Ile Gln Ala His Ala Gly Glu Val Leu Arg Ile Ala Ala Thr Phe Gly
465                 470                 475                 480

Pro Tyr Ser Gly Arg Tyr Val Trp His Cys His Ile Leu Glu His Glu
                485                 490                 495

Asp Tyr Asp Met Met Arg Pro Met Asp Ile Thr Asp Pro His Lys
            500                 505                 510

<210> SEQ ID NO 38
<211> LENGTH: 512

<212> TYPE: PRT
<213> ORGANISM: Bacillus atrophaeus

<400> SEQUENCE: 38

Met Asn Leu Glu Lys Phe Ala Asp Met Leu Pro Ile Pro Glu Val Leu
1               5                   10                  15

Lys Pro His Gln Gln Thr Lys Glu Ser Thr Tyr Tyr Glu Val Thr Met
            20                  25                  30

Lys Glu Phe Tyr Gln Lys Leu His Arg Asp Leu Pro Pro Thr Arg Leu
        35                  40                  45

Trp Gly Tyr Asn Ser Leu Phe Pro Gly Pro Thr Ile Glu Val Asn Arg
    50                  55                  60

Asn Glu Asn Val Gln Ile Lys Trp Met Asn Asp Leu Pro Ser Gln His
65                  70                  75                  80

Phe Leu Pro Ile Asp His Thr Ile His His Ser Glu Gly His His Gln
                85                  90                  95

Glu Pro Glu Val Lys Thr Val Val His Leu His Gly Gly Val Thr Pro
            100                 105                 110

Tyr Asp Ser Asp Gly Tyr Pro Glu Ala Trp Phe Ser Lys Gly Phe Gln
        115                 120                 125

Gln Thr Gly Pro Tyr Phe Ser Arg Glu Ile Tyr His Tyr Pro Asn Gln
    130                 135                 140

Gln Arg Gly Ala Ile Leu Trp Tyr His Asp His Ala Met Ala Leu Thr
145                 150                 155                 160

Arg Leu Asn Val Tyr Ala Gly Leu Ala Gly Val Tyr Ile Ile His Asp
                165                 170                 175

Pro Lys Glu Lys Arg Leu Lys Leu Pro Ala Gly Glu Tyr Asp Val Pro
            180                 185                 190

Leu Met Ile Met Asp Arg Thr Ile Asn Glu Asp Gly Ser Leu Phe Tyr
        195                 200                 205

Pro Ser Gly Pro Glu Asn Pro Ser Pro Thr Leu Pro Thr Pro Ser Ile
    210                 215                 220

Val Pro Ala Phe Cys Gly Asp Thr Ile Leu Val Asn Gly Lys Ala Trp
225                 230                 235                 240

Pro Tyr Met Glu Val Glu Pro Arg Ala Tyr Arg Phe Arg Ile Val Asn
                245                 250                 255

Ala Ser Asn Thr Arg Thr Tyr Asn Leu Ser Leu Asp Asn Gly Gly Glu
            260                 265                 270

Phe Leu Gln Val Gly Ser Asp Gly Gly Leu Leu Pro Arg Ser Val Lys
        275                 280                 285

Leu Ser Ser Ile Ser Leu Ala Pro Ala Glu Arg Phe Asp Ile Ile Ile
    290                 295                 300

Asp Phe Ala Ala Phe Glu Gly Gln Ser Ile Val Leu Ala Asn Ser Glu
305                 310                 315                 320

Gly Cys Gly Gly Asp Ala Asn Pro Glu Ser Asp Ala Asn Val Met Gln
                325                 330                 335

Phe Arg Val Ile Lys Pro Leu Lys Glu Lys Asp Glu Ser Arg Lys Pro
            340                 345                 350

Arg Phe Leu Thr Asn Leu Pro Pro Val Thr Asp Glu Lys Ile Gln Asn
        355                 360                 365

Leu Arg Thr Leu Lys Leu Thr Gly Thr Gln Asp Glu Tyr Gly Arg Pro
    370                 375                 380

Val Leu Leu Leu Asn Asn Lys Arg Trp Ser Asp Pro Val Thr Glu Ala
385                 390                 395                 400

```
Pro Lys Leu Gly Thr Ser Glu Ile Trp Ser Ile Ile Asn Pro Thr Arg
            405                 410                 415

Gly Thr His Pro Ile His Leu His Leu Ile Ser Phe Arg Val Leu Asp
            420                 425                 430

Arg Arg Pro Phe Asp Thr Ala Lys Tyr Ala Glu Thr Asn Val Ser Phe
            435                 440                 445

Thr Gly Pro Ala Val Pro Pro Pro Ser Glu Lys Gly Trp Lys Asp
450                 455                 460

Thr Val Gln Ser His Ala Gly Glu Val Ile Arg Ile Met Ala Lys Phe
465                 470                 475                 480

Gly Pro Tyr Ser Gly Arg Tyr Val Trp His Cys His Ile Leu Glu His
                485                 490                 495

Glu Asp Tyr Asp Met Met Arg Pro Met Asp Val Val Asp Pro Asn Gln
            500                 505                 510

<210> SEQ ID NO 39
<211> LENGTH: 509
<212> TYPE: PRT
<213> ORGANISM: Bacillus pumilus

<400> SEQUENCE: 39

Met Asn Leu Glu Lys Phe Val Asp Glu Leu Pro Ile Pro Glu Val Ala
1               5                   10                  15

Glu Pro Val Lys Lys Asn Pro Arg Gln Thr Tyr Tyr Glu Ile Ala Met
                20                  25                  30

Glu Glu Val Phe Leu Lys Val His Arg Asp Leu Pro Pro Thr Lys Leu
            35                  40                  45

Trp Thr Tyr Asn Gly Ser Leu Pro Gly Pro Thr Ile His Ala Asn Arg
50                  55                  60

Asn Glu Lys Val Lys Val Lys Trp Met Asn Lys Leu Pro Leu Lys His
65              70                  75                  80

Phe Leu Pro Val Asp His Thr Ile His Glu Gly His His Asp Glu Pro
                85                  90                  95

Glu Val Lys Thr Val Val His Leu His Gly Gly Val Thr Pro Ala Ser
            100                 105                 110

Ser Asp Gly Tyr Pro Glu Ala Trp Phe Ser Arg Asp Phe Glu Ala Thr
        115                 120                 125

Gly Pro Phe Phe Glu Arg Glu Val Tyr Glu Tyr Pro Asn His Gln Gln
130                 135                 140

Ala Cys Thr Leu Trp Tyr His Asp His Ala Met Ala Leu Thr Arg Leu
145                 150                 155                 160

Asn Val Tyr Ala Gly Leu Ala Gly Phe Tyr Leu Ile Ser Asp Ala Phe
                165                 170                 175

Glu Lys Ser Leu Glu Leu Pro Ser Asp Asp Tyr Asp Ile Pro Leu Met
            180                 185                 190

Ile Met Asp Arg Thr Phe Gln Glu Asp Gly Ser Leu Phe Tyr Pro Ser
        195                 200                 205

Arg Pro Asn Asp Thr Pro Glu Asp Ser Asp Ile Pro Asp Pro Ser Ile
210                 215                 220

Val Pro Phe Phe Cys Gly Glu Thr Ile Leu Val Asn Gly Lys Val Trp
225                 230                 235                 240

Pro Tyr Leu Glu Val Glu Pro Arg Lys Tyr Arg Phe Arg Ile Leu Asn
                245                 250                 255

Ala Ser Asn Thr Arg Thr Tyr Glu Leu His Leu Asp Asn Asp Ala Thr
```

```
                260                 265                 270
Ile Met Gln Ile Gly Ser Asp Gly Gly Phe Leu Pro Arg Pro Val Arg
            275                 280                 285

His Gln Ser Phe Ser Leu Ala Pro Ala Glu Arg Phe Asp Ile Ile Ile
        290                 295                 300

Asp Phe Ser Ala Tyr Glu Asn Lys Thr Ile Thr Leu Lys Asn Thr Ala
305                 310                 315                 320

Gly Cys Gly Gln Asp Val Asn Pro Glu Thr Asp Ala Asn Ile Met Gln
                325                 330                 335

Phe Lys Val Thr Arg Pro Leu Lys Gly Arg Val Pro Lys Thr Leu Arg
            340                 345                 350

Pro Ile Phe Lys Pro Leu Pro Pro Leu Arg Pro Ser Arg Ala Asp Arg
        355                 360                 365

Glu Arg Thr Leu Thr Leu Thr Gly Thr Gln Asp Lys Tyr Gly Arg Pro
    370                 375                 380

Ile Leu Leu Leu Asp Asn His Phe Trp His Asp Pro Val Thr Glu Pro
385                 390                 395                 400

Arg Leu Gly Ser Leu Glu Val Trp Ser Ile Val Asn Pro Thr Arg Gly
                405                 410                 415

Thr His Pro Ile His Leu His Leu Val Gln Phe Arg Val Ile Asp Arg
            420                 425                 430

Arg Pro Phe Asp Thr Glu Val Tyr Gln Ser Thr Gly Glu Ile Val Tyr
        435                 440                 445

Thr Gly Pro Asn Glu Ala Pro Pro Leu His Glu Gln Gly Tyr Lys Asp
    450                 455                 460

Thr Ile Gln Ala His Ala Gly Glu Val Ile Arg Ile Val Ala Arg Phe
465                 470                 475                 480

Val Pro Tyr Thr Gly Arg Tyr Val Trp His Cys His Ile Leu Glu His
                485                 490                 495

Glu Asp Tyr Asp Met Met Arg Pro Met Asp Ile Ile Gln
            500                 505

<210> SEQ ID NO 40
<211> LENGTH: 504
<212> TYPE: PRT
<213> ORGANISM: Mycobacterium tuberculosis

<400> SEQUENCE: 40

Met Pro Glu Leu Ala Thr Ser Gly Asn Ala Phe Asp Lys Arg Arg Phe
1               5                   10                  15

Ser Arg Arg Gly Phe Leu Gly Ala Gly Ile Ala Ser Gly Phe Ala Leu
            20                  25                  30

Ala Ala Cys Ala Ser Lys Pro Thr Ala Ser Gly Ala Ala Gly Met Thr
        35                  40                  45

Ala Ala Ile Asp Ala Ala Glu Ala Ala Arg Pro His Ser Gly Arg Thr
    50                  55                  60

Val Thr Ala Thr Leu Thr Pro Gln Pro Ala Arg Ile Asp Leu Gly Gly
65                  70                  75                  80

Pro Ile Val Ser Thr Leu Thr Tyr Gly Asn Thr Ile Pro Gly Pro Leu
                85                  90                  95

Ile Arg Ala Thr Val Gly Asp Glu Ile Val Val Ser Val Thr Asn Arg
            100                 105                 110

Leu Gly Asp Pro Thr Ser Val His Trp His Gly Ile Ala Leu Arg Asn
        115                 120                 125
```

Asp Met Asp Gly Thr Glu Pro Ala Thr Ala Asn Ile Gly Pro Gly Gly
130                 135                 140

Asp Phe Thr Tyr Arg Phe Ser Val Pro Asp Pro Gly Thr Tyr Trp Ala
145                 150                 155                 160

His Pro His Val Gly Leu Gln Gly Asp His Gly Leu Tyr Leu Pro Val
                165                 170                 175

Val Val Asp Asp Pro Thr Glu Pro Gly His Tyr Asp Ala Glu Trp Ile
            180                 185                 190

Ile Ile Leu Asp Asp Trp Thr Asp Gly Ile Gly Lys Ser Pro Gln Gln
        195                 200                 205

Leu Tyr Gly Glu Leu Thr Asp Pro Asn Lys Pro Thr Met Gln Asn Thr
210                 215                 220

Thr Gly Met Pro Glu Gly Glu Gly Val Asp Ser Asn Leu Leu Gly Gly
225                 230                 235                 240

Asp Gly Gly Asp Ile Ala Tyr Pro Tyr Tyr Leu Ile Asn Gly Arg Ile
                245                 250                 255

Pro Val Ala Ala Thr Ser Phe Lys Ala Lys Pro Gly Gln Arg Ile Arg
            260                 265                 270

Ile Arg Ile Ile Asn Ser Ala Ala Asp Thr Ala Phe Arg Ile Ala Leu
        275                 280                 285

Ala Gly His Ser Met Thr Val Thr His Thr Asp Gly Tyr Pro Val Ile
290                 295                 300

Pro Thr Glu Val Asp Ala Leu Leu Ile Gly Met Ala Glu Arg Tyr Asp
305                 310                 315                 320

Val Met Val Thr Ala Ala Gly Gly Val Phe Pro Leu Val Ala Leu Ala
                325                 330                 335

Glu Gly Lys Asn Ala Leu Ala Arg Ala Leu Leu Ser Thr Gly Ala Gly
            340                 345                 350

Ser Pro Pro Asp Pro Gln Phe Arg Pro Asp Glu Leu Asn Trp Arg Val
        355                 360                 365

Gly Thr Val Glu Met Phe Thr Ala Ala Thr Ala Asn Leu Gly Arg
370                 375                 380

Pro Glu Pro Thr His Asp Leu Pro Val Thr Leu Gly Gly Thr Met Ala
385                 390                 395                 400

Lys Tyr Asp Trp Thr Ile Asn Gly Glu Pro Tyr Ser Thr Thr Asn Pro
                405                 410                 415

Leu His Val Arg Leu Gly Gln Arg Pro Thr Leu Met Phe Asp Asn Thr
            420                 425                 430

Thr Met Met Tyr His Pro Ile His Leu His Gly His Thr Phe Gln Met
        435                 440                 445

Ile Lys Ala Asp Gly Ser Pro Gly Ala Arg Lys Asp Thr Val Ile Val
450                 455                 460

Leu Pro Lys Gln Lys Met Arg Ala Val Leu Val Ala Asp Asn Pro Gly
465                 470                 475                 480

Val Trp Val Met His Cys His Asn Asn Tyr His Gln Val Ala Gly Met
                485                 490                 495

Ala Thr Arg Leu Asp Tyr Ile Leu
            500

<210> SEQ ID NO 41
<211> LENGTH: 396
<212> TYPE: PRT
<213> ORGANISM: Mycobacterium africanum

<400> SEQUENCE: 41

Met Thr Asn Arg Leu Gly Asp Pro Thr Ser Val His Trp His Gly Ile
1               5                   10                  15

Ala Leu Arg Asn Asp Met Asp Gly Thr Glu Pro Ala Thr Ala Asn Ile
            20                  25                  30

Gly Pro Gly Gly Asp Phe Thr Tyr Arg Phe Ser Val Pro Asp Pro Gly
            35                  40                  45

Thr Tyr Trp Ala His Pro His Val Gly Leu Gln Gly Asp His Gly Leu
50                  55                  60

Tyr Leu Pro Val Val Asp Asp Pro Thr Glu Pro Gly His Tyr Asp
65              70                  75                  80

Ala Glu Trp Ile Ile Ile Leu Asp Trp Thr Asp Gly Ile Gly Lys
                85                  90                  95

Ser Pro Gln Gln Leu Tyr Gly Glu Leu Thr Asp Pro Asn Lys Pro Thr
            100                 105                 110

Met Gln Asn Thr Thr Gly Met Pro Glu Gly Glu Gly Val Asp Ser Asn
            115                 120                 125

Leu Leu Gly Gly Asp Gly Gly Asp Ile Ala Tyr Pro Tyr Tyr Leu Ile
        130                 135                 140

Asn Gly Arg Ile Pro Val Ala Ala Thr Ser Phe Lys Ala Lys Pro Gly
145                 150                 155                 160

Gln Arg Ile Arg Ile Arg Ile Ile Asn Ser Ala Ala Asp Thr Ala Phe
                165                 170                 175

Arg Ile Ala Leu Ala Gly His Ser Met Thr Val Thr His Thr Asp Gly
            180                 185                 190

Tyr Pro Val Ile Pro Thr Glu Val Asp Ala Leu Leu Ile Gly Met Ala
            195                 200                 205

Glu Arg Tyr Asp Val Met Val Thr Ala Ala Gly Gly Val Phe Pro Leu
210                 215                 220

Val Ala Leu Ala Glu Gly Lys Asn Ala Leu Ala Arg Ala Leu Leu Ser
225                 230                 235                 240

Thr Gly Ala Gly Ser Pro Pro Asp Pro Gln Phe Arg Pro Asp Glu Leu
            245                 250                 255

Asn Trp Arg Val Gly Thr Val Glu Met Phe Thr Ala Ala Thr Thr Ala
            260                 265                 270

Asn Leu Gly Arg Pro Glu Pro Thr His Asp Leu Pro Val Thr Leu Gly
            275                 280                 285

Gly Thr Met Ala Lys Tyr Asp Trp Thr Ile Asn Gly Glu Pro Tyr Ser
        290                 295                 300

Thr Thr Asn Pro Leu His Val Arg Leu Gly Gln Arg Pro Thr Leu Met
305                 310                 315                 320

Phe Asp Asn Thr Thr Met Met Tyr His Pro Ile His Leu His Gly His
                325                 330                 335

Thr Phe Gln Met Ile Lys Ala Asp Gly Ser Pro Gly Ala Arg Lys Asp
            340                 345                 350

Thr Val Ile Val Leu Pro Lys Gln Lys Met Arg Ala Val Leu Val Ala
            355                 360                 365

Asp Asn Pro Gly Val Trp Val Met His Cys His Asn Asn Tyr His Gln
370                 375                 380

Val Ala Gly Met Ala Thr Arg Leu Asp Tyr Ile Leu
385                 390                 395

<210> SEQ ID NO 42
<211> LENGTH: 539

<212> TYPE: PRT
<213> ORGANISM: Mycobacterium kansasii

<400> SEQUENCE: 42

```
Met Pro Val Leu Pro Ala Ser Gly His Pro Leu Gly Val Gln Leu
1               5                   10                  15

Ser Arg Arg Gly Phe Ile Gly Ala Gly Ile Ala Ser Gly Leu Ala Leu
                20                  25                  30

Ala Gly Cys Gly His Ser Gln Thr His Ser Ala Glu Ala Ala Met Ala
            35                  40                  45

Ala Ala Ile Asp Ala Ala Glu Arg Ala Arg Pro His Ser Gly Arg Thr
50                  55                  60

Val Thr Ala Ser Leu Val Pro Gln Gln Ala Glu Ile Asp Leu Gly Gly
65                  70                  75                  80

Pro Ile Ala His Thr Leu Ala Tyr Gly Asn Thr Val Pro Gly Pro Leu
                85                  90                  95

Ile Arg Ala Ala Val Gly Asp Glu Ile Val Ala Val Thr Asn Arg
                100                 105                 110

Leu Asp Arg Pro Thr Ser Val His Trp His Gly Ile Ala Leu Arg Asn
                115                 120                 125

Asp Met Asp Gly Val Val Pro Ala Thr Pro Asn Ile Glu Ala Gly His
130                 135                 140

Asp Phe Thr Tyr Arg Phe Ser Val Pro Asp Pro Gly Thr Tyr Trp Ala
145                 150                 155                 160

His Pro His Val Gly Leu Glu Glu Asp Met Gly Leu Tyr Leu Pro Val
                165                 170                 175

Ile Ile Asp Asp Pro Thr Glu Pro Gly Arg Tyr Asp Ala Glu Trp Ile
                180                 185                 190

Val Val Leu Asp Asp Trp Thr Asp Gly Val Gly Lys Ser Pro Gln Gln
                195                 200                 205

Ile Tyr Asp Ala Leu Val Asp Pro Asn Lys Pro Thr Ala Met Pro Thr
210                 215                 220

Thr Thr Pro Pro Ser Thr Thr Pro Pro Thr Thr Thr Asp Thr Thr Ser
225                 230                 235                 240

Thr Thr Ser Ala Thr Ser Thr Thr Thr Thr Glu Thr Thr Pro Ser
                245                 250                 255

Ser Pro Met Pro Gly Met Pro Gly Gly Asp Val Ala Ser Ser Asp Leu
                260                 265                 270

Leu Gly Gly Asp Gly Gly Asp Val Ala Tyr Pro Tyr Tyr Leu Ile Asn
                275                 280                 285

Gly Arg Ile Pro Ala Ala Pro Thr Thr Phe Asn Ala Lys Pro Gly Gln
                290                 295                 300

Arg Ile Arg Ile Arg Ile Ile Asn Ala Ala Ala Asp Thr Ala Phe Arg
305                 310                 315                 320

Val Ala Leu Ala Gly His Ser Met Thr Val Thr His Thr Asp Gly Tyr
                325                 330                 335

Pro Val Leu Pro Thr Pro Val Asp Ala Leu Leu Ile Gly Met Gly Glu
                340                 345                 350

Arg Tyr Asp Val Ile Val Thr Ala Ala Ser Gly Val Phe Pro Leu Val
                355                 360                 365

Ala Leu Ala Glu Gly Lys Asn Ala Val Ala Arg Ser Leu Leu Ser Thr
                370                 375                 380

Gly Ala Gly Ser Ala Pro Asp Pro Gln Phe Arg Pro Ala Glu Leu Thr
385                 390                 395                 400
```

```
Lys Lys Val Gly Thr Ile Glu Met Phe Thr Ala Thr Ser Ala Asn
                405                 410                 415

Leu Gly Arg Ala Glu Pro Gly Leu Glu Leu Pro Val Val Leu Gly Gly
            420                 425                 430

Thr Met Ala Lys Tyr Asp Trp Thr Ile Asn Gly Glu Pro Tyr Ser Arg
            435                 440                 445

Thr Lys Pro Leu Gln Val His Gln Gly Gln Arg Gln Leu Leu Val Phe
        450                 455                 460

Asp Asn Ala Thr Val Met Trp His Pro Met His Leu His Gly His Thr
465                 470                 475                 480

Tyr Gln Ile Ile Lys Ala Asp Gly Ser Leu Gly Ala Arg Lys Asp Thr
                485                 490                 495

Val Ile Val Leu Pro Lys Gln Lys Val Gln Ala Val Leu Val Ala Asp
                500                 505                 510

Asn Pro Gly Thr Trp Val Met His Cys His Asn Met Tyr His Leu Ala
            515                 520                 525

Ala Gly Met Met Thr Arg Leu Asp Tyr Val Phe
        530                 535

<210> SEQ ID NO 43
<211> LENGTH: 477
<212> TYPE: PRT
<213> ORGANISM: Staphylococcus aureus

<400> SEQUENCE: 43

Met Tyr Asn Lys Val Phe Ala Ile Leu Ile Ile Phe Ser Ile Ile
1               5                   10                  15

Ile Ile Ala Ser Asn Asp Thr Phe Ala Glu Ser Lys Asn Asp Met Met
                20                  25                  30

Asn Met Lys Glu Asp Lys Lys Ser Thr Met Asp Met Thr Asn Met Lys
            35                  40                  45

His His Asp Glu Arg Lys Lys Leu Asn Ser Ser Gln Gly Lys Asn Glu
        50                  55                  60

Ile Ile Phe Pro Glu Val Ala Glu Ser Lys Lys Asp Asn Asn Gly Tyr
65                  70                  75                  80

Lys Asn Tyr Thr Leu Lys Ala Gln Lys Gly Lys Thr Glu Phe Tyr Lys
                85                  90                  95

Asn Asn Phe Ser Asn Thr Leu Gly Tyr Asn Gly Asn Leu Leu Gly Pro
            100                 105                 110

Thr Leu Lys Leu Lys Lys Gly Asp Lys Val Lys Ile Lys Leu Ile Asn
        115                 120                 125

Asn Leu Asp Glu Asn Thr Thr Phe His Trp His Gly Leu Glu Val Asn
130                 135                 140

Gly Lys Val Asp Gly Gly Pro Ser Gln Val Ile Lys Pro Gly Lys Glu
145                 150                 155                 160

Lys Thr Ile Lys Phe Glu Val Asn Gln Asp Ser Ala Thr Leu Trp Tyr
                165                 170                 175

His Pro His Pro Ser Pro Asn Thr Ala Lys Gln Val Tyr Asn Gly Leu
            180                 185                 190

Ser Gly Leu Leu Tyr Ile Glu Asp Ser Lys Asn Asn Tyr Pro Ser
        195                 200                 205

Asn Tyr Gly Lys Asn Asp Leu Pro Ile Ile Gln Asp Lys Thr Phe
        210                 215                 220

Val Ser Lys Lys Leu Asn Tyr Ser Lys Thr Lys Asp Glu Asp Gly Thr
```

```
            225                 230                 235                 240
        Gln Gly Asp Thr Val Leu Val Asn Gly Ile Val Asn Pro Lys Leu Thr
                        245                 250                 255

Ala Lys Glu Glu Lys Ile Arg Leu Arg Leu Leu Asn Gly Ser Asn Ala
                        260                 265                 270

Arg Asp Leu Asn Leu Lys Leu Ser Asn Asn Gln Ser Phe Glu Tyr Ile
                        275                 280                 285

Ala Ser Asp Gly Gly Gln Leu Lys Asn Ala Lys Lys Leu Lys Glu Ile
                        290                 295                 300

Asn Leu Ala Pro Ser Glu Arg Lys Glu Ile Val Ile Asp Leu Ser Lys
        305                 310                 315                 320

Met Lys Gly Glu Lys Ile Ser Leu Val Asp Asn Asp Lys Thr Val Ile
                        325                 330                 335

Leu Pro Ile Ser Asn Lys Glu Lys Ser Ser Asn Lys Ser Asn Thr Pro
                        340                 345                 350

Lys Val Gly Lys Lys Ile Lys Leu Glu Gly Met Asn Asp Asn Val Thr
                        355                 360                 365

Ile Asn Gly Asn Lys Phe Asp Pro Asn Arg Ile Asp Phe Thr Gln Lys
                        370                 375                 380

Leu Asn Gln Lys Glu Val Trp Glu Ile Glu Asn Val Lys Asp Lys Met
        385                 390                 395                 400

Gly Gly Met Lys His Pro Phe His Ile His Gly Thr Gln Phe Lys Val
                        405                 410                 415

Leu Ser Val Asp Gly Glu Lys Pro Pro Lys Asp Met Arg Gly Lys Lys
                        420                 425                 430

Asp Val Ile Ser Leu Glu Pro Gly Gln Lys Ala Lys Ile Glu Val Val
                        435                 440                 445

Phe Lys Asn Thr Gly Thr Tyr Met Phe His Cys His Ile Leu Glu His
                        450                 455                 460

Glu Asp Asn Gly Met Met Gly Gln Val Lys Val Thr Asn
        465                 470                 475

<210> SEQ ID NO 44
<211> LENGTH: 477
<212> TYPE: PRT
<213> ORGANISM: Staphylococcus epidermidis

<400> SEQUENCE: 44

Met Tyr Asn Lys Val Phe Ala Ile Leu Ile Ile Phe Ser Ile Ile
        1               5                   10                  15

Ile Ile Ala Ser Asn Asp Thr Phe Ala Glu Ser Lys Asn Asp Met Met
                        20                  25                  30

Asn Met Lys Glu Asp Lys Lys Asn Thr Met Asp Met Lys Asn Met Lys
                        35                  40                  45

His His Asp Glu Arg Lys Lys Leu Asn Ser Ser Gln Gly Lys Asn Glu
                        50                  55                  60

Ile Ile Phe Pro Glu Val Ala Glu Ser Lys Lys Asp Asn Asn Gly Tyr
        65                  70                  75                  80

Lys Asn Tyr Thr Leu Lys Ala Gln Glu Gly Lys Thr Glu Phe Tyr Lys
                        85                  90                  95

Asn Asn Phe Ser Asn Thr Leu Gly Tyr Asn Gly Asn Leu Leu Gly Pro
                        100                 105                 110

Thr Leu Lys Leu Lys Lys Gly Asp Lys Val Lys Ile Lys Leu Ile Asn
                        115                 120                 125
```

```
Asn Leu Asp Glu Asn Thr Thr Phe His Trp His Gly Leu Glu Ile Asn
    130                 135                 140

Gly Lys Val Asp Gly Gly Pro Ser Gln Val Ile Lys Pro Gly Lys Glu
145                 150                 155                 160

Lys Thr Ile Lys Phe Glu Val Asn Gln Asp Ser Ala Thr Leu Trp Tyr
                165                 170                 175

His Pro His Pro Ser Pro Asn Thr Ala Lys Gln Val Tyr Asn Gly Leu
            180                 185                 190

Ser Gly Leu Leu Tyr Ile Glu Asp Ser Lys Lys Asn Asn Tyr Pro Ser
        195                 200                 205

Asn Tyr Gly Lys Asn Asp Leu Pro Ile Ile Gln Asp Lys Thr Phe
    210                 215                 220

Val Ser Lys Lys Leu Asn Tyr Ser Lys Thr Lys Asp Glu Asp Gly Thr
225                 230                 235                 240

Gln Gly Asp Thr Val Leu Val Asn Gly Ile Val Asn Pro Lys Leu Thr
                245                 250                 255

Ala Lys Glu Glu Lys Ile Arg Leu Arg Leu Leu Asn Gly Ser Asn Ala
            260                 265                 270

Arg Asp Leu Asn Leu Lys Leu Ser Asn Asn Gln Ser Phe Glu Tyr Ile
        275                 280                 285

Ala Ser Asp Gly Gly Gln Leu Lys Asn Ala Lys Lys Leu Lys Glu Ile
    290                 295                 300

Asn Leu Ala Pro Ser Glu Arg Lys Glu Ile Val Ile Asp Leu Ser Lys
305                 310                 315                 320

Met Lys Gly Glu Lys Ile Ser Leu Val Asp Asn Asp Lys Thr Val Ile
                325                 330                 335

Leu Pro Ile Ser Asn Lys Glu Lys Ser Ser Asn Lys Gly Asn Thr Pro
            340                 345                 350

Lys Val Ser Lys Lys Ile Lys Leu Glu Gly Met Asn Asp His Val Thr
        355                 360                 365

Ile Asn Gly Asn Lys Phe Asp Pro Asn Arg Ile Asp Phe Thr Gln Lys
    370                 375                 380

Leu Asn Gln Lys Glu Val Trp Glu Ile Glu Asn Val Lys Asp Lys Met
385                 390                 395                 400

Gly Gly Met Lys His Pro Phe His Ile His Gly Thr Gln Phe Lys Val
                405                 410                 415

Leu Ser Val Asp Gly Glu Lys Pro Pro Lys Asp Met Arg Gly Lys Lys
            420                 425                 430

Asp Val Ile Ser Leu Glu Pro Gly Gln Lys Ala Lys Ile Glu Ile Val
        435                 440                 445

Phe Lys Asn Thr Gly Thr Tyr Met Phe His Cys His Ile Leu Glu His
    450                 455                 460

Glu Glu Asn Gly Met Met Gly Gln Val Lys Ile Thr Asn
465                 470                 475

<210> SEQ ID NO 45
<211> LENGTH: 477
<212> TYPE: PRT
<213> ORGANISM: Staphylococcus saprophyticus

<400> SEQUENCE: 45

Met Tyr Lys Lys Met Phe Thr Ile Leu Ile Thr Leu Phe Ser Ile Met
1               5                   10                  15

Phe Met Val Pro Asn Asp Thr Phe Ala Glu Gly Lys His Asn Met Met
            20                  25                  30
```

-continued

```
Asp Met Lys Glu Asn Asp Gln Lys Arg Asn Asp Met Met Asp Met Lys
        35                  40                  45
Ser His Asp Glu Arg Lys Asn Leu Asn Ser Ser Gln Gly Lys Asn Glu
    50                  55                  60
Ile Thr Phe Pro Lys Val Leu Asp Pro Lys Lys Asp Asn Asn Gly Tyr
65                  70                  75                  80
Lys Ser Tyr Thr Leu Lys Ala Gln Lys Gly Lys Thr Glu Phe Tyr Lys
                85                  90                  95
Gly Asn Phe Ser Asn Thr Leu Gly Tyr Asn Gly Asn Leu Leu Gly Pro
            100                 105                 110
Thr Leu Lys Leu Lys Lys Gly Asp Lys Val Lys Ile Lys Leu Val Asn
        115                 120                 125
Asn Leu Asp Glu Asn Thr Thr Phe His Trp His Gly Leu Glu Ile Asp
    130                 135                 140
Gly Lys Val Asp Gly Gly Pro Ser Gln Val Ile Lys Pro Gly Lys Glu
145                 150                 155                 160
Lys Thr Ile Lys Phe Glu Val Lys Gln Glu Ala Ala Thr Leu Trp Tyr
                165                 170                 175
His Pro His Pro Ser Pro Asn Thr Ala Lys Gln Val Tyr Asn Gly Leu
            180                 185                 190
Ser Gly Leu Leu Tyr Ile Glu Asp Asp Lys Lys Asn Asn Tyr Pro Ser
        195                 200                 205
Asn Tyr Gly Lys Asn Asp Leu Pro Ile Ile Ile Gln Asp Lys Thr Phe
    210                 215                 220
Val Ser Lys Lys Leu Asn Tyr Thr Lys Thr Lys Asp Glu Asp Gly Thr
225                 230                 235                 240
Gln Gly Asp Thr Val Leu Val Asn Gly Lys Val Asp Pro Lys Leu Thr
                245                 250                 255
Thr Lys Glu Gly Lys Ile Arg Leu Arg Leu Leu Asn Gly Ser Asn Ala
            260                 265                 270
Arg Asp Leu Asn Leu Lys Leu Ser Asn Asn Gln Ser Phe Glu Tyr Ile
        275                 280                 285
Ala Ser Glu Gly Gly His Leu Glu Lys Thr Lys Lys Leu Lys Glu Ile
    290                 295                 300
Asn Leu Ala Pro Ser Ala Arg Lys Glu Ile Val Ile Asp Leu Ser Lys
305                 310                 315                 320
Met Lys Glu Glu Lys Val Asn Leu Val Asp Asn Asp Glu Thr Val Ile
                325                 330                 335
Leu Pro Ile Ile Asn Lys Glu Lys Ser Thr Asn Lys Asp Thr Thr Pro
            340                 345                 350
Lys Val Asp Lys Lys Ile Lys Leu Glu Gly Met Asn Asp Asp Val Thr
        355                 360                 365
Ile Asn Gly Lys Lys Phe Asp Pro Asn Arg Ile Asp Phe Thr Gln Lys
    370                 375                 380
Val Asn Arg Lys Glu Thr Trp Glu Ile Glu Asn Val Lys Asp Lys Met
385                 390                 395                 400
Gly Gly Met Lys His Pro Phe His Ile His Gly Thr Gln Phe Lys Val
                405                 410                 415
Leu Ser Val Asp Gly Lys Lys Pro Glu Ser Asp Met Arg Gly Lys Lys
            420                 425                 430
Asp Val Ile Ser Leu Glu Pro Gly Gln Lys Ala Lys Ile Glu Val Val
        435                 440                 445
```

Phe Lys Asn Thr Gly Thr Tyr Met Phe His Cys His Ile Leu Glu His
450                 455                 460

Glu Asp Asn Gly Met Met Gly Gln Ile Lys Val Thr Lys
465                 470                 475

<210> SEQ ID NO 46
<211> LENGTH: 463
<212> TYPE: PRT
<213> ORGANISM: Pseudomonas aeruginosa

<400> SEQUENCE: 46

Met Thr Phe Thr Arg Arg Gln Val Leu Gly Gly Leu Ala Gly Leu Ala
1               5                   10                  15

Val Val Gly Leu Gly Ala Gly Gly Ala Arg Leu Trp Leu Ala Arg Pro
                20                  25                  30

Gln Val Ala Gln Glu Tyr Asp Tyr Glu Leu Ile Ala Ala Pro Leu Asp
            35                  40                  45

Leu Glu Ile Val Pro Gly Phe Ser Ser Pro Ala Leu Ala Tyr Gly Gly
        50                  55                  60

Gln Cys Pro Gly Val Glu Leu Arg Ala Lys Gln Gly Glu Trp Leu Arg
65                  70                  75                  80

Val Arg Phe Thr Asn Arg Leu Asp Glu Pro Thr Thr Ile His Trp His
                85                  90                  95

Gly Ile Arg Leu Pro Ile Glu Met Asp Gly Val Pro Tyr Ile Ser Gln
            100                 105                 110

Pro Pro Val Gln Pro Gly Glu Ser Phe Ile Tyr Gln Phe Lys Thr Gln
        115                 120                 125

Asp Ala Gly Ser Tyr Trp Tyr His Pro His Leu Met Ser Ser Glu Gln
    130                 135                 140

Leu Gly Arg Gly Leu Val Gly Pro Leu Ile Ile Glu Glu Arg Glu Pro
145                 150                 155                 160

Thr Gly Phe Arg His Glu Lys Val Leu Cys Leu Lys Thr Trp His Val
                165                 170                 175

Asp Glu Gln Gly Ala Phe Thr Pro Phe Ser Val Pro Arg Gln Ala Ala
            180                 185                 190

Arg Glu Gly Thr Arg Gly Arg Tyr Ser Thr Ile Asn Gly Lys His Val
        195                 200                 205

Pro Thr Ile Asp Leu Pro Ala Gly Gln Ile Val Arg Val Arg Leu Leu
    210                 215                 220

Asn Val Asp Asn Thr Val Thr Tyr Arg Leu Asn Leu Pro Asn Gly Glu
225                 230                 235                 240

Ala Arg Ile Tyr Ala Val Asp Gly His Pro Val Glu Pro Arg Gly Phe
                245                 250                 255

Glu Gly Gln Tyr Trp Ile Gly Pro Gly Met Arg Leu Glu Leu Ala Leu
            260                 265                 270

Lys Val Pro Glu Ala Gly Thr Glu Leu Ser Leu Arg Asp Gly Pro Val
        275                 280                 285

Arg Leu Ala Thr Ile Arg Ser Val Ala Ser Ala Glu Ala Pro Ala Gly
    290                 295                 300

Asp Trp Pro Lys Pro Leu Pro Ala Asn Pro Val Ser Gly Pro Asp Leu
305                 310                 315                 320

Ala Asn Ala Glu Lys Ile Gly Phe Arg Phe Glu Trp Val Gly Ala Met
                325                 330                 335

Ser Asp Thr Ser Gly Lys Asn Pro Tyr Pro Ser Phe Trp Gln Ile Asn
            340                 345                 350

```
Gly Lys Ala Trp Glu Gly Glu Glu His Lys His Asn Ala Pro Pro
            355                 360                 365

Leu Ala Lys Leu Lys Glu Gly Gln Ser Tyr Ile Phe Glu Leu Arg Asn
    370                 375                 380

Met Ala Gln Tyr Gln His Pro Ile His Leu His Gly Met Ala Phe Lys
385                 390                 395                 400

Val Leu Asp Ser Asp Arg Arg Glu Ile Ile Pro Tyr Phe Thr Asp Thr
                405                 410                 415

Tyr Leu Leu Gly Lys Asn Glu Thr Ala Arg Val Ala Leu Val Ala Asp
                420                 425                 430

Asn Pro Gly Leu Trp Met Phe His Cys His Val Ile Asp His Met Glu
            435                 440                 445

Thr Gly Leu Met Gly Thr Ile Ala Val Gly Glu Ala Trp Cys Gly
            450                 455                 460

<210> SEQ ID NO 47
<211> LENGTH: 458
<212> TYPE: PRT
<213> ORGANISM: Pseudomonas fluorescens

<400> SEQUENCE: 47

Met Ser Phe Thr Arg Arg Gln Ile Leu Gly Gly Leu Ala Gly Leu Val
1               5                   10                  15

Val Val Gly Val Gly Ala Gly Ala Ser Arg Tyr Trp Leu Gly Lys
                20                  25                  30

Met Ala Asp Ala Asp Ala Gly Tyr Asp Tyr Glu Leu Ile Ala Ala Pro
            35                  40                  45

Leu Asp Val Glu Leu Val Pro Gly His Lys Thr Glu Ala Trp Ala Phe
    50                  55                  60

Gly Pro Ser Ala Pro Gly Thr Glu Leu Arg Val Arg Gln Gly Glu Trp
65                  70                  75                  80

Leu Arg Val Arg Phe Ile Asn His Leu Pro Val Ala Thr Thr Ile His
                85                  90                  95

Trp His Gly Ile Arg Leu Pro Leu Glu Met Asp Gly Val Pro Tyr Val
                100                 105                 110

Ser Gln Leu Pro Val Leu Pro Gly Glu Tyr Phe Asp Tyr Lys Phe Arg
            115                 120                 125

Val Pro Asp Ala Gly Ser Tyr Trp Tyr His Pro His Val Ser Ser Ser
    130                 135                 140

Glu Glu Leu Gly Arg Gly Leu Val Gly Pro Leu Ile Val Glu Glu Arg
145                 150                 155                 160

Glu Pro Thr Gly Phe Lys Tyr Glu Lys Thr Leu Ser Leu Lys Asn Trp
                165                 170                 175

His Ile Asp Asp Glu Gly His Phe Val Glu Phe Ser Val Pro Arg Glu
                180                 185                 190

Ala Ala Arg Gly Gly Thr Ala Gly Arg Leu Ser Thr Ile Asn Gly Val
            195                 200                 205

Pro Ser Pro Val Ile Glu Leu Pro Ala Gly Gln Ile Thr Arg Val Arg
    210                 215                 220

Leu Leu Asn Leu Asp Asn Thr Leu Thr Tyr Arg Leu Asn Ile Pro Gly
225                 230                 235                 240

Val Glu Ala Gln Ile Tyr Ala Leu Asp Gly Asn Pro Val Glu Pro Arg
                245                 250                 255

Pro Leu Gly Lys Glu Tyr Trp Leu Gly Pro Gly Met Arg Ile Cys Leu
```

```
                    260                 265                 270
Ala Ile Lys Ala Pro Ala Gly Glu Glu Leu Ser Leu Arg Asn Gly
            275                 280                 285

Pro Val Arg Leu Gly Thr Leu Arg Ser Val Ala Asn Asn Asp Ala Pro
        290                 295                 300

Thr Glu Trp Pro Lys Ala Leu Pro Ala Asn Pro Val Ala Glu Pro Asp
305                 310                 315                 320

Leu Ala Asn Ala Glu Lys Leu Asn Phe Asn Phe Glu Trp Val Gly Ser
                325                 330                 335

Val Ser Val Asn Val Asp Asn Gly Lys Pro Pro Ser Leu Trp Gln Ile
            340                 345                 350

Asn Gly Lys Ala Trp Val Ile Thr Asp Lys Thr Cys Ala Asp Arg Pro
        355                 360                 365

Ile Ala Ser Leu Lys Leu Gly Gln Ser Tyr Ile Phe Glu Leu Lys Asn
    370                 375                 380

Met Thr Gln Tyr Gln His Pro Ile His Leu His Gly Met Ser Phe Lys
385                 390                 395                 400

Val Ile Ala Ser Asn Arg His Lys Ile Ile Pro Tyr Phe Thr Asp Thr
                405                 410                 415

Tyr Leu Leu Gly Lys Asn Glu Arg Ala Gln Val Ala Leu Val Ala Asp
            420                 425                 430

Asn Pro Gly Val Trp Met Phe His Cys His Val Ile Asp His Met Glu
        435                 440                 445

Thr Gly Leu Met Ala Ala Ile Glu Val Lys
    450                 455

<210> SEQ ID NO 48
<211> LENGTH: 459
<212> TYPE: PRT
<213> ORGANISM: Pseudomonas putida

<400> SEQUENCE: 48

Met Ser Phe Thr Arg Arg Gln Met Leu Lys Gly Leu Thr Gly Leu Val
1               5                   10                  15

Val Val Gly Leu Gly Ala Gly Ala Ala Arg Tyr Trp Leu Gly Lys
            20                  25                  30

Val Glu Asp Glu Asn Ala Gly His Asp Tyr Glu Leu Ile Ala Ala Pro
        35                  40                  45

Leu Glu Val Glu Leu Val Pro Gly Phe Lys Thr Glu Ala Trp Ala Phe
    50                  55                  60

Gly Pro Ser Ala Pro Gly Thr Glu Leu Arg Val Arg Gln Gly Thr Trp
65                  70                  75                  80

Leu Arg Val Arg Phe Ile Asn His Leu Pro Val Glu Thr Thr Ile His
                85                  90                  95

Trp His Gly Ile Arg Leu Pro Leu Glu Met Asp Gly Val Pro Tyr Val
            100                 105                 110

Ser Gln Leu Pro Val Lys Pro Gly Glu Tyr Phe Asp Tyr Lys Phe Arg
        115                 120                 125

Val Pro Asp Ala Gly Ser Tyr Trp Tyr His Pro His Val Ser Ser Ser
    130                 135                 140

Glu Glu Leu Gly Arg Gly Leu Val Gly Pro Leu Ile Val Glu Glu Arg
145                 150                 155                 160

Glu Pro Thr Gly Phe Gln His Glu Arg Thr Leu Ser Leu Lys Asn Trp
                165                 170                 175
```

-continued

```
His Val Asp Glu Gln Gly Ala Trp Leu Pro Phe Ser Ile Pro Arg Glu
            180                 185                 190

Ala Ala Arg Asn Gly Thr Ala Gly Arg Leu Ile Thr Ile Asn Gly Gln
        195                 200                 205

Ala Asp Ser Ile Thr Glu Leu Pro Ala Gly Gln Val Val Arg Val Arg
    210                 215                 220

Val Leu Asn Leu Asp Asn Thr Trp Thr Tyr Arg Leu Asn Leu Lys Gly
225                 230                 235                 240

Asn Cys Glu Ala Arg Ile Tyr Ala Leu Asp Gly Asn Pro Val Thr Pro
                245                 250                 255

Arg Ala Leu Asp Glu Tyr Trp Leu Gly Pro Gly Met Arg Ile Cys Leu
            260                 265                 270

Ala Ile Arg Ile Pro Glu Ala Gly Glu Glu Ile Ser Leu Arg Asp Gly
        275                 280                 285

Phe Val Arg Leu Gly Thr Leu Arg Ser Val Ala Ser Asn Asp Ala Pro
    290                 295                 300

Ser Asp Trp Pro Pro Ala Leu Pro Pro Asn Pro Ile Ala Glu Pro Asp
305                 310                 315                 320

Leu Glu His Ala Glu Lys Leu Asn Phe Asn Phe Glu Trp Ala Ala Gly
                325                 330                 335

Val Ser Val Thr Ala Asp Pro Ala Lys Pro Ser Ser Met Trp Gln Ile
            340                 345                 350

Asn Gly Gln Ala Trp Asp Ile Thr Asp Lys Thr Cys Ala Asp Arg Pro
        355                 360                 365

Ile Ala Thr Leu Gln Lys Gly Lys Ser Tyr Ile Phe Glu Leu Lys Asn
    370                 375                 380

Met Thr Gln Tyr Gln His Pro Ile His Leu His Gly Met Ser Phe Lys
385                 390                 395                 400

Val Ile Ala Ser Asn Arg His Asp Ile Lys Glu Pro Trp Phe Thr Asp
                405                 410                 415

Thr Tyr Leu Leu Gly Lys Asn Glu Arg Ala Gln Val Ala Leu Val Ala
            420                 425                 430

Asp Asn Pro Gly Thr Trp Met Phe His Cys His Val Ile Asp His Met
        435                 440                 445

Glu Thr Gly Leu Met Ala Ala Ile Ala Val Val
    450                 455

<210> SEQ ID NO 49
<211> LENGTH: 678
<212> TYPE: PRT
<213> ORGANISM: Trichophyton rubrum

<400> SEQUENCE: 49

Met Asp Arg Pro Ala Ser Arg Arg His Asn Ser Gln Arg Arg Leu
1               5                   10                  15

Gln Gln Gln Pro Glu Asp Glu Ser Val Val Ala Ala Asp Thr Leu Ile
            20                  25                  30

Ile Pro Val Gln Arg Glu Asp Glu Lys Arg Pro Ala Gly Pro Ser Thr
        35                  40                  45

Gly Ser Gln Thr Gly Glu Thr Lys Pro Glu Asp His Arg Arg Ser Leu
    50                  55                  60

Ser Gly Cys Pro Trp Leu Leu Val Gly Phe Val Cys Cys Ile Ser Thr
65                  70                  75                  80

Leu Leu Leu Val Leu Gly Leu Ala Ala Arg Trp Gln Gln Gly Ala Ile
                85                  90                  95
```

```
Pro Asn Ile Phe Asp Ile Gly Asn Leu Arg Pro Ser Ser Ser Pro Ala
            100                 105                 110

Ser Ser Ser Ser Ser Thr Ala Gly Pro Trp Ser Ser Arg Leu His Pro
        115                 120                 125

Glu Asp His Leu Phe Arg Pro Glu Thr Thr Ile Thr Leu Glu Trp Ser
    130                 135                 140

Val Thr Thr Gly Tyr Arg Arg Leu Asp Gly Val Lys Lys Arg Val Tyr
145                 150                 155                 160

Leu Ile Asn Gly Leu Phe Pro Gly Pro Thr Ile Glu Ala Arg Ser Gly
                165                 170                 175

Asp Ser Leu Gln Val Gln Val Thr Asn Asn Ile Gln Asp Glu Gly Leu
            180                 185                 190

Val Ile His Trp His Gly Leu His Met Arg Gly Ala Asn His Met Asp
        195                 200                 205

Gly Val Thr Gly Val Thr Gln Cys Pro Ile Val Pro Gly Asp Ser Met
    210                 215                 220

Leu Tyr Asn Phe Thr Ile Ser Gln Ser Gln Ser Gly Thr Phe Trp Tyr
225                 230                 235                 240

His Ala His Ser Ala Leu Gln Arg Ala Glu Gly Leu Tyr Gly Gly Phe
                245                 250                 255

Val Val His Lys Pro Ser Thr Pro Ser Met Arg Ile Ala Arg Asp Pro
            260                 265                 270

Ala Ile His Ala Asp Ala Val Lys Tyr Gln Tyr Glu Lys Glu His Leu
        275                 280                 285

Leu Leu Ile Gly Asp Trp Tyr His Arg Pro Ala Glu Asp Val Leu Lys
    290                 295                 300

Trp Phe Lys Ser Leu Glu Ala Asn Gly Gln Glu Pro Val Pro Asp Ser
305                 310                 315                 320

Phe Leu Ile Asn Gly Ala Gly Arg Phe Asn Cys Ser Met Ala Leu Pro
                325                 330                 335

Thr Arg Pro Ile Asp Cys Val Asp Glu Gly Tyr Pro Thr Pro Glu Leu
            340                 345                 350

Leu Leu Asp Ser Ser Thr Ser Tyr Arg Met Arg Val Ile Asn Val Gly
        355                 360                 365

Ser Leu Ala Gly Val Ser Leu Gly Phe Glu His Gly Thr Val Thr Pro
    370                 375                 380

Ile Gln Val Asp Gly Gly Thr Glu Val Glu Leu Pro Ser Val Ser Pro
385                 390                 395                 400

Asn Ala Arg Ser Met Gly Ile Val Tyr Pro Gly Gln Arg Thr Asp Phe
                405                 410                 415

Val Leu Arg Asn Pro Leu Gly Glu Thr Gly Gln Ser Ser Ile Thr Val
            420                 425                 430

Glu Leu Asp Pro Glu Cys Phe Ser Leu Pro Asn Pro Ala Leu Thr Arg
        435                 440                 445

Val Gln Thr Phe Pro Ile Ser Gly Ser Ala Lys Lys Pro Ser His Pro
    450                 455                 460

Leu Ser Asp Asn Pro Ile Gly Glu Ala Gly Thr His Val Asp Leu Thr
465                 470                 475                 480

Glu Leu Thr Ser Thr Ala Ser Thr Ile Ser His Ile Pro Ala Lys Ala
                485                 490                 495

Asp Glu Thr Phe Leu Val Tyr Thr Leu Leu Ser Lys Leu Ser Ser Asn
            500                 505                 510
```

-continued

```
Asn Tyr Val Pro Phe Ala Phe Phe Asn His Thr Ser Trp Arg Pro Gln
        515                 520                 525

Ala Asp Pro Pro Leu Pro Leu Ile Ser Leu Gln Arg Lys Asp Trp Asp
    530                 535                 540

Lys Asn Gln Phe Thr Ile Lys Thr Ser Ser Arg Ala Ser Trp Val Asp
545                 550                 555                 560

Leu Ile Val Asn Asn Leu Asp Glu Gly Pro His Pro Phe His Ile His
                565                 570                 575

Gly His Asp Phe Tyr Val Met Ser Leu His Glu Ala Asp Thr Gly Met
            580                 585                 590

Gly Ser Tyr Asn Pro Trp Asp Pro Ser Asn Lys Ala Pro Ala Tyr Asp
        595                 600                 605

His Ser Gln Ala Ile Leu Arg Asp Thr Val His Ile Pro Ala Arg Gly
    610                 615                 620

His Ala Val Leu Arg Phe Arg Ala Asp Asn Pro Gly Ile Trp Leu Phe
625                 630                 635                 640

His Cys His Ile Leu Trp His Leu Ala Ser Gly Met Ala Met Leu Val
                645                 650                 655

Asp Val Met Asp Ser Ala Ser Arg Pro Leu His Gly Ile Leu Asn Gln
            660                 665                 670

Thr Cys Arg Tyr Leu Thr
        675

<210> SEQ ID NO 50
<211> LENGTH: 681
<212> TYPE: PRT
<213> ORGANISM: Trichophyton tonsurans

<400> SEQUENCE: 50

Met Asp Arg Pro Ala Ser Arg Arg His Asn Ser Gln Arg Arg Leu
1               5                   10                  15

Gln Gln Pro Gly Asp Glu Ser Ala Val Ala Ala Asp Thr Leu Ile Pro
            20                  25                  30

Val Gln Arg Glu Gly Glu Lys Arg Pro Ala Arg Pro Ser Ala Gly Ser
        35                  40                  45

Gln Thr Gly Glu Thr Lys Pro Gly Asp Gln Arg Arg Ser Leu Pro Gly
    50                  55                  60

Arg Pro Trp Pro Trp Pro Leu Val Gly Phe Val Cys Cys Ile Ser Thr
65                  70                  75                  80

Leu Leu Ile Val Leu Gly Leu Ala Ala Arg Trp Gln Gln Gly Ala Ile
                85                  90                  95

Pro Asn Ile Phe Asp Ile Gly Ile Leu Arg Pro Ser Ser Ser Pro Ala
            100                 105                 110

Ser Ser Ser Pro Ser Thr Ala Glu Pro Trp Ser Ser Arg Leu His Pro
        115                 120                 125

Glu Asp His Val Phe Arg Pro Glu Thr Thr Val Thr Leu Glu Trp Ser
    130                 135                 140

Val Ser Thr Gly Tyr Arg Arg Leu Asp Gly Val Lys Lys Arg Val Tyr
145                 150                 155                 160

Leu Ile Asn Gly Leu Phe Pro Gly Pro Thr Ile Glu Ala Arg Ser Gly
                165                 170                 175

Asp Ser Leu Arg Ile Lys Val Thr Asn Asn Ile Gln Asp Glu Gly Leu
            180                 185                 190

Val Ile His Trp His Gly Leu His Met Arg Gly Ala Asn His Met Asp
        195                 200                 205
```

-continued

Gly Val Thr Gly Val Thr Gln Cys Pro Ile Val Pro Gly Asp Ser Met
            210                 215                 220

Leu Tyr Asn Phe Thr Ile Ser Gln Ser Gln Ser Gly Thr Phe Trp Tyr
225                 230                 235                 240

His Ala His Ser Ala Leu Gln Arg Ala Glu Gly Leu Tyr Gly Gly Phe
                245                 250                 255

Val Val His Lys Pro Ser Thr Pro Ser Met Arg Ile Ala Arg Asp Pro
            260                 265                 270

Ala Met His Ala Asp Ala Val Lys Tyr Gln Tyr Glu Arg Glu His Leu
            275                 280                 285

Leu Leu Ile Gly Asp Trp Tyr His Arg Pro Ala Asp Asp Val Leu Asn
290                 295                 300

Trp Phe Lys Ser Leu Glu Ala Asn Gly Gln Glu Pro Val Pro Asp Ser
305                 310                 315                 320

Phe Leu Ile Asn Gly Ala Gly Arg Phe Asn Cys Ser Met Ala Leu Pro
                325                 330                 335

Thr Arg Pro Leu Asp Cys Val Asp Glu Gly Tyr Pro Thr Pro Glu Leu
            340                 345                 350

Leu Leu Asp Ser Ser Ser Ser Ser Tyr Arg Met Arg Val Val Asn
            355                 360                 365

Val Gly Ser Leu Ala Gly Val Ser Leu Ala Phe Glu His Gly Thr Val
370                 375                 380

Thr Pro Ile Gln Val Asp Gly Gly Thr Glu Val Glu Leu Pro Ser Val
385                 390                 395                 400

Ser Pro Asn Ala Arg Ser Ile Gly Ile Val Tyr Pro Gly Gln Arg Thr
                405                 410                 415

Asp Phe Val Leu Arg Asn Ala Phe Gly Gly Ala Glu Gln Ser Ser Ile
            420                 425                 430

Thr Val Glu Leu Asp Pro Glu Cys Phe Ser Leu Pro Asn Pro Ala Leu
            435                 440                 445

Thr Arg Val Gln Thr Phe Pro Ile Arg Gly Ser Ala Lys Lys Pro Ser
            450                 455                 460

Ser His Thr Leu Ser Asp Asn Pro Ile Gly Glu Ser Gly Thr His Val
465                 470                 475                 480

Asp Leu Thr Glu Leu Thr Ser Thr Ala Ser Thr Ile Ser His Ile Pro
                485                 490                 495

Ala Glu Ala Asp Glu Thr Phe Leu Val Tyr Thr Leu Leu Ser Lys Leu
                500                 505                 510

Ser Ser Asn Asn Tyr Val Pro Phe Ala Phe Asn His Thr Ser Trp
            515                 520                 525

Arg Pro Gln Ala Asp Pro Pro Leu Pro Leu Ile Ser Leu Gln Arg Lys
            530                 535                 540

Asp Trp Asp Lys Asn Gln Phe Thr Ile Lys Thr Ser Ser Lys Ala Ser
545                 550                 555                 560

Trp Val Asp Leu Val Val Asn Asn Leu Asp Glu Gly Pro His Pro Phe
                565                 570                 575

His Ile His Gly His Asp Phe Tyr Val Met Ser Leu His Glu Ala Asp
            580                 585                 590

Thr Gly Met Gly Ser Tyr Asn Pro Trp Asp Pro Ser Asn Gln Ala Pro
            595                 600                 605

Ala Tyr Asn His Ser Lys Ala Ile Leu Arg Asp Thr Val His Ile Pro
610                 615                 620

```
Ala Arg Gly His Ala Val Leu Arg Phe Arg Ala Asp Asn Pro Gly Ile
625                 630                 635                 640

Trp Leu Phe His Cys His Ile Leu Trp His Leu Ala Ser Gly Met Ala
                645                 650                 655

Met Leu Val Asp Val Met Asp Ser Val Ser Arg Pro Leu His Gly Ile
            660                 665                 670

Pro Asn Gln Thr Cys Arg Tyr Leu Thr
        675                 680

<210> SEQ ID NO 51
<211> LENGTH: 626
<212> TYPE: PRT
<213> ORGANISM: Candida albicans

<400> SEQUENCE: 51

Met Arg Phe Ile Val Ser Ser Phe Ile Phe Ile Ser Phe Leu Ser
1               5                   10                  15

Ser Leu Ile Thr Ala Glu Thr His Thr Trp Tyr Phe Lys Thr Ser Trp
                20                  25                  30

Val Asp Ala Asn Pro Asp Gly Val Phe Pro Arg Lys Met Ile Gly Phe
            35                  40                  45

Asn Asp Ser Trp Pro Leu Pro Thr Leu Arg Val Lys Lys Gly Asp Thr
50                  55                  60

Val Asn Leu Tyr Leu Ile Asn Gly Phe Asp Asp Arg Asn Thr Ser Leu
65                  70                  75                  80

His Phe His Gly Leu Phe Gln His Gly Thr Asn Gln Met Asp Gly Pro
                85                  90                  95

Glu Met Val Thr Gln Cys Pro Ile Pro Pro Gly Glu Thr Phe Leu Tyr
            100                 105                 110

Asn Phe Thr Val Asp Asp Gln Val Gly Ser Tyr Trp Tyr His Ser His
                115                 120                 125

Thr Ser Gly Gln Tyr Gly Asp Gly Met Arg Gly Val Phe Ile Ile Glu
            130                 135                 140

Asp Asp Asp Phe Pro Tyr Asp Tyr Asp Glu Glu Val Val Leu Thr Leu
145                 150                 155                 160

Ser Glu His Tyr His Asp Tyr Ser Lys Asp Leu Met Pro Gly Phe Leu
                165                 170                 175

Ser Arg Phe Asn Pro Thr Gly Ala Glu Pro Ile Pro Ser Asn Ile Leu
            180                 185                 190

Phe Asn Glu Thr Arg Asn Asn Thr Trp Lys Val Glu Pro Gly Lys Thr
            195                 200                 205

Tyr Leu Leu Arg Ile Ala Asn Thr Gly Arg Phe Val Thr Gln Tyr Leu
210                 215                 220

Trp Met Glu Asp His Glu Phe Thr Val Val Glu Val Asp Gly Val Tyr
225                 230                 235                 240

Val Glu Lys Asn Thr Thr Asp Met Leu Tyr Ile Thr Ile Ala Gln Arg
            245                 250                 255

Tyr Gly Val Leu Ile Thr Thr Lys Asn Ser Thr Asn Lys Asn Tyr Ala
            260                 265                 270

Phe Met Asn Arg Val Asp Asp Thr Met Leu Asp Thr Ile Pro Lys Asp
            275                 280                 285

Leu Gln Leu Asn Gly Thr Asn Tyr Ile Val Tyr Asn Glu Ser Ala Pro
            290                 295                 300

Leu Pro Asp Ala Tyr Asp Val Asp Ser Ile Asp Asp Tyr Leu Asp Asp
305                 310                 315                 320
```

```
Phe Tyr Leu Lys Pro Leu Asn Lys Glu Lys Leu Leu Asp Ala Asp
                325                 330                 335

Tyr Thr Ile Thr Val Asp Val Gln Met Asp Asn Leu Gly Asn Gly Val
            340                 345                 350

Asn Tyr Ala Phe Phe Asn Asn Ile Thr Tyr Met Thr Pro Lys Val Pro
        355                 360                 365

Thr Leu Leu Ser Val Leu Ser Ala Gly Asp Ala Ser Thr Asn Glu Leu
    370                 375                 380

Val Tyr Gly Ser Asn Thr Asn Ser Phe Val Leu Gln Gly Gly Asp Val
385                 390                 395                 400

Val Asp Ile Val Leu Asn Asn Leu Asp Thr Gly Arg His Pro Phe His
            405                 410                 415

Leu His Gly His Val Phe Gln Leu Ile Glu Arg His Lys Glu Ile Pro
        420                 425                 430

Asp Thr Glu Asp Pro Val Ser Tyr Asn Val Ser Asp His Ala Glu Trp
    435                 440                 445

Pro Glu Tyr Pro Met Ser Arg Asp Thr Val Tyr Val Lys Pro Gln Ser
450                 455                 460

Tyr Ile Val Met Arg Phe Lys Ala Asp Asn Pro Gly Val Trp Phe Phe
465                 470                 475                 480

His Cys His Ile Glu Trp His Leu Asp Gln Gly Leu Ala Ile Val Leu
            485                 490                 495

Ile Glu Asp Pro Glu Ala Ile Gln Lys Asn Ser Ser Gln His Leu Thr
        500                 505                 510

Asp Asn His Lys Gln Ile Cys Glu Lys Val Gly Val Ser Trp Glu Gly
    515                 520                 525

Asn Ala Ala Asn Ser Asn Asn Tyr Leu Asp Leu Lys Gly Glu Asn
530                 535                 540

Ile Gln Val Lys Arg Leu Pro Thr Gly Phe Thr Ala Arg Gly Ile Val
545                 550                 555                 560

Ala Leu Val Phe Ser Cys Ile Ala Ala Phe Leu Gly Ile Ala Ala Ile
            565                 570                 575

Ala Tyr Tyr Gly Met Asn Asp Ile Glu Asp Val Glu Glu Arg Val Ala
        580                 585                 590

Arg Asp Leu Asp Val Asp Leu Asp Glu Glu Asn Glu Asp Glu Glu Glu
    595                 600                 605

Ala Glu Ile Val Asn Glu Gly Ser Ser Ser Gly Ser Asn Ser Lys
610                 615                 620

Gln His
625

<210> SEQ ID NO 52
<211> LENGTH: 623
<212> TYPE: PRT
<213> ORGANISM: Candida dubliniensis

<400> SEQUENCE: 52

Met Arg Met Thr Leu Ser Ser Leu Val Ile Ser Ile Thr Phe Phe Phe
1               5                   10                  15

Ser Leu Ile Ala Ala Glu Thr His Thr Trp Tyr Phe Lys Thr Gly Trp
            20                  25                  30

Val Asn Ala Asn Pro Asp Gly Val Phe Glu Arg Pro Met Ile Gly Phe
        35                  40                  45

Asn Asp Ser Trp Pro Leu Pro Thr Leu Arg Val Lys Lys Gly Asp Arg
```

-continued

```
             50                  55                  60
Ile Gln Leu Tyr Leu Ile Asn Gly Phe Asp Asn Leu Asn Thr Thr Leu
 65                  70                  75                  80

His Phe His Gly Leu Phe Gln Asn Gly Thr Asn Gln Met Asp Gly Pro
                     85                  90                  95

Glu Met Val Thr Gln Cys Pro Ile Pro Pro Gly Glu Thr Tyr Leu Tyr
                    100                 105                 110

Asn Phe Thr Val Asp Gln Val Gly Thr Tyr Trp Tyr His Ser His Thr
                115                 120                 125

Ala Gly Gln Tyr Gly Asp Gly Met Arg Gly Val Phe Val Ile Glu Asp
                130                 135                 140

Asp Asp Phe Pro Tyr Asp Tyr Asp Glu Asp Val Val Leu Thr Leu Gly
145                 150                 155                 160

Asp His Tyr His Asp Tyr Ser Asn Glu Ile Ile Pro Thr Phe Leu Ser
                    165                 170                 175

Arg Phe Asn Pro Thr Gly Ala Glu Pro Ile Pro Gln Asn Phe Leu Phe
                180                 185                 190

Asn Glu Thr Arg Asn Leu Thr Trp Lys Val Glu Pro Gly Lys Thr Tyr
                195                 200                 205

Leu Val Arg Ile Val Asn Ile Gly Gly Phe Val Ser Gln Tyr Leu Trp
210                 215                 220

Met Glu Asp His Gln Phe Thr Val Val Glu Val Asp Gly Ile Tyr Val
225                 230                 235                 240

Glu Lys Asn Thr Thr Asp Ile Leu Tyr Ile Thr Thr Ala Gln Arg Tyr
                    245                 250                 255

Ser Val Leu Ile Thr Thr Lys Asn Ser Thr Asp Lys Asn Tyr Ala Phe
                260                 265                 270

Met Gln Arg Val Asp Thr Asp Met Leu Asp Val Ile Pro Ser Asp Leu
                275                 280                 285

Gln Leu Asn Gly Thr Asn Tyr Ile Val Tyr Asn Glu Asp Ala Ser Leu
                290                 295                 300

Pro Asp Ala Tyr Asp Val Asp Ser Leu Asp Asp Tyr Leu Asp Asp Phe
305                 310                 315                 320

Tyr Leu Lys Pro Leu Ser Lys Glu Lys Leu Leu Asp Asp Ala Asp Tyr
                    325                 330                 335

Thr Ile Thr Val Asp Val Gln Met Asp Asn Leu Asn Asp Gly Val Asn
                340                 345                 350

Tyr Ala Phe Phe Asn Asn Ile Thr Tyr Lys Ala Pro Lys Val Pro Thr
                355                 360                 365

Leu Leu Thr Val Leu Ser Ala Gly Asp Ala Thr Asn Glu Leu Ile
370                 375                 380

Tyr Gly Thr Asn Thr Asn Ser Phe Val Leu Gln Gly Gly Asp Val Val
385                 390                 395                 400

Asp Ile Val Leu Asn Asn Leu Asp Thr Gly Lys His Pro Phe His Leu
                    405                 410                 415

His Gly His Ala Phe Gln Leu Ile Glu Arg His Glu Glu Ile Pro Asp
                420                 425                 430

Thr Glu Asp Pro Val Thr Tyr Asn Ala Thr Asp His Ala Asp Trp Pro
                435                 440                 445

Glu Tyr Pro Met Met Arg Asp Thr Val Tyr Val Arg Pro Gln Ser Tyr
                450                 455                 460

Ile Val Met Arg Phe Lys Ala Asp Asn Pro Gly Val Trp Phe Phe His
465                 470                 475                 480
```

-continued

```
Cys His Ile Glu Trp His Leu Glu Gln Gly Leu Ala Phe Gln Leu Ile
            485                 490                 495

Glu Asp Pro Glu Gly Ile Gln Lys Gln Glu Ser Gln Gln Ile Thr Asp
            500                 505                 510

Asn His Lys Glu Ile Cys Glu Lys Val Gly Val Pro Trp Glu Gly Asn
            515                 520                 525

Ala Ala Gly Asn Thr Glu Asn Tyr Leu Asp Leu Lys Gly Glu Asn Val
            530                 535                 540

Gln His Lys Arg Leu Pro Thr Gly Phe Thr Ala Lys Gly Ile Val Ala
545                 550                 555                 560

Leu Val Phe Ser Cys Ile Ala Gly Phe Leu Gly Met Ala Ala Ile Ser
                565                 570                 575

Tyr Tyr Gly Met Asn Asp Ile Gln Asn Met Glu Lys Arg Ile Ala Arg
            580                 585                 590

Asp Leu Asp Val Tyr Phe Asp Asp Glu Glu Glu Asp Gln Ser Ile
            595                 600                 605

Thr Glu Gln Asp Ala Thr Gly Ser Ser Ser Ser Pro Ser Asn Lys
            610                 615                 620

<210> SEQ ID NO 53
<211> LENGTH: 616
<212> TYPE: PRT
<213> ORGANISM: Candida tropicalis

<400> SEQUENCE: 53

Met Arg Ser Ala Ser Leu Phe Leu Leu Ile Cys Ser Leu Ile Ser Val
1               5                   10                  15

Ile Ser Ala Glu Thr His Thr Trp Trp Phe Gln Thr Gly Trp Val Asn
            20                  25                  30

Ala Asn Pro Asp Gly Val Phe Glu Arg Pro Met Ile Gly Phe Asn Asp
            35                  40                  45

Thr Trp Pro Leu Pro Thr Leu Arg Val Lys Lys Gly Asp Arg Val Gln
        50                  55                  60

Leu Tyr Leu Asn Asn Gly Phe Asp Asp Arg Asn Thr Ser Leu His Phe
65                  70                  75                  80

His Gly Met Phe Gln Asn Gly Thr Asn Gln Met Asp Gly Pro Glu Met
                85                  90                  95

Val Thr Gln Cys Pro Ile Pro Pro Gly Glu Thr Phe Leu Tyr Asn Phe
            100                 105                 110

Thr Val Gly Asp Gln Val Gly Ser Tyr Trp Tyr His Ser His Thr Ser
            115                 120                 125

Gly Gln Tyr Gly Asp Gly Met Arg Gly Val Phe Ile Ile Glu Asp Asp
        130                 135                 140

Asp Phe Pro Tyr Asp Tyr Asp Glu Glu Val Val Leu Thr Leu Ala Glu
145                 150                 155                 160

His Tyr His Asp Phe Ser Asp Glu Leu Thr Pro Lys Phe Leu Ser Arg
                165                 170                 175

Phe Asn Pro Thr Gly Ala Glu Pro Ile Pro Ser Asn Met Leu Phe Asn
            180                 185                 190

Glu Thr Arg Asn Asn Thr Trp Lys Val Glu Pro Asn Lys Thr Tyr Leu
            195                 200                 205

Val Arg Ile Val Asn Ile Gly Arg Phe Val Ser Gln Tyr Ile Trp Met
        210                 215                 220

Glu Asp His Asp Phe Thr Ile Val Glu Val Asp Gly Val Tyr Val Glu
```

```
             225                 230                 235                 240
Gln Asn Thr Thr Asp Leu Leu Tyr Ile Thr Val Ala Gln Arg Tyr Ser
             245                 250                 255
Val Leu Ile Thr Thr Lys Asn Glu Thr Asp Lys Asn Tyr Ala Phe Met
             260                 265                 270
Asn Arg Val Asp Ile Thr Met Leu Asp Val Ile Pro Gly Asp Leu Glu
             275                 280                 285
Leu Asn Gly Thr Asn Tyr Ile Val Tyr Asn Glu Asp Ala Asp Leu Pro
             290                 295                 300
Glu Pro Tyr Leu Leu Asp Ser Ile Asp Asp Phe Phe Asp Asp Phe Trp
305                 310                 315                 320
Leu Lys Pro Leu Ser Lys Glu Lys Leu Leu Asp Asp Ala Asp Tyr Thr
             325                 330                 335
Ile Thr Leu Glu Val Gln Met Asp Asn Leu Gly Asn Gly Val Asn Tyr
             340                 345                 350
Ala Phe Phe Asn Asn Ile Thr Tyr Ala His Pro Lys Val Pro Thr Leu
             355                 360                 365
Met Ser Val Leu Ser Ser Gly Asp Asp Ala Ser Asn Glu Leu Val Tyr
             370                 375                 380
Gly Thr Asn Thr Asn Ser Phe Val Leu Gln Gly Gly Glu Val Val Asp
385                 390                 395                 400
Ile Val Leu Asn Asn Leu Asp Thr Gly Lys His Pro Phe His Leu His
             405                 410                 415
Gly His Ala Phe Gln Leu Ile Glu Arg His Glu Glu Ile Pro Asp Thr
             420                 425                 430
Glu Asp Pro Val Thr Tyr Asn Ala Thr Asp His Ala Asp Trp Pro Glu
             435                 440                 445
Tyr Pro Met Leu Arg Asp Thr Ile Tyr Ile Asn Pro Gln Ser Tyr Ala
             450                 455                 460
Val Leu Arg Phe Lys Ala Asp Asn Pro Gly Val Trp Phe Phe His Cys
465                 470                 475                 480
His Ile Glu Trp His Leu Asp Gln Gly Leu Ala Ile Val Leu Ile Glu
             485                 490                 495
Asp Pro Gln Ala Ile Gln Lys Asn Glu Lys Ile Thr Asp Asn His Lys
             500                 505                 510
Gln Ile Cys Glu Lys Val Gly Val Pro Trp Gln Gly Asn Ala Ala Ala
             515                 520                 525
Asn Asn Lys Asp Tyr Leu Asn Leu Asp Gly Glu Asn Leu Gln Val Lys
             530                 535                 540
Arg Leu Pro Thr Gly Phe Thr Ala Lys Gly Ile Val Ala Leu Val Phe
545                 550                 555                 560
Ser Cys Ile Ala Gly Val Leu Gly Leu Val Ala Ile Ser Tyr Tyr Gly
             565                 570                 575
Met Thr Asp Ile Lys Asn Val Glu Gln Arg Val Ala Arg Asp Leu Asp
             580                 585                 590
Val Asp Leu Asp Asp Asp Val Glu Gln Leu Ser Glu Glu Gly Ser
             595                 600                 605
Ser Gly Ser Asn Ser Lys Gln His
             610                 615

<210> SEQ ID NO 54
<211> LENGTH: 617
<212> TYPE: PRT
<213> ORGANISM: Unknown
```

<220> FEATURE:
<223> OTHER INFORMATION: Candida auris

<400> SEQUENCE: 54

```
Met Asn Gln Leu Ser Leu Phe Phe Val Leu Phe Ile Ser Trp Phe Ala
1               5                   10                  15

Leu Ala Ser Ala Glu Thr His Thr Trp Tyr Phe Lys Thr Gly Trp Val
            20                  25                  30

Lys Ala Asn Pro Asp Gly Asn Phe Glu Arg Asp Val Ile Gly Phe Asn
        35                  40                  45

Gly Ser Trp Pro Leu Pro Thr Leu Arg Val Lys Lys Gly Asp Arg Val
    50                  55                  60

Asn Leu Tyr Leu Thr Asn Gly Phe Asp Asp Arg Asn Thr Thr Leu His
65                  70                  75                  80

Phe His Gly Met Phe Gln Asn Gly Ser Ala Gln Met Asp Gly Pro Glu
                85                  90                  95

Met Val Thr Gln Cys Pro Ile Pro Pro Gly Glu Thr Tyr Leu Tyr Asn
            100                 105                 110

Phe Thr Val Ala Asp Gln Val Gly Thr Tyr Trp Tyr His Ser His Thr
        115                 120                 125

Ala Gly Gln Tyr Gly Asp Gly Met Arg Ala Pro Phe Ile Ile Glu Glu
    130                 135                 140

Lys Asn Lys Glu Asp Tyr Pro Phe Asp Phe Asp Glu Glu Leu Val Leu
145                 150                 155                 160

Pro Leu Gly Glu Trp Tyr His Asp Pro Ala Asp Val Leu Leu Pro Lys
                165                 170                 175

Phe Leu Asn Arg Tyr Asn Pro Thr Gly Ala Glu Pro Ile Pro Gln Asn
            180                 185                 190

Leu Leu Phe Asn Glu Thr Arg Asn Asn Thr Trp Lys Val Glu Pro Asn
        195                 200                 205

Thr Thr Tyr Gly Val Arg Ile Val Asn Met Gly Gly Phe Val Ser Gln
    210                 215                 220

Tyr Leu Tyr Met Glu Asp His Glu Phe Glu Ile Val Glu Val Asp Gly
225                 230                 235                 240

Val Tyr Val Glu Lys Asn Thr Thr Asp Leu Leu Tyr Val Thr Ile Ala
                245                 250                 255

Gln Arg Tyr Gly Val Leu Ile Lys Thr Lys Glu Lys Ala Asp Arg Asn
            260                 265                 270

Tyr Ala Phe Met Asn Ala Phe Asp Asp Thr Met Leu Asp Val Ile Pro
        275                 280                 285

Lys Asp Leu Ile Leu Asn Gly Thr Asn Ser Ile Gln Tyr Thr Asp Asp
    290                 295                 300

Thr Ser Met Pro Asp Glu Tyr Phe Ile Asp Ser Phe Asp Arg Phe
305                 310                 315                 320

Asp Asp Phe Tyr Leu Val Pro Lys Asp Gly Glu Lys Leu Leu Pro Asp
                325                 330                 335

Ser Asp Asn Gln Val Val Ile Asp Val Lys Met Asp Asn Leu Gly Asp
            340                 345                 350

Val Asn Tyr Ala Phe Phe Asn Asn Ile Ser Tyr Val Ala Pro Lys Ile
        355                 360                 365

Pro Leu Leu Ala Thr Ala Met Ser Ala Gly Glu Leu Ala Thr Asn Ser
    370                 375                 380

Tyr Ile Tyr Gly Asn Thr Asn Ala Phe Val Leu Lys Lys Gly Glu Thr
385                 390                 395                 400
```

```
Val Asp Ile Val Leu Asn Asn Gln Asp Gly Thr His Pro Phe His
                405                 410                 415

Leu His Gly His Val Phe Gln Leu Ile Glu Arg Gly Pro Glu Phe Gly
            420                 425                 430

Asp Pro Val Ser Phe Asp Tyr Asn Asn His Ser Glu Phe Pro Glu Tyr
            435                 440                 445

Pro Met Lys Arg Asp Thr Val Tyr Val Asn Pro Asn Ser Tyr Ile Val
        450                 455                 460

Met Arg Phe Thr Ala Asp Asn Pro Gly Val Trp Phe Phe His Cys His
465                 470                 475                 480

Ile Glu Trp His Leu Glu Gln Gly Leu Ala Ile Val Leu Val Glu Ala
                485                 490                 495

Pro Glu Glu Met Gln Lys Asp Pro Ser Gln Gln Leu Thr Glu Asn Phe
            500                 505                 510

Lys Asp Val Cys Ser Lys Gly Gly Met Asn Tyr Ser Gly Asn Ala Ala
            515                 520                 525

Gly Asn Ser Val Asp Phe Met Asp Leu Lys Gly Met Asn Thr Gln Pro
            530                 535                 540

Lys Arg Leu Pro Ala Gly Phe Thr Ala Arg Gly Ile Val Ala Leu Val
545                 550                 555                 560

Phe Ser Cys Ile Ala Gly Val Leu Gly Met Val Ala Ile Thr Ile Tyr
                565                 570                 575

Gly Leu Ala Asp Val Lys Asp Ile Asp Glu Arg Val Ala Arg Asp Leu
            580                 585                 590

Asp Val Asp Leu Asp Glu Ile Ala Ala Asp Glu Ser Ser Gln Leu Val
            595                 600                 605

Pro Gly Asp Ser Ser Ser Arg Asn Lys
            610                 615

<210> SEQ ID NO 55
<211> LENGTH: 296
<212> TYPE: PRT
<213> ORGANISM: Triticum aestivum

<400> SEQUENCE: 55

Met Lys Thr Phe Leu Ile Leu Ala Leu Leu Ala Ile Val Ala Thr Thr
1               5                   10                  15

Ala Thr Thr Ala Val Arg Val Pro Val Pro Gln Pro Gln Pro Gln Asn
            20                  25                  30

Pro Ser Gln Pro Gln Pro Gln Arg Gln Val Pro Leu Val Gln Gln Gln
        35                  40                  45

Gln Phe Pro Gly Gln Gln Gln Phe Pro Pro Gln Gln Pro Tyr Pro
    50                  55                  60

Gln Pro Gln Pro Phe Pro Ser Gln Gln Pro Tyr Leu Gln Leu Gln Pro
65                  70                  75                  80

Phe Pro Gln Pro Gln Pro Phe Pro Pro Gln Leu Pro Tyr Pro Gln Pro
                85                  90                  95

Pro Pro Phe Ser Pro Gln Gln Pro Tyr Pro Gln Pro Gln Pro Gln Tyr
            100                 105                 110

Pro Gln Pro Gln Pro Ile Ser Gln Gln Ala Gln Gln Gln
            115                 120                 125

Gln Gln Gln Gln Gln Gln Gln Gln Gln Gln Gln Gln Ile Leu
        130                 135                 140

Pro Gln Ile Leu Gln Gln Gln Leu Ile Pro Cys Arg Asp Val Val Leu
```

```
                145                 150                 155                 160
        Gln Gln His Asn Ile Ala His Ala Arg Ser Gln Val Leu Gln Ser
                        165                 170                 175
        Thr Tyr Gln Pro Leu Gln Gln Leu Cys Cys Gln Gln Leu Trp Gln Ile
                        180                 185                 190
        Pro Glu Gln Ser Arg Cys Gln Ala Ile His Asn Val His Ala Ile
                    195                 200                 205
        Ile Leu His Gln Gln Gln Gln Gln Gln Pro Ser Ser Gln Val Ser
                210                 215                 220
        Leu Gln Gln Pro Gln Gln Tyr Pro Ser Gly Gln Gly Phe Phe Gln
        225                 230                 235                 240
        Pro Ser Gln Gln Asn Pro Gln Ala Gly Ser Val Gln Pro Gln Gln
                        245                 250                 255
        Leu Pro Gln Phe Glu Glu Ile Arg Asn Leu Ala Leu Gln Thr Leu Pro
                        260                 265                 270
        Arg Met Cys Asn Val Tyr Ile Pro Pro Tyr Cys Ser Thr Thr Ala
                    275                 280                 285
        Pro Phe Gly Ile Phe Gly Thr Asn
            290                 295

<210> SEQ ID NO 56
<211> LENGTH: 296
<212> TYPE: PRT
<213> ORGANISM: Unknown
<220> FEATURE:
<223> OTHER INFORMATION: Triticum sphaerococcum

<400> SEQUENCE: 56

Met Lys Thr Phe Leu Ile Leu Ala Leu Leu Ala Ile Val Ala Thr Thr
        1               5                   10                  15
        Ala Thr Thr Ala Val Arg Val Pro Val Pro Gln Pro Gln Pro Gln Asn
                        20                  25                  30
        Pro Ser Gln Pro Gln Pro Gln Gly Gln Val Pro Leu Val Gln Gln Gln
                    35                  40                  45
        Gln Phe Pro Gly Gln Gln Gln Phe Pro Pro Gln Gln Pro Tyr Pro
        50                  55                  60
        Gln Pro Gln Pro Phe Pro Ser Gln Gln Pro Tyr Leu Gln Leu Gln Pro
        65                  70                  75                  80
        Phe Pro Gln Pro Gln Pro Phe Pro Pro Gln Leu Pro Tyr Pro Gln Pro
                        85                  90                  95
        Pro Pro Phe Ser Pro Gln Gln Pro Tyr Pro Gln Pro Gln Pro Gln Tyr
                        100                 105                 110
        Pro Gln Pro Gln Gln Pro Ile Ser Gln Gln Gln Ala Gln Gln Gln Gln
                    115                 120                 125
        Gln Gln Gln Gln Gln Gln Gln Gln Gln Gln Gln Gln Gln Gln Ile Gln
                130                 135                 140
        Pro Gln Ile Leu Gln Gln Leu Ile Pro Cys Arg Asp Val Val Leu
        145                 150                 155                 160
        Gln Gln His Asn Ile Ala His Ala Arg Ser Gln Val Leu Gln Ser
                        165                 170                 175
        Thr Tyr Gln Pro Leu Gln Gln Leu Cys Cys Gln Gln Leu Trp Gln Ile
                        180                 185                 190
        Pro Glu Gln Ser Arg Cys Gln Ala Ile His Asn Val His Ala Ile
                    195                 200                 205
        Ile Leu His Gln Gln Gln Arg Gln Gln Gln Pro Ser Ser Gln Val Ser
```

```
                210                 215                 220
Leu Gln Gln Pro Gln Gln Gln Tyr Pro Ser Gly Gln Gly Phe Phe Gln
225                 230                 235                 240

Pro Ser Gln Gln Asn Pro Gln Ala Gln Gly Ser Val Gln Pro Gln Gln
                245                 250                 255

Leu Pro Gln Phe Glu Glu Ile Arg Asn Leu Ala Leu Gln Thr Leu Pro
            260                 265                 270

Arg Met Cys Asn Val Tyr Ile Pro Pro Tyr Cys Ser Thr Thr Thr Ala
            275                 280                 285

Pro Phe Gly Ile Phe Gly Thr Asn
            290                 295

<210> SEQ ID NO 57
<211> LENGTH: 288
<212> TYPE: PRT
<213> ORGANISM: Triticum turgidum

<400> SEQUENCE: 57

Met Lys Thr Phe Leu Ile Leu Ala Leu Leu Ala Ile Val Ala Thr Thr
1               5                   10                  15

Ala Thr Thr Ala Val Arg Val Pro Val Pro Gln Pro Gln Pro Gln Asn
            20                  25                  30

Pro Ser Gln Pro Gln Pro Gln Gly Gln Val Pro Leu Val Gln Gln Gln
        35                  40                  45

Gln Phe Pro Gly Gln Gln Gln Phe Pro Pro Gln Gln Pro Tyr Pro
    50                  55                  60

Gln Pro Gln Pro Phe Pro Ser Gln Gln Pro Tyr Leu Gln Leu Gln Pro
65                  70                  75                  80

Phe Pro Gln Pro Gln Pro Phe Pro Pro Gln Leu Pro Tyr Pro Gln Pro
                85                  90                  95

Pro Pro Phe Ser Pro Gln Gln Pro Tyr Pro Gln Pro Gln Pro Gln Tyr
            100                 105                 110

Pro Gln Pro Gln Gln Pro Ile Ser Gln Gln Ala Gln Gln Gln Gln
            115                 120                 125

Gln Gln Gln Gln Gln Gln Ile Gln Pro Gln Ile Leu Gln Gln Gln Leu
    130                 135                 140

Ile Pro Cys Arg Asp Val Val Leu Gln Gln His Asn Ile Ala His Ala
145                 150                 155                 160

Arg Ser Gln Val Leu Gln Gln Ser Thr Tyr Gln Pro Leu Gln Gln Leu
                165                 170                 175

Cys Cys Gln Gln Leu Trp Gln Ile Pro Glu Gln Ser Arg Cys Gln Ala
            180                 185                 190

Ile His Asn Val Val His Ala Ile Ile Leu His Gln Gln Gln Arg Gln
            195                 200                 205

Gln Arg Pro Ser Ser Gln Val Ser Phe Gln Gln Pro Gln Gln Gln Tyr
    210                 215                 220

Pro Ser Gly Gln Gly Phe Phe Gln Pro Ser Gln Gln Asn Pro Gln Ala
225                 230                 235                 240

Gln Gly Ser Val Gln Pro Gln Gln Leu Pro Gln Phe Glu Glu Ile Arg
                245                 250                 255

Asn Leu Ala Leu Gln Thr Leu Pro Arg Met Cys Asn Val Tyr Ile Pro
            260                 265                 270

Pro Tyr Cys Ser Thr Thr Val Pro Phe Gly Ile Phe Ser Thr Asn
            275                 280                 285
```

<210> SEQ ID NO 58
<211> LENGTH: 300
<212> TYPE: PRT
<213> ORGANISM: Triticum dicoccum

<400> SEQUENCE: 58

Met Lys Thr Phe Leu Ile Leu Ala Leu Leu Ala Ile Val Ala Thr Thr
1               5                   10                  15

Ala Thr Thr Ala Val Arg Val Pro Val Pro Gln Leu Gln Pro Gln Asn
            20                  25                  30

Pro Ser Gln Gln Gln Pro Gln Glu Gln Val Pro Leu Val Gln Gln Gln
        35                  40                  45

Gln Phe Pro Gly Gln Gln Gln Phe Pro Pro Gln Gln Pro Tyr Pro
    50                  55                  60

Gln Pro Gln Pro Phe Pro Ser Gln Pro Tyr Leu Gln Leu Gln Pro
65                  70                  75                  80

Phe Pro Gln Pro Gln Leu Pro Tyr Ser Gln Pro Gln Pro Phe Gln Pro
                85                  90                  95

Gln Gln Pro Tyr Pro Gln Pro Gln Pro Gln Tyr Ser Gln Pro Gln Gln
                100                 105                 110

Pro Ile Ser Gln Gln Gln Gln Gln Gln Gln Gln Gln Gln Gln Gln Gln
            115                 120                 125

Gln Gln Gln Gln Gln Gln Gln Pro Gln Gln Ile Gln Pro Gln Ile
    130                 135                 140

Leu Gln Gln Gln Leu Ile Pro Cys Met Asp Val Val Leu Gln Gln His
145                 150                 155                 160

Asn Ile Ala Gln Gly Arg Ser Gln Val Leu Gln Gln Ser Thr Tyr Gln
                165                 170                 175

Leu Leu Gln Glu Leu Cys Cys Gln His Leu Trp Gln Ile Pro Glu Gln
                180                 185                 190

Ser Gln Cys Gln Ala Ile His Asn Val His Ala Ile Ile Leu His
            195                 200                 205

Gln Gln Gln Lys Gln Gln Gln Gln Gln Gln Lys Gln Gln Pro Ser
    210                 215                 220

Ser Gln Val Ser Phe Gln Gln Pro Gln Gln Gln Tyr Pro Ser Gly Gln
225                 230                 235                 240

Gly Ser Phe Arg Pro Ser Leu Gln Asn Pro Gln Ala Gln Gly Ser Val
                245                 250                 255

Gln Pro Gln Gln Leu Pro Gln Phe Ala Glu Ile Arg Asn Leu Ala Leu
            260                 265                 270

Gln Thr Leu Pro Ala Met Cys Asn Val Tyr Ile Pro Pro His Cys Ser
        275                 280                 285

Thr Thr Thr Ala Pro Phe Gly Ile Phe Gly Thr Asn
        290                 295                 300

<210> SEQ ID NO 59
<211> LENGTH: 303
<212> TYPE: PRT
<213> ORGANISM: Unknown
<220> FEATURE:
<223> OTHER INFORMATION: Triticum macha

<400> SEQUENCE: 59

Met Lys Thr Phe Leu Ile Leu Ala Leu Leu Ala Ile Val Ala Thr Thr
1               5                   10                  15

Ala Thr Ile Ala Val Arg Val Pro Val Pro Gln Leu Gln Pro Gln Asn

```
                20                  25                  30
Pro Ser Gln Gln Gln Pro Gln Glu Gln Val Pro Leu Val Gln Gln Gln
         35                  40                  45

Gln Phe Pro Gly Gln Gln Pro Phe Pro Pro Gln Gln Pro Tyr Pro
 50                  55                  60

Gln Leu Gln Pro Phe Pro Ser Gln Gln Pro Tyr Met Gln Leu Gln Pro
 65                  70                  75                  80

Phe Pro Gln Pro Gln Leu Pro Tyr Pro Gln Pro Gln Leu Pro Tyr Pro
                 85                  90                  95

Gln Arg Gln Pro Phe Arg Pro Gln Gln Pro Tyr Pro Gln Pro Gln Pro
                100                 105                 110

Gln Tyr Ser Gln Pro Gln Gln Pro Ile Ser Gln Gln Gln Gln Gln Gln
                115                 120                 125

Gln Gln Gln Gln Gln Lys Gln Gln Gln Gln Gln Gln Gln Gln Gln Ile
                130                 135                 140

Gln Pro Gln Ile Leu Gln Gln Leu Ile Pro Cys Arg Asp Val Val
145                 150                 155                 160

Leu Gln Gln His Ser Ile Ala Tyr Gly Ser Ser Gln Val Leu Gln Gln
                165                 170                 175

Ser Thr Tyr Gln Leu Val Gln Gln Leu Cys Cys Gln Gln Leu Trp Gln
                180                 185                 190

Ile Pro Glu Gln Ser Arg Cys Gln Ala Ile His Asn Val Val His Ala
                195                 200                 205

Ile Ile Leu His Gln Gln Gln Lys Gln Gln Gln Gln Gln Gln Gln Lys
                210                 215                 220

Gln Pro Leu Ser Gln Val Ser Phe Gln Gln Pro Gln Gln Tyr Pro
225                 230                 235                 240

Ser Gly Gln Gly Ser Phe Gln Pro Ser Gln Gln Asn Pro Gln Ala Gln
                245                 250                 255

Gly Ser Val Gln His Gln Gln Leu Pro Gln Phe Glu Glu Ile Arg Lys
                260                 265                 270

Leu Ala Leu Gln Thr Leu Pro Ala Val Cys Asn Val Tyr Ile Pro Pro
                275                 280                 285

Tyr Cys Ser Thr Thr Thr Ala Pro Phe Gly Ile Phe Gly Thr Asn
                290                 295                 300

<210> SEQ ID NO 60
<211> LENGTH: 290
<212> TYPE: PRT
<213> ORGANISM: Secale cereale

<400> SEQUENCE: 60

Met Lys Thr Phe Leu Ile Leu Ala Leu Leu Ala Ile Val Ala Thr Thr
 1               5                  10                  15

Ala Thr Ile Ala Val Arg Val Pro Val Pro Gln Leu Gln Pro Gln Asn
                 20                  25                  30

Pro Ser Gln Gln Gln Pro Gln Glu Gln Val Pro Leu Val Gln Gln Gln
                 35                  40                  45

Gln Phe Pro Gly Gln Gln Pro Phe Pro Pro Gln Gln Pro Tyr Pro
 50                  55                  60

Gln Pro Gln Pro Phe Pro Ser Gln Gln Pro Tyr Leu Gln Leu Gln Pro
 65                  70                  75                  80

Phe Pro Gln Pro Gln Leu Pro Tyr Pro Gln Pro Gln Leu Pro Tyr Pro
                 85                  90                  95
```

```
Gln Arg Gln Pro Phe Arg Pro Gln Gln Pro Tyr Pro Gln Pro
                100                 105                 110
Gln Tyr Ser Gln Pro Gln Gln Pro Ile Ser Gln Gln Gln Gln Gln
        115                 120                 125
Gln Gln Gln Gln Gln Gln Gln Gln Gln Gln Ile Pro Gln
        130                 135                 140
Ile Leu Gln Gln Gln Leu Ile Pro Cys Arg Asp Val Val Leu Gln Gln
145                 150                 155                 160
His Asn Ile Ala His Gly Ser Ser Gln Ile Leu Gln Gln Ser Thr Tyr
                165                 170                 175
Gln Leu Val Gln Gln Leu Cys Cys Gln Gln Leu Trp Gln Ile Pro Glu
                180                 185                 190
Gln Ser Arg Cys Gln Ala Ile His Asn Val Val His Ala Ile Ile Leu
                195                 200                 205
His Gln Gln Gln Gln Pro Ser Ser Gln Val Ser Phe Gln Gln Pro
                210                 215                 220
Gln Gln Gln Tyr Pro Ser Gly Gln Gly Ser Phe Gln Pro Ser Gln Gln
225                 230                 235                 240
Asn Pro Gln Ala Gln Gly Ser Val Gln Pro Gln Leu Pro Gln Phe
                245                 250                 255
Glu Glu Ile Arg Asn Leu Ala Leu Gln Thr Leu Pro Ala Met Cys Asn
                260                 265                 270
Val Tyr Ile Pro Pro Tyr Cys Thr Thr Ala Pro Val Gly Ile Phe Gly
                275                 280                 285
Thr Asn
    290

<210> SEQ ID NO 61
<211> LENGTH: 291
<212> TYPE: PRT
<213> ORGANISM: Triticum spelta

<400> SEQUENCE: 61

Met Lys Thr Phe Leu Ile Leu Ala Leu Leu Ala Ile Val Ala Thr Thr
1               5                   10                  15
Ala Thr Ile Ala Val Arg Val Pro Val Pro Gln Leu Gln Pro Gln Asn
                20                  25                  30
Pro Ser Gln Gln Gln Pro Gln Gly Gln Val Pro Leu Val Gln Gln Gln
            35                  40                  45
Gln Phe Leu Gly Gln Gln Gln Pro Phe Pro Gln Gln Pro Tyr Pro
        50                  55                  60
Gln Pro Gln Pro Phe Pro Ser Gln Gln Pro Tyr Leu Gln Leu Gln Pro
65                  70                  75                  80
Phe Pro Gln Pro Gln Leu Pro Tyr Ser Gln Pro Gln Pro Phe Arg Pro
                85                  90                  95
Gln Gln Pro Tyr Pro Gln Pro Gln Pro Gln Tyr Ser Gln Pro Gln Gln
                100                 105                 110
Pro Ile Ser Gln Gln Gln Gln Gln Gln Gln Gln Gln Gln Gln
            115                 120                 125
Gln Gln Gln Gln Gln Gln Gln Gln Ile Gln Pro Gln Ile Leu Gln
        130                 135                 140
Gln Gln Leu Ile Pro Cys Met Asp Val Leu Gln Gln His Asn Ile Ala
145                 150                 155                 160
His Gly Arg Ser Gln Val Leu Gln Gln Ser Thr Tyr Gln Leu Leu Gln
                165                 170                 175
```

```
Glu Leu Cys Cys Gln His Leu Trp Gln Ile Pro Glu Gln Ser Gln Cys
            180                 185                 190

Gln Ala Ile His Asn Val Val His Ala Ile Ile Leu His Gln Gln Gln
            195                 200                 205

Lys Gln Gln Gln Gln Leu Ser Ser Gln Val Ser Phe Gln Gln Pro Gln
        210                 215                 220

Gln Gln Tyr Pro Leu Gly Gln Gly Ser Phe Arg Pro Ser Gln Gln Asn
225                 230                 235                 240

Ser Gln Ala Gln Gly Ser Val Gln Pro Gln Gln Leu Pro Gln Phe Gln
                245                 250                 255

Glu Ile Arg Asn Leu Ala Leu Gln Thr Leu Pro Ala Met Cys Asn Val
            260                 265                 270

Tyr Ile Pro Pro Tyr Cys Ser Thr Thr Thr Ala Pro Phe Gly Ile Phe
            275                 280                 285

Gly Thr Asn
    290

<210> SEQ ID NO 62
<211> LENGTH: 299
<212> TYPE: PRT
<213> ORGANISM: Triticum urartu

<400> SEQUENCE: 62

Met Lys Thr Phe Leu Ile Leu Ala Leu Leu Ala Ile Val Ala Thr Thr
1               5                   10                  15

Ala Thr Thr Ala Val Arg Val Pro Val Pro Gln Leu Gln Pro Gln Asn
            20                  25                  30

Pro Ser Gln Gln Gln Pro Gln Glu Gln Val Pro Leu Val Gln Gln Gln
        35                  40                  45

Gln Phe Leu Gly Gln Gln Pro Phe Pro Pro Gln Gln Pro Tyr Pro
    50                  55                  60

Glu Pro Gln Pro Phe Pro Ser Gln Gln Pro Tyr Leu Gln Leu Gln Pro
65                  70                  75                  80

Phe Pro Gln Pro Gln Leu Pro Tyr Ser Gln Pro Gln Pro Phe Arg Pro
                85                  90                  95

Gln Gln Pro Tyr Pro Gln Pro Gln Pro Gln Tyr Ser Gln Pro Gln Gln
            100                 105                 110

Pro Ile Ser Gln Gln Gln Gln Gln Gln Gln Gln Gln Gln Gln Gln Gln
        115                 120                 125

Gln Gln Gln Gln Gln Gln Gln Glu Gln Gln Ile Gln Pro Gln Ile
        130                 135                 140

Leu Gln Gln Gln Leu Ile Pro Cys Arg Asp Val Ile Val Leu Gln Gln
145                 150                 155                 160

His Asn Ile Ala His Glu Ser Ser Gln Val Leu Gln Gln Ser Ser Tyr
                165                 170                 175

Gln Val Leu Gln Gln Leu Cys Cys Gln Gln Leu Trp Gln Ile Pro Glu
            180                 185                 190

Gln Ser Arg Cys Gln Ala Ile His Asn Val Val His Ala Ile Ile Leu
            195                 200                 205

His Gln Gln Gln Gln Gln Gln Gln Val Gln Gln Pro Ser Ser
        210                 215                 220

Gln Val Ser Tyr Gln Gln Pro Gln Gln Tyr Pro Ser Gly Gln Gly
225                 230                 235                 240

Ser Phe Gln Pro Ser Gln Gln Asn Pro Gln Ala Gln Gly Phe Val Gln
```

```
                        245                 250                 255
Pro Gln His Leu Pro Gln Phe Glu Glu Ile Arg Asn Leu Ala Leu Gln
            260                 265                 270

Thr Leu Pro Ala Met Cys Asn Val Tyr Ile Pro Pro Tyr Cys Ser Thr
            275                 280                 285

Thr Thr Ala Pro Phe Gly Ile Phe Gly Thr Asn
            290                 295

<210> SEQ ID NO 63
<211> LENGTH: 316
<212> TYPE: PRT
<213> ORGANISM: Unknown
<220> FEATURE:
<223> OTHER INFORMATION: Gliadin reference sequence, unknown species

<400> SEQUENCE: 63

Met Lys Thr Phe Leu Ile Leu Ala Leu Leu Ala Ile Val Ala Thr Thr
1               5                   10                  15

Ala Thr Thr Ala Val Arg Val Pro Val Pro Gln Leu Gln Pro Gln Asn
            20                  25                  30

Pro Ser Gln Gln Gln Pro Gln Glu Gln Val Pro Leu Val Gln Gln Gln
        35                  40                  45

Gln Phe Pro Gly Gln Gln Gln Phe Pro Pro Gln Gln Pro Tyr Pro
    50                  55                  60

Gln Pro Gln Pro Phe Pro Ser Gln Gln Pro Tyr Leu Gln Leu Gln Pro
65                  70                  75                  80

Phe Pro Gln Pro Gln Pro Phe Pro Pro Leu Pro Tyr Pro Gln Pro Gln
                85                  90                  95

Ser Phe Ser Pro Gln Gln Pro Tyr Pro Gln Gln Pro Gln Tyr Leu
            100                 105                 110

Gln Pro Gln Gln Pro Ile Ser Gln Gln Ala Gln Gln Gln Gln Gln
        115                 120                 125

Gln Gln Gln Gln Gln Gln Gln Gln Ile Gln Pro Gln Ile Leu
    130                 135                 140

Gln Gln Gln Leu Ile Pro Cys Arg Asp Val Val Leu Gln Gln His Asn
145                 150                 155                 160

Ile Ala His Ala Ser Ser Gln Val Leu Gln Gln Ser Thr Tyr Gln Leu
                165                 170                 175

Leu Gln Gln Leu Cys Cys Gln Gln Leu Leu Gln Ile Pro Glu Gln Ser
            180                 185                 190

Gln Cys Gln Ala Ile His Asn Val Ala His Ala Ile Ile Met His Gln
        195                 200                 205

Gln Gln Gln Gln Gln Gln Glu Gln Lys Gln Gln Leu Gln Gln Gln
    210                 215                 220

Gln Gln Gln Gln Gln Leu Gln Gln Gln Gln Gln Gln Pro Ser
225                 230                 235                 240

Ser Gln Val Ser Phe Gln Gln Pro Gln Gln Gln Tyr Pro Ser Ser Gln
                245                 250                 255

Val Ser Phe Gln Pro Ser Gln Leu Asn Pro Gln Ala Gln Gly Ser Val
            260                 265                 270

Gln Pro Gln Gln Leu Pro Gln Phe Ala Glu Ile Arg Asn Leu Ala Leu
        275                 280                 285
```

```
Gln Thr Leu Pro Ala Met Cys Asn Val Tyr Ile Pro Pro His Cys Ser
    290             295             300
Thr Thr Ile Ala Pro Phe Gly Ile Ser Gly Thr Asn
305             310             315
```

What is claimed is:

1. A method for determining effective sterilization, deimmunization, and/or disinfection of equipment and/or supplies by a device, the method comprising:
providing a defined surrogate protein having a predetermined sequence defined by a sequence which is at least about 95% homologous to the sequence

```
                                                            (SEQ ID NO: 1)
         10          20          30          40          50
MYNYTSAKYE  VPIAIQDRSF  NEDGSLNFPS  EGDNPTIHPY  WQPEFFGDTI

MVNGRVWPNM  NVDMTRYRFR  LLNGSNARFY  NLKFSNGMQF  WQIGTDGGYL

NKPVPLTSLL  ISPGERADIL  VDFTEIPAGT  RIILNNDANA  PYPTGDAPDK

DTTGQIMQFT  VQHNDHHHHH  H
``` representative of an infectious agent potentially contaminating the equipment and/or the supplies to be sterilized, deimmunized, and/or disinfected by the device;
subjecting the defined surrogate protein having the predetermined sequence to sterilization, deimmunization, or disinfection; and
determining the effectiveness of the sterilization, deimmunization, and/or disinfection by determining if the defined surrogate protein having the predetermined sequence has been destroyed; and wherein the sterilization, deimmunization, and/or disinfection occurs when the defined surrogate protein has been fragmented to yield a negative result in a protein analysis procedure.

2. The method of claim 1 in which the defined surrogate protein is a protein critical for stability, growth and/or infectious capacity of infectious agents.

3. The method of claim 1 in which the defined surrogate protein is a protein critical for stability, growth and/or infectious capacity of surrogate organisms of infectious agents.

4. The method of claim 2 in which the infectious agent includes one or more of: an infectious protein, an infectious spore forming bacteria, an infectious vegetative bacteria, an infections fungus, and an infectious virus.

5. The method of claim 1 in which the defined surrogate protein is a pathogenic protein, a protein critical for the growth of infectious agents, and an immunogenic protein.

6. The method of claim 1 in which the protein analysis procedure includes one or more of: a Western Blot analysis, a protein assay analysis, a magnetic separation analysis, a peptide analysis, a mass spectrometry analysis, and a gas chromatography analysis.

7. The method of claim 1 in which the protein analysis procedure includes fluorescence analysis of proteins covalently crosslinked on a solid surface.

8. The method of claim 1 in which the protein analysis procedure includes fluorescence analysis of proteins covalently crosslinked on magnetic beads.

9. The method of claim 1 in which the defined surrogate protein having the predetermined sequence is disposed on a surface.

10. The method of claim 1 in which the defined surrogate protein having the predetermined sequence is disposed on a test strip.

11. The method of claim 1 in which the defined surrogate protein having the predetermined sequence is disposed in or on a vessel.

12. The method of claim 1 in which the surrogate protein having the predetermined sequence is disposed on a tube.

13. The method of claim 1 in which the surrogate protein having the predetermined sequence is disposed on a holder.

14. The method of claim 13 in which the holder is disposed to receive a flow of a sterilization agent, a deimmunization agent or a disinfection agent.

15. A method for determining effective sterilization, deimmunization, and/or disinfection of equipment and/or supplies by a device, the method comprising:

providing a defined surrogate protein having a predetermined sequence defined by the sequence:

```
                                                      (SEQ ID NO: 1)
        10          20          30          40          50
MYNYTSAKYE  VPIAIQDRSF  NEDGSLNFPS  EGDNPTIHPY  WQPEFFGDTI

MVNGRVWPNM  NVDMTRYRFR  LLNGSNARFY  NLKFSNGMQF  WQIGTDGGYL

NKPVPLTSLL  ISPGERADIL  VDFTEIPAGT  RIILNNDANA  PYPTGDAPDK

DTTGQIMQFT  VQHNDHHHHH  H
``` representative of an infectious agent potentially contaminating the equipment and/or the supplies to be sterilized, deimmunized, and/or disinfected by the device;

subjecting the defined surrogate protein having the predetermined sequence to sterilization, deimmunization, or disinfection; and determining the eff